(12) United States Patent
Ripley et al.

(10) Patent No.: US 8,637,740 B2
(45) Date of Patent: Jan. 28, 2014

(54) **OMEGA-9 QUALITY *BRASSICA JUNCEA***

(75) Inventors: Van Leonard Ripley, Grandora (CA); Steven Arnold Thompson, Carmel, IN (US); Zoe Christina Ehlert, Saskatoon (CA)

(73) Assignee: Dow AgroSciences, LLC., Indianapolis, IN (US)

( * ) Notice: Subject to any disclaimer, the term of this patent is extended or adjusted under 35 U.S.C. 154(b) by 453 days.

(21) Appl. No.: 12/590,197

(22) Filed: Nov. 4, 2009

(65) Prior Publication Data

US 2010/0143570 A1    Jun. 10, 2010

Related U.S. Application Data

(60) Provisional application No. 61/198,422, filed on Nov. 4, 2008.

(51) Int. Cl.
*A01H 5/00* (2006.01)
*A01H 1/00* (2006.01)
*A23K 1/00* (2006.01)

(52) U.S. Cl.
USPC .......................... 800/306; 800/264; 426/615

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 4,769,061 A | 9/1988 | Comai | |
| 4,810,648 A | 3/1989 | Stalker | |
| 4,940,835 A | 7/1990 | Shah et al. | |
| 4,975,374 A | 12/1990 | Goodman et al. | |
| 5,015,580 A | 5/1991 | Christou et al. | |
| 5,188,958 A | 2/1993 | Moloney et al. | |
| 5,266,317 A | 11/1993 | Tomalski et al. | |
| 5,322,783 A | 6/1994 | Tomes et al. | |
| 5,494,813 A | 2/1996 | Hepher et al. | |
| 5,563,055 A | 10/1996 | Townsend et al. | |
| 5,625,130 A | 4/1997 | Grant et al. | |
| 5,647,899 A | 7/1997 | Lightcap, Jr. | |
| 5,668,299 A | 9/1997 | Debonte et al. | |
| 5,750,481 A | 5/1998 | Del Vecchio et al. | |
| 5,767,338 A | 6/1998 | Fan | |
| 5,840,946 A | 11/1998 | Wong et al. | |
| 5,844,086 A | 12/1998 | Murray | |
| 5,850,026 A | 12/1998 | DeBonte et al. | |
| 5,861,187 A | 1/1999 | DeBonte et al. | |
| 5,959,185 A | 9/1999 | Streit et al. | |
| 5,973,234 A | 10/1999 | Mueller et al. | |
| 5,976,560 A | 11/1999 | Han | |
| 5,977,445 A | 11/1999 | Soper et al. | |
| 6,045,779 A | 4/2000 | Mueller et al. | |
| 6,051,756 A | 4/2000 | Chin et al. | |
| 6,063,947 A | 5/2000 | DeBonte et al. | |
| 6,084,157 A | 7/2000 | DeBonte et al. | |
| 6,169,190 B1 | 1/2001 | Lanuza et al. | |
| 6,210,700 B1 | 4/2001 | Valente et al. | |
| 6,248,876 B1 | 6/2001 | Barry et al. | |
| 6,297,056 B1 | 10/2001 | Tulsieram et al. | |
| 6,303,849 B1 | 10/2001 | Potts et al. | |
| 6,310,002 B1 | 10/2001 | Krzoska et al. | |
| 2,323,392 A1 | 11/2001 | Charne | |
| 6,441,278 B1 | 8/2002 | Debonte | |
| 6,686,417 B1 | 2/2004 | Reekmans et al. | |
| 6,689,722 B1 | 2/2004 | Holst-Grubbe et al. | |
| 6,887,283 B1 | 5/2005 | Ginosar et al. | |
| 6,967,243 B2 | 11/2005 | Debonte et al. | |
| 7,384,989 B2 | 6/2008 | Allard et al. | |
| 7,423,198 B2 | 9/2008 | Yao et al. | |
| 7,528,097 B2 | 5/2009 | Hanson et al. | |
| 7,538,236 B2 | 5/2009 | Narine et al. | |
| 7,605,301 B2 | 10/2009 | Yao et al. | |
| 2003/0221217 A1 | 11/2003 | Yao et al. | |
| 2005/0031767 A1 | 2/2005 | Schweizer et al. | |
| 2005/0039233 A1 | 2/2005 | Yao et al. | |
| 2006/0248611 A1 | 11/2006 | Hu et al. | |
| 2008/0168587 A1 | 7/2008 | Yao et al. | |
| 2009/0093366 A1 | 4/2009 | Wright et al. | |

FOREIGN PATENT DOCUMENTS

| | | |
|---|---|---|
| EP | 0333033 | 9/1987 |
| EP | 0242246 | 10/1987 |
| EP | 1862551 | 12/2007 |
| WO | 9111169 | 8/1991 |
| WO | 9302197 | 2/1993 |
| WO | 9306487 | 4/1993 |
| WO | 9319181 | 9/1993 |
| WO | 9516776 | 6/1995 |
| WO | 9518855 | 7/1995 |
| WO | 9630517 | 10/1996 |

(Continued)

OTHER PUBLICATIONS

Yaniv et al, Industrial Crops and Products 3: 247-251, 1995.*
Holman et al., The Rates of Oxidation of Unsaturated Fatty Acids and Esters, J. Am. Oil Chem. Soc., vol. 24, pp. 127-129, 1947.
Horsch et al., A Simple and General Method for Transferring Genes into Plants, Science, vol. 227, pp. 1229-1231, Mar. 8, 1985.

(Continued)

*Primary Examiner* — Elizabeth McElwain
(74) *Attorney, Agent, or Firm* — Marcia I. Rosenfeld; TraskBritt, P.C.

(57) ABSTRACT

The invention relates to improved *Brassica* species, including *Brassica juncea*, improved oil and meal from *Brassica juncea*, methods for generation of such improved *Brassica* species, and methods for selection of *Brassica* lines. Further embodiments relate to seeds of *Brassica juncea* comprising an endogenous oil having increased oleic acid content and decreased linolenic acid content relative to presently existing commercial cultivars of *Brassica juncea*, seeds of *Brassica juncea* having traits for increased oleic acid content and decreased linolenic acid content in seed oil stably incorporated therein, and one or more generations of progeny plants produced from said seeds.

13 Claims, 5 Drawing Sheets

(56) References Cited

FOREIGN PATENT DOCUMENTS

| WO | 9630530 | 10/1996 |
|---|---|---|
| WO | 9726318 | 7/1997 |
| WO | 9727761 | 8/1997 |
| WO | 9743907 | 11/1997 |
| WO | 0051415 | 9/2000 |
| WO | 0062748 | 10/2000 |
| WO | 03053157 | 7/2003 |
| WO | 2004009789 | 1/2004 |
| WO | WO2004/072259 | 8/2004 |
| WO | 2005012515 | 2/2005 |
| WO | 2005107437 | 11/2005 |
| WO | 2005107590 | 11/2005 |
| WO | 2006079567 | 8/2006 |
| WO | 2007053482 | 5/2007 |
| WO | 2007104102 | 9/2007 |
| WO | 2008024840 | 2/2008 |
| WO | 2008070845 | 6/2008 |
| WO | 2009007166 | 1/2009 |
| WO | 2009038108 | 3/2009 |
| WO | 2009069600 | 6/2009 |
| WO | 2009078857 | 6/2009 |

OTHER PUBLICATIONS

Huang et al., Parallelization of a Local Similarity Algorithm, Cabios, vol. 8, No. 2, 1992, pp. 155-165.

Huub et al., Tobacco Proteinase Inhibitor I Genes are Locally, but not Systemically Induced by Stress, Plant Molecular Biology, vol. 21, pp. 985-992, 1993.

Jain et al., High Frequency Regeneration and Heritable Somaclonal Variation in *Brassica juncea*, Euphytica, vol. 40, pp. 75-81 (1989).

Jaynes et al., Expression of a Cecropin B Lytic Peptide Analog in Transgeneic Tobacco Confers Enhanced Resistance to Bacterial Wilt Caused by Pseudomonas Solanacearum, Plant Science, vol. 89 (1993) pp. 43-53.

Jones et al., A Dominant Nuclear Streptomycin Resistance Marker for Plant Cell Transformation, Mol. Gen. Genetics (1987) vol. 210, pp. 86-91.

Jones et al., Isolation of the Tomato Cf-9 Gene for Resistance to Cloadosporium Fulvum by Transposon Tagging, Science, vol. 266, Nov. 4, 1994, pp. 789-793.

Kado, Molecular Mechanisms of Crown Gall, Critical Reviews in Plant Sciences, vol. 10, No. 1, pp. 1-32 (1991).

Kalderon et al., A Short Amino Acid Sequence Able to Specify Nuclear Location, Cell, vol. 39, pp. 499-509, Dec. 1984.

Karlin et al., Applications and Statistics for Multiple High-Scoring Segments in Molecular Sequences, Proc. Natl. Acad. Sci. USA, vol. 90, pp. 5873-5877, Jun. 1993.

Kartha et al., In Vitro Plant Formation from Step Explants of Rape (*Brassica napus* CV. Zephyr), Physiol. Plant, vol. 31, pp. 217-220 (1974).

Kawalleck et al., Polyubiquitin Gene Expression and Structural properties of the ubi4-2 Gene in *Petroselinum crispum*, Plant Molecular Biology, 1993; 21:673-684.

Kirti et al., A Simple Method of Inducing Somatic Embryogenesis in *Brassica juncea* (L.) Czern & Cross, Plant Breeding, 1989; 102:73-78.

Klein et al., Factors Influencing Gene Delivery into *Zea mays* Cells by High-Velocity Microprojectiles, Bio/Technology May 1998; 6:559-563.

Klein et al., Transformation of Microbes, Plants and Animals by Particle Bombardment, Bio/Technology, Mar. 1992; 10:286-291.

Knox et al., Structure and organization of Two Divergent α-amylase Genes from Barley, Plant Molecular Biology, 1987; 9:3-17.

Knutzon et al., Modification of Brassica Seed Oil by Antisense Expression of a Stearoyl-acyl Carrier Protein Desaturase Gene, Proc. Natl. Acad. Sci., Apr. 1992; 89:2624-2628.

Kramer et al., Sequence of a cDNA and Expression of the Gene Encoding Epedermal and Gut Chitinases of *Manduca sexta*, Insect Biochem. Molec. Biol., 1993; 23(6):691-701.

Lamb et al., Emerging Strategies for Enhancing Crop Resistance to Microbial Pathogens, Bio/Technology, Nov. 1992; 10:1436-1445.

Landry, DNA Mapping in Plants, Glick and Thompson, Methods in Plant Molecular Biology and Biotechnology, CRC Press, Boca Raton (1993) pp. 269-284.

Last et al., pEmu: An Improved Promoter for Gene Expression in Cereal Cells, Theor. Appl. Genet., 1991; 81:581-588.

Laursen et al., Production of Fertile Transgenic Maize by Electroporation of Suspension Culture Cells, Plant Molecular Biology, 1994; 24:51-61.

Lee et al., The Molecular Basis of Sulfonylurea Herbicide Resistance in Tobacco, The EMBO Journal, 1998; 7 (5):1241-1248.

Lepetit et al., A Plant Histone Gene Promoter can Direct both Replication-Dependent and -Independent Gene Expression in Transgenic Plants, 1992; 231:276-285.

Lerner et al., Cloning and Characterization of Root-Specific Barley Lectin, Plant Physiol., Mar. 1989; 91:124-129.

Logemann et al., Expression of a Barley Robosome-Inactivating Protein Leads to Increased Fungal Protection in Transgenic Tobacco Plants, Bio/Technology, 1992; 10:305-308.

Marshall et al., Allelic Mutations in Acetyl-Coenzyme A Carboxylase Confer Herbicide Tolerance in Maize, Theor. Appl. Genet., 1992: 83:435-442.

Martin et al., Map-Based Cloning of a Protein Kinase Gene Conferring Disease Resistance in Tomato, Science, Nov. 1993; 262:1432-1436.

Matsuoka et al., Propeptide of a Precursor to a Plant Vacuolar Protein Required for Vacuolar Targeting, Proc. Natl. Acad. Sci. USA, Feb. 1991; 88:834-838.

McElroy et al., Isolation of an Efficient Actin Promoter for Use in Rice Transformation, The Plant Cell, Feb. 1990; 2:163-171.

Mein et al., Evaluation of Single Nucleotide Polymorphism Typing with Invader on PCR Amplicons and Its Automation, Genome Research, 2000; 10:30-343.

Mett et al., Copper-Controllable Gene Expression System for Whole Plants, Proc. Natl. Acad. Sci. USA, May 1993; 90:4567-4571.

Miki et al., Procedures for Introducing Foreign DNA into Plants, in Methods in Plant Molecular biology and Biotechnology, Glick and Thompson, 1993; pp. 67-88.

Miki et al., Transformation of *Brassica napus* Canola Cultivars with *Arabidopsis thaliana* Acetohydroxyacid Synthase Genes and Analysis of Herbicide Resistance, Theor. Appl. Genet., 1990; 80:449-458.

Mindrinos et al., The *A. thaliana* Disease Resistance Gene RPS2 Encodes a Protein Containing a Nuleotide-Binding Site and Leucine-Rich Repeats, Cell, Sep. 1994, 78:1089-1099.

Moloney et al., High Efficiency Transformation of *Brassica napus* Using Agrobacterium Vectors, Plant Cell Reports, 1989; 8:238-242.

Murai et al., Phaseolin Gene from Bean is Expressed After Transfer to Sunflower Via Tumor-Inducing Plasmid Vectors, Science, 1983; 222:476-482.

Myakishev et al., High-Throughput SNP Genotyping by Allele-Specific PCR with Universal Energy-Transfer-Labeled Primers, Genome Research, 2001; 11:163-169.

Myers et al., Optimal Alignments in Linear Space, Cabios, 1988; 4:11-17.

Napoli et al., Introduction of a Chimeric Chalcone Synthase Gene into Petunia Results in Reversible Co-Suppression of Homologous Genes in Trans, The Plant Cell, Apr. 1990; 2:279-289.

Narasimhulu et al., Species Specific Shoot Regeneration Response of Cotyledonary Explants of Brassicas, Plant Cell Reports, 1988; 7:104-106.

Needleman et al., A General Method Applicable to the Search for Similarities in the Amino Acid Sequence of Two Proteins, J. Mol. Biol., 1970; 48:443-453.

Odell et al., Identification of DNA Sequences Required for Activity of the Cauliflower Mosaic Virus 35S Promoter, Nature, 1985; 313:810-812.

Okuley et al., Arabidopsis FAD2 Gene Encodes the Enzyme that is Essential for Polyunsaturated Lipid Synthesis, The Plant Cell, 1994; 6:147-158.

Orita et al., Detection of Polymorphisms of Human DNA by Gel Electrophoresis as Single-Strand Conformation Polymorphisms, Proc. Natl. Acad. Sci. USA, Apr. 1989; 86:2766-2770.

(56) References Cited

OTHER PUBLICATIONS

Pang et al., Expression of a Gene Encoding a Scorpion Insectotoxin Peptide in Yeast, Bacteria and Plants, Gene, 1992; 116:165-172.
Pearson et al., Improved Tools for Biological Sequence Comparison, Proc. Natl. Acad. Sci. USA, Apr. 1988; 85:2444-2448.
Pearson, Using the FASTA Program to Search Protein and DNA Sequence Databases, Methods in Molecular Biology, 1994; 24:307-331.
Pen et al., Production of Active *Bacillus licheniformis* Alpha-Amylase in Tobacco and its Application in Starch Liquefaction, Bio/Technology, Mar. 1992; 10:292-296.
Poehlman et al., Backcross Breeding, Methods in Plant Breeding, IV Edition, 1995, pp. 172-175.
Potts et al., Canola-Quality *Brassica juncea*, A New Oilseed Crop for the Canadian Prairies, 10th International Rapeseed Congress, Canberra, Australia, 1999, 6 pages.
Pratt et al., Identification of an Allatostatin from Adult Diploptera Punctata, Biochemical and Biophysical Research Communications, Sep. 1989; 163(3):1243-1247.
Przibilla et al., Site-Specific Mutagenesis of the D1 Subunit of Photosystem II in Wild-Type Chlamydomonas, The Plant Cell, Feb. 1991; 3:169-174.
Pua et al., Transgenic Plants of *Brassica napus* L., Bio/Technology, 1987; 5:815-817.
Raboy et al., A Survey of Maize Kernal Mutants for Variation in Phytic Acid, Maydica, 1990; 35:383-390.
Reagan, Expression Cloning of an Insect Diuretic Hormone Receptor, J. Biol. Chem., 1994; 269(1):9-12.
Roder et al., Efficiency of the Tetracycline-Dependent Gene Expression System: Complete Suppression and Efficient Induction of the rolB Phenotype in Transgenic Plants, Mo. Gen. Genet., 1994; 243:32-38.
Sanford et al., Delivery of Substances into Cells and Tissues using a Particle Bombardment Process, Particulate Science and Technology, 1987; 5:27-37.
Sanford, Biolistic Plant Transformation; Physiologia Plantarum, 1990; 79:206-209.
Sanford, The Biolistic Process, Trends Biotech., Dec. 1988; 6:299-302.
Schena et al., A Steroid-Inducible Gene Expression System for Plant Cells, Proc. Natl. Sci. USA, Dec. 1991; 88:10421-10425.
Sengupta-Gopalan et al., Developmentally Regulated Expression of the Bean β-phaseolin Gene in Tobacco Seed, Proc. Natl. Acad. Sci. USA, May 1985; 82:3320-3324.
Shah et al., Engineering Herbicide Tolerance in Transgenic Plants, Science, Jul. 1986; 233:478-481.
Shiroza et al., Sequence Analysis of the *Streptococcus* Mutans Fructosyltransferase Gene and Flanking Regions, Journal of Bacteriology, Feb. 1988; 170(2):810-816.
Simpson et al., Light-Inducible and Tissue-Specific Expression of a Chimaeric Gene Under Control of the 5'-flanking Sequence of a Pea Chlorophyll a/b-binding Protein Gene, The EMBO Journal, 1985; 4(11):2723-2729.
Smith et al., Comparison of Biosequences, Advances in Applied Mathematics; 1981; 2:482-489.
Søgaard et al., Site-Directed Mutagenesis of Histidine 93, Aspartic Acid 180, Glutamic Acid 205, Histidine 209, and Aspartic Acid 291 at the Active Site and Tryptophan 279 at the Raw Starch Binding Site in Barley α-Amylase 1, The Journal of Biological Chemistry, Oct. 1993; 268(30):22480-22484.
Stalker et al., Herbicide Resistance in Transgenic Plants Expressing a Bacterial Detoxification Gene, Science, Oct. 1988; 242:419-423.
Steinmetz et al., The DNA Sequence of the Gene for the Secreted *Bacillus subtilis* Enzyme Levansucrase and its Genetic Control Sites, Mol. Gen. Genet., 1985; 200:220-228.
Stiefel et al., Expression of a Maize Cell Wall Hydroxyproline-Rich Glycoprotein Gene in Early Leaf and Root Vascular Differentiation, The Plant Cell, Aug. 1990; 2:785-793.

Sumitani et al., Molecular Cloning and Expression of proteinaceous α-Amylase Inhibitor Gene from Streptomyces Nitrosporeus in *Escherichia coli*, Biosci. Biotech. Biochem., 1993; 57(8):1243-1248.
Svab et al., Aminoglycoside-3"-Adenyltransferase Confers Resistance to Spectinomycin and Streptomycin in *Nicotiana tabacum*, Plant Molecular Biology, 1990; 14:197-205.
Swanson et al., The Characterization of Herbicide Tolerant Plants in *Brassica napus* L. After In Vitro Selection of Microspores and Protoplasts, Plant Cell Reports, 1988; 7:83-87.
Swanson et al., Microspore Mutagenesis and Selection: Canola Plants with Field Tolerance to the Imidazolinones, Theor. Appl. Genet, 1989; 78:252-530.
Swanson, Microspore Culture in *Brassica*, Methods in Molecular Biology, 1990; 6(17):159-169.
Tanhuanpää et al., Mapping and Cloning of FAD2 Gene to Develop Allele-Specific PCR Oleic Acid in Spring Turnip Rape (*Brassica rapa* ssp. Oleifera), Molecular Breeding, 1998; 4:543-550.
Täpp et al., Homogeneous Scoring of Single-Nucleotide Polymorphisms: Comparison of the 5'-Nuclease Taqman® Assay and Molecular Beacon Probes, BioTechniques, Apr. 2000; 28:732-738.
Tavladoraki et al., Trasgenic Plants Expressing a Functional Single-Chain Fv Antibody are Specifically Protected from Virus Attack, Nature, Dec. 1993; 366:469-472.
Thiagarajah et al., A Comparison of Genetic Segregation in Traditional and Microspore-Derived Populations of *Brassica juncea* L. Czern and Coss, Plant Breeding, 1993; 111:330-334.
Timko et al., Light Regulation of Plant Gene Expression by an Upstream Enhancer-Like Element, Nature, Dec. 1985; 318:579-582.
Toubart et al., Cloning and Characterization of the Gene Encoding the Endopolygalacturonase-Inhibiting Protein (PGIP) of *Phaseolus vulgaris* L., The Plant Journal, 1992; 2(3):367-373.
Twell et al., Activation and Developmental Regulation of an Arabidopsis Anther-Specific Promoter in Microspores and Pollen of *Nicotiana tabacum*, Sex Plant Reprod., 1993; 6:217:224.
Twell et al., Promoter Analysis of Genes that are Coordinately Expressed During Pollen Development Reveals Pollen-Specific Enhancer Sequences and Shared Regulatory Elements, Genes Dev. 1991 5:496-507.
Van Blokland et al., Transgene-Mediated Supression of Chalcone Synthase Expression in Petunia Hybrida Results from and Increase in RNA Turnover, The Plant Journal, 1994; 6(6):861-877.
Van Damme et al., Molecular Cloning of Mannose-Binding Lectins from *Clivia miniata*, Plant Molecular Biology, 1994; 24:825-830.
Van Den Elzen et al., A Chimaeric Hygromycin Resistance Gene as a Selectable Marker in Plant Cells, Plant Molecular Biology, 1985; 5:299-302.
Van Hartingsveldt et al., Cloning, Characterization and Overexpression of the Phytase-Encoding Gene (phyA) of Aspergillus Niger, Gene, 1993; 127:87-94.
Velten et al., Isolation of a Dual Plant Promoter Fragment from the Ti Plasmid of *Agrobacterium tumefaciens*, The EMBO Journal, 1984; 3(12):2723-2730.
Ward et al., Chemical Regulation of Transgene Expression in Plants, Plant Molecular Biology, 1993; 22:361-366.
Wijesundera et al., Canola Quality Indian Mustard Oil (*Brassica juncea*) is More Stable to Oxidation than Conventional Canola Oil (*Brassica napus*), J. Am. Oil Chem. Soc., 2008; 85:693-699.
Zhang et al., Efficient Transformation of Tobacco by Ultrasonication, Bio/Technology, 1991; 9:996-997.
Abe et al., Molecular Cloning of a Cysteine Proteinase Inhibitor of Rice (Oryzacystatin); The Journal of Biological Chemistry, vol. 262, No. 35, Dec. 15, 1987, pp. 16793-16797.
Altschul et al., Basic Local Alignment Search Tool, J. Mol. Biol., 1990, vol. 215, pp. 403-410.
Altschul et al., Gapped BLAST and PSI-BLAST: a new generation of protein database search programs, Nucleic Acids Research, 1997, vol. 25, No. 17, pp. 3389-3402.
Atanassova et al., A 126 by fragment of a plant histone gene promoter confers preferential expression in meristems of transgenic Arabidopsis, The Plant Journal, 1992, vol. 2, No. 3, pp. 291-300.
Barclay et al., Sunflower Oil May Help Reduce Nosocomial Infections in Preterm Infants, Medscape Medical News, <http://cme.medscape.com/viewarticle/501077>, released Mar. 8, 2005, 1 page.

(56) References Cited

OTHER PUBLICATIONS

Barsby et al., A rapid and efficient alternative procedure for the regeneration of plants from hypocotyl protoplasts of *Brassica napus*, Plant Cell Reports, 1986, vol. 5, pp. 101-103.
Beachy et al, Coat Protein-Mediated Resistance Against Virus Infection, Annual Reviews, Phytopathol, 1990, vol. 28, 451-474.
Becker et al., The cab-m7 gene: a light-inducible, mesophyll-specific gene of maize, Plant Molecular Biology, 1992, vol. 20, pp. 49-60.
Bhalla et al., Agrobacterium-mediated transformation of *Brasssica napus* and *Brassica oleracea*, Nature Protocols, 2008, vol. 3, No. 2, pp. 181-190.
Botella et al., Differential expression of two calmodulin genes in response to physical and chemical stimuli, Plant Molecular Biology, 1994, vol. 24, pp. 757-766.
Cardoza et al., Canola (*Brassica napus* L.) Methods in Molecular Biology, 2006, vol. 343, vol. 1, pp. 257-266.
Caviedes, Aqueous Processing of Rapeseed (Canola), Thesis for Degree of Master of Applied Science, University of Toronto 1996, pp. 1 147.
Charest et al., In vitro study of transgenic tobacco expressing Arabidopsis wild type and mutant acetohydroxyacid synthase genes, Plant Cell Reports, 1990, vol. 8, pp. 643-646.
Christensen et al., Sequence analysis and transcriptional regulation by heat shock of ployubiquitin transcripts from maize, Plant Molecular Biology, 1989, vol. 12, pp. 619-632.
Christensen et al., Maize polyubiquitin genes: structure, thermal perturbation of expression and transcript splicing, and promoter activity following transfer to protoplasts by electroporation, Plant Molecular Biology, 1992, vol. 18, pp. 675-689.
Christou et al., Stable Transformation of Soybean by Electroporation and Root Formation from Transformed Callus, Proc. Natl. Acad. Sci., Jun. 1987, vol. 84, pp. 3962-6966.
Chuong et al., A simple culture method for Brassica hypototyl protoplasts, Plant Cell Reports, 1985, vol. 4, pp. 4-6.
Comai et al., Expression in plants of a mutant aroA gene from *Salmonella typhimurium* confers tolerance to glyphosate, Nature, 1985, vol. 317, pp. 741-744.
Corpet et al., multiple sequence alignment with hierarchical clustering, Nucleic Acids Research, 1988, vol. 16, No. 22, pp. 10881-10890.
Creissen et al., Molecular characterization of glutathione reductase cxDNAs from pea (*Pisum sativum* L.), The Plant Journal, 1991, vol. 2, No. 1, pp. 129-131.
D'Halluin et al., Transgenic Maize Plants by Tissue Electroporation, The Plant Cell, 1992, vol. 4, pp. 1495-1505.
De Greef et al., Evaluation of Herbicide Resistance in Transgenic Crops Under Field Conditions, Biotechnology, Jan. 1989, vol. 7, pp. 61-64.
Deshayes et al., Liposome-mediated transformation of tobacco mesophyll protoplasts by an *Escherichia coli* plasmid, The EMBO Journal, 1985, vol. 4, No. 11, pp. 2731-2737.
Draper et al., Ti Plasmid Homologous Sequences Present in Tissues from Agrobacterium Plasmid-transformed Petunia Protoplasts, Plant & Cell Physiol., 1982, vol. 23, No. 3, pp. 451-458.
Eichholtz et al., Expression of Mouse Dihydrofolate Reductase Gene Confers Methotrexate Resistance in Transgenic Petunia Plants, Somatic Cell Molecular Genetics, 1987, vol. 13, No. 1, p. 67-76.
Elliot et al., Isolation and characterization of fruit vacuolar invertase genes from two tomato species and temporal differences in mRNA levels during fruit ripening, Plant Molecular Biology, 1993, vol. 21, pp. 515-524.
Fehr, Backcross Method, Principles of Cultivar Development, 1987, Chapter 28, pp. 360-376.
Fehr, Rapeseed and Mustard, Principles of Cultivar Development, 1987, Chapter 12, pp. 437-472.
Ferrie et al., Development of Methodology and Applications of Doubled Haploids in *Brassica rapa*, Proc. 9th International Rapeseed Congress, Jul. 4-7, 1995, Cambridge, vol. 3, pp. 807-809.
Fisher et al., Starch Branching Enzyme II from Maize Endosperm, Plant Physiol., 1993, vol. 102, pp. 1045-1046.
Fontes et al., Characterization of an Immunoglobulin Binding Protein Homolog in the Maiae floury-2 Endosperm Mutant, The Plant Cell, vol. 3, pp. 483-496, May 1991.
Fraley et al., Expression of Bacterial Genes in Plant Cells, Proc. Natl. Acad. Sci., USA, vol. 80, pp. 4803-4807, Aug. 1983.
Gatz et al., Regulation of a Modified CaMV 35S Promoter by the Tn10-Encoded Tet Repressor in Transgenic Tobacco, Mol. Gen. Genet. (1991) vol. 227, pp. 229-237.
Geiser et al., The Hypervariable Region in the Genes Coding for Entomopathogenic Crystal Proteins of *Bacillus thuringiensis*: Nucleotide Sequence of the Kurhd1 Gene of Subsp. Kurstaki HD1, Gene, vol. 48 (1986) pp. 109-118.
Gordon-Kamm et al., Transformation of Maize Cells and Regeneration of Fertile Transgenic Plants, The Plant Cell, vol. 2, pp. 603-618, Jul. 1990.
Gould et al., A Conserved Tripeptide Sorts Proteins to Peroxisomes, The Journal of Cell Biology, vol. 108, May 1989, pp. 1657-1664.
Griess et al., Isolation and Sequence Comparison of a Maize Calmodulin cDNA1, Plant Physiol. (1994) vol. 104, pp. 1467-1468.
Gruber et al., Vectors for Plant Transformation, Methods in Plant Molecular Biology and Biotechnology, Glick and Thompson, 1993, pp. 89-119.
Guerrero et al., Promoter Sequences from a Maize Pollen-Specific Gene Direct Tissue-Specific Transcription in Tobacco, Mol. Gen. Genetics, vol. 224 (1993) pp. 161-168.
Hain et al., Uptake, Integration, Expression and Genetic Transmission of a Selectable Chimaeric Gene by Plant Protoplasts, Mol. Gen Genetics, vol. 199 (1985) pp. 161-168.
Hammock et al., Expression and Effects of the Juvenile Hormone Esterase in a Baculovirus Vector, Letters to Nature, vol. 344, pp. 458-461, Mar. 29, 1990.
Hawrysh, Stability of Canola Oil, Canola and Rapeseed: Production, Chemistry, Nutrition, and Processing Technology, 1990, Chapter 7, pp. 99-122.
Hayes et al., Molecular Cloning and Heterologous Expression of a cDNA Encoding a Mouse Glutathione S-Transferase Yc Subunit Possessing High Catalytic Activity for Aflatoxin B1-8,9-Epoxide, Biochem. J. (1992) vol. 285, pp. 173-180.
Hayford et al., Development of a Plant Transformation Selection System Based on Expression of Genes Encoding Gentamicin Acetyltransferases, Plant Physiol., vol. 86 (1988) pp. 1216-1222.
Heney et al., The Purification of Avidin and its Derivatives on 2-Iminobiotin-6-Aminohexyl-Sepharose 4B, Analytical Biochemistry, vol. 114 (1981) pp. 92-96.
Heppard et al., Developmental and Growth Temperature Regulation of Two Different Microsomal w-6 Desaturase Genes in Soybeans, Plant Physiol. vol. 110 (1996) pp. 311-319.
Higgins et al., Fast and Sensitive Multiple Sequence Alignments on a Microcomputer, Cabios Communications, vol. 5, No. 2, 1989, pp. 151-153.
Higgins et al., Clustal: A Package for Performing Multiple Sequence Alignment on a Microcomputer, Gene, vol. 73, pp. 237-244 (1988).
Hille et al., Bleomycin Resistance: A New Dominant Selectable Marker for Plant Cell Transformation, Plant Molecular Biology, vol. 7, pp. 171-176, 1986.
PCT International Search Report for International Application No. PCT/US2009/005968, mailed Feb. 10, 2010, (5 pages).
PCT Written Opinion for International Application No. PCT/US2009/005968, mailed Feb. 10, 2010, (7 pages).
Hague et al., "Mutant *Brassica juncea* Lines with reduced linolenic acid," Journal of Genetics and Breeding, Dec. 2002, pp. 309-316, vol. 56, No. 4.
Rashid et al., "Development of yellow seeded *Brassica napus* through interspecific crosses" Plant Breeding, 1994 pp. 127-134, vol. 112, No. 2.
Burton, et al., "Assessment of genetic diversity in selected breeding lines and cultivars of canola quality *Brassica juncea* and their implications for canola breeding" Euphytica, Kluwer Academic Publishers, DO, Mar. 1, 2004, pp. 181-192, vol. 136, No. 2.
Schelfhout et al., "Tracing B-genome chromatin in *Brassica napus* x b-juncea interspecific progeny" Genome, Nov. 2006, pp. 1490-1497, vol. 49, No. 11.

* cited by examiner

```
  1 CAATCCCTCGCTCTTTCTCCTACCTCATCTGGGACATCATCATAGCCTCC  50
    ||||||||||||||||||||||||||||||||||||||||||||||||||
  1 CAATCCCTCGCTCTTTCTCCTACCTCATCTGGGACATCATCATAGCCTCC  50

51 TGCTTCTACTACGTCGCCACCACTTACTTCCCTCTCCTCCCTCACCCTCT 100
    ||||||||||||||||||||||||||||||||||||||||||||||||||
 51 TGCTTCTACTACGTCGCCACCACTTACTTCCCTCTCCTCCCTCACCCTCT 100

101 CTCCTACTTCGCCTGGCCTCTCTACTGGGCCTGCCAGGGCTGCGTCCTAA 150
    ||||||||||||||||||||||||||||||||||||||||||||||||||
101 CTCCTACTTCGCCTGGCCTCTCTACTGGGCCTGCCAGGGCTGCGTCCTAA 150

151 CCGGCGTCTGGGTCATAGCCCACGAGTGCGGCCACCACGCCTTCAGCGAC 200
    ||||||||||||||||||||||||||||||||||||||||||||||||||
151 CCGGCGTCTGGGTCATAGCCCACGAGTGCGGCCACCACGCCTTCAGCGAC 200

201 TACCAGTGGCTGGACGACACCGTCGGCCTCATCTTCCACTCCTTCCTCCT 250
    ||||||||||||||||||||||||||||||||||||||||||||||||||
201 TACCAGTGGCTGGACGACACCGTCGGCCTCATCTTCCACTCCTTCCTCCT 250

251 CGTCCCTTACTTCTCCTGGAAGTACAGTCATCGACGCCACCATTCCAACA 300
    ||||||||||||||||||||||||||||||||||||||||||||||||||
251 CGTCCCTTACTTCTCCTGGAAGTACAGTCATCGACGCCACCATTCCAACA 300

301 CTGGCTCCCTCGAGAGAGACGAAGTGTTTGTCCCCAAGAAGAAGTCAGAC 350
    ||||||||||||||||||||||||||||||||||||||||||||||||||
301 CTGGCTCCCTCGAGAGAGACGAAGTGTTTGTCCCCAAGAAGAAGTCAGAC 350
                                              . Forward .
351 ATCAAGTGGTACGGCAAGTACCTCAACAACCCTTTGGGACGCACCGTGAT 400
    ||||||||||||||||||||||||||||||||||||||||||||||||||
351 ATCAAGTGGTACGGCAAGTACCTCAACAACCCTTTGGGACGCACCGTGAT 400
       primer ▼
401 GTTAACGGTTTAGTTCACTCTCGGCTGGCCTTTGTACTTAGCCTTCAACG 450
    |||||||||| |||||||||||||||||||||||||||||||||||||||
401 GTTAACGGTTGAGTTCACTCTCGGCTGGCCTTTGTACTTAGCCTTCAACG 450

451 TCTCGGGGAGACCTTACGACGGCGGCTTCGCTTGCCATTTCCACCCCAAC 500
    ||||||||||||||||||||||||||||||||||||||||||||||||||
451 TCTCGGGGAGACCTTACGACGGCGGCTTCGCTTGCCATTTCCACCCCAAC 500

501 GCTCCCATCTACAACGACCGTGAGCGTCTCCAGATATACATCTCCGACGC 550
    ||||||||||||||||||||||||||||||||||||||||||||||||||
501 GCTCCCATCTACAACGACCGTGAGCGTCTCCAGATATACATCTCCGACGC 550

551 TGGCATCCTCGCCGTCTGCTACGGTCTCTACCGCTACGCTGCTGTCCAAG 600
    ||||||||||||||||||||||||||||||||||||||||||||||||||
551 TGGCATCCTCGCCGTCTGCTACGGTCTCTACCGCTACGCTGCTGTCCAAG 600

601 GAGTTGCCTCGATGGTCTGCTTCTACGGAGTTCCTCTTCTGATTGTCAAC 650
    ||||||||||||||||||||||||||||||||||||||||||||||||||
601 GAGTTGCCTCGATGGTCTGCTTCTACGGAGTTCCTCTTCTGATTGTCAAC 650

651 GGGTTCTTAGTTTTGATCACTTACTTGCAGCACACGCATCCTTCCCTGCC 700
    ||||||||||||||||||||||||||||||||||||||||||||||||||
651 GGGTTCTTAGTTTTGATCACTTACTTGCAGCACACGCATCCTTCCCTGCC 700

701 TCACTATGACTCGTCTGAGTGGGATTGGTTGAGGGGAGCTTTGGCCACCG 750
    ||||||||||||||||||||||||||||||||||||||||||||||||||
701 TCACTATGACTCGTCTGAGTGGGATTGGTTGAGGGGAGCTTTGGCCACCG 750

751 TTGACAGAGACTACGGAATCTTGAACAAGGTCTTCCACAATATCACGGAC 800
    ||||||||||||||||||||||||||||||||||||||||||||||||||
751 TTGACAGAGACTACGGAATCTTGAACAAGGTCTTCCACAATATCACGGAC 800
         Reverse primer
801 ACGCACGTGGCGCATCACCTGTTCTCGACCATGCCGCATTATCATGCGAT 850
    ←——————————————————
    ||||||||||||||||||||||||||||||||||||||||||||||||||
801 ACGCACGTGGCGCATCACCTGTTCTCGACCATGCCGCATTATCATGCGAT 850

851 GGAAGCTACGAAGGCGATAAAGCCGATACTGGGAGAGTATTATCAGTTCG 900
    ||||||||||||||||||||||||||||||||||||||||||||||||||
851 GGAAGCTACGAAGGCGATAAAGCCGATACTGGGAGAGTATTATCAGTTCG 900

901 ATGGGACGCCGGTGGTTAAGGCGATGTGGAGGGAGGCGAAGGAGTGTATC 950
    ||||||||||||||||||||||||||||||||||||||||||||||||||
901 ATGGGACGCCGGTGGTTAAGGCGATGTGGAGGGAGGCGAAGGAGTGTATC 950

951 TATGTGGAACCGGACAGGGAAGGTGACAAGAAAGG 985
    |||||||||||||||||||||||||||||||||||
951 TATGTGGAACCGGACAGGGAAGGTGACAAGAAAGG 985

FIG. 1B

|          | 1          |            |            |            | 50         |
|----------|------------|------------|------------|------------|------------|
| DMS100   | ~~~~~~~~~~ | ~~~~~~~~~~ | ~~~~~~~~~~ | ~~~~~~~~~~ | ~~~~~~~~IP |
| Quantum  | ~~~~~~~~~~ | ~~~~~~~~~~ | ~~~~~~~~~~ | ~~~~~~~~~~ | ~~~~~~~~IP |
| Bnfad2   | MGAGGRMQVS | PPSKKSETDT | IKRVPCETPP | FTVGELKKAI | PPHCFKRSIP |

|          | 51         |            |            |            | 100        |
|----------|------------|------------|------------|------------|------------|
| DMS100   | RSFSYLIWDI | IIASCFYYVA | TTYFPLLPHP | LSYFAWPLYW | ACQGCVLTGV |
| Quantum  | RSFSYLIWDI | IIASCFYYVA | TTYFPLLPHP | LSYFAWPLYW | ACQGCVLTGV |
| Bnfad2   | RSFSYLIWDI | IIASCFYYVA | TTYFPLLPHP | LSYFAWPLYW | ACQGCVLTGV |

|          | 101        |            |            |            | 150        |
|----------|------------|------------|------------|------------|------------|
| DMS100   | WVIAHECGHH | AFSDYQWLDD | TVGLIFHSFL | LVPYFSWKYS | HRRHHSNTGS |
| Quantum  | WVIAHECGHH | AFSDYQWLDD | TVGLIFHSFL | LVPYFSWKYS | HRRHHSNTGS |
| Bnfad2   | WVIAHECGHH | AFSDYQWLDD | TVGLIFHSFL | LVPYFSWKYS | HRRHHSNTGS |

|          | 151        |            |            |     ▼      | 200        |
|----------|------------|------------|------------|------------|------------|
| DMS100   | LERDEVFVPK | KKSDIKWYGK | YLNNPLGRTV | MLTV*FTLGW | PLYLAFNVSG |
| Quantum  | LERDEVFVPK | KKSDIKWYGK | YLNNPLGRTV | MLTVQFTLGW | PLYLAFNVSG |
| BNfad2   | LERDEVFVPK | KKSDIKWYGK | YLNNPLGRTV | MLTVQFTLGW | PLYLAFNVSG |

|          | 201        |            |            |            | 250        |
|----------|------------|------------|------------|------------|------------|
| DMS100   | RPYDGGFACH | FHPNAPIYND | RERLQIYISD | AGILAVCYGL | YRYAAVQGVA |
| Quantum  | RPYDGGFACH | FHPNAPIYND | RERLQIYISD | AGILAVCYGL | YRYAAVQGVA |
| BNfad2   | RPYDGGFACH | FHPNAPIYND | RERLQIYISD | AGILAVCYGL | FRYAAAQGVA |

|          | 251        |            |            |            | 300        |
|----------|------------|------------|------------|------------|------------|
| DMS100   | SMVCFYGVPL | LIVNGFLVLI | TYLQHTHPSL | PHYDSSEWDW | LRGALATVDR |
| Quantum  | SMVCFYGVPL | LIVNGFLVLI | TYLQHTHPSL | PHYDSSEWDW | LRGALATVDR |
| BNfad2   | SMVCFYGVPL | LIVNGLLVLI | TYLQHTHPSL | PHYDSSEWDW | LRGALATVDR |

|          | 301        |            |            |            | 350        |
|----------|------------|------------|------------|------------|------------|
| DMS100   | DYGILNKVFH | NITDTHVAHH | LFSTMPHYHA | MEATKAIKPI | LGEYYQFDGT |
| Quantum  | DYGILNKVFH | NITDTHVAHH | LFSTMPHYHA | MEATKAIKPI | LGEYYQFDGT |
| BNfad2   | DYGILNKVFH | NITDTHVAHH | LFSTMPHYHA | MEATKAIKPI | LGEYYQFDGT |

|          | 351        |            | 384        |
|----------|------------|------------|------------|
| DMS100   | PVVKAMWREA | KECIYVEPDR | EGDKK~~~~~ ~~~~ |
| Quantum  | PVVKAMWREA | KECIYVEPDR | EGDKK~~~~~ ~~~~ |
| BNfad2   | PVVKAMWREA | KECIYVEPDR | QGEKKGVFWY NNKL |

FIG. 2

```
         Forward primer
    1  CAAGAATTTGTCCCACAGTACACGGATGCTCAGATACACTGTCCCTCTCC  50
       |||||||||||||||||||||||||||||||||||||||||||||||||||
    1  CAAGAATTTGTCCCACAGTACACGGATGCTCAGATACACTGTCCCTCTCC  50   Exon 4

51  CCATGCTCGCTTACCCTCTCTATCTGGTAAATCCTAATTCCTAATTTTTC  100
       |||||||||||||||||||||||||||||||||||||||||||||||||||
   51  CCATGCTCGCTTACCCTCTCTATCTGGTAAATCCTAATTCCTAATTTTTC  100

101  TTCCTGATTATAATTACAATTTTGAATTTTTAGATTTTGAGTATTAACTA  150
       |||||||||||||||||||||||||||||||||||||||||||||||||||
  101  TTCCTGATTATAATTACAATTTTGAATTTTTAGATTTTGAGTATTAACTA  150   Intron 4

151  AATATAAATTAAATTTGTTTGGGGATGACTACAGTGGTACAGAAGTCCTG  200
       |||||||||||||||||||||||||||||||||||||||||||||||||||
  151  AATATAAATTAAATTTGTTTGGGGATGACTACAGTGGTACAGAAGTCCTG  200

201  GTAAAGAAGGGTCACATTATAACCCATACAGTAGTTTATTTGCCCCAAGC  250
       |||||||||||||||||||||||||||||||||||||||||||||||||||
  201  GTAAAGAAGGGTCACATTATAACCCATACAGTAGTTTATTTGCCCCAAGC  250

251  GAGAGAAAGCTTATTGCAACTTCAACTACTTGCTGGTCGATCGTGTTGGC  300   Exon 5
       |||||||||||||||||||||||||||||||||||||||||||||||||||
  251  GAGAGAAAGCTTATTGCAACTTCAACTACTTGCTGGTCGATCGTGTTGGC  300

301  CACTCTTGTTTATCTATCATTCCTCGTTGGTCCAGTCACAGTTCTAAAAG  350
       |||||||||||||||||||||||||||||||||||||||||||||||||||
  301  CACTCTTGTTTATCTATCATTCCTCGTTGGTCCAGTCACAGTTCTAAAAG  350

351  TCTATGGTGTTCCTTACATTGTAAGTTTCATATATTTCTTTATTATATCA  400
       |||||||||||||||||||||||||||||||||||||||||||||||||||
  351  TCTATGGTGTTCCTTACATTGTAAGTTTCATATATTTCTTTATTATATCA  400   Intron 5

401  TTGCTAATATAATTTGTTTTTGACATAAAAGTTTTGGAAAAATTTCAGAT  450
       |||||||||||||||||||||||||||||||||||||||||||||||||||
  401  TTGCTAATATAATTTGTTTTTGACATAAAAGTTTTGGAAAAATTTCAGAT  450

451  CTTTGTAATGTGGTTGGACGCTGTCACGTACTTGCATCATCATGGTCACG  500
       |||||||||||||||||||||||||||||||||||||||||||||||||||
  451  CTTTGTAATGTGGTTGGACGCTGTCACGTACTTGCATCATCATGGTCACG  500   Exon 6

Reverse primer
  501  ATGATAAGCTGCCTTGGTACAGAGGCAAGATAAGTAGATCAACATTATTT  550
       |||||||||||||||||||||||||||||||||||||||||||||||||||
  501  ATGATAAGCTGCCTTGGTACAGAGGCAAGGTAAGTAGATCAACATTATTT  550

551  ATAAGAAGCAATAATGATTAGTAGTTGAATAATCTGAATTTTTGATGTTT  600
       |||||||||||||||||||||||||||||||||||||||||||||||||||
  551  ATAAGAAGCAATAATGATTAGTAGTTGAATAATCTGAATTTTTGATGTTT  600   Intron 6

601  TTGTACAATAATAGGAATGGAGTTATTTACGTGGAGGATTAACAACAGTT  650   Exon 7
       |||||||||||||||||||||||||||||||||||||||||||||||||||
  601  TTGTACAATAATAGGAATGGAGTTATTTACGTGGAGGATTAACAACAGTT  650

SEQUENCE LISTING

```
<160> NUMBER OF SEQ ID NOS: 39

<210> SEQ ID NO 1
<211> LENGTH: 985
<212> TYPE: DNA
<213> ORGANISM: Brassica napus

<400> SEQUENCE: 1
caatccctcg ctctttctcc tacctcatct gggacatcat catagcctcc tgcttctact      60
acgtcgccac cacttacttc cctctcctcc ctcaccctct ctcctacttc gcctggcctc     120
tctactgggc ctgccagggc tgcgtcctaa ccggcgtctg ggtcatagcc cacgagtgcg     180
gccaccacgc cttcagcgac taccagtggc tggacgacac cgtcggcctc atcttccact     240
```

```
ccttcctcct cgtcccttac ttctcctgga agtacagtca tcgacgccac cattccaaca    300
ctggctccct cgagagagac gaagtgtttg tccccaagaa gaagtcagac atcaagtggt    360
acggcaagta cctcaacaac cctttgggac gcaccgtgat gttaacggtt tagttcactc    420
tcggctggcc tttgtactta gccttcaacg tctcggggag accttacgac ggcggcttcg    480
cttgccattt ccaccccaac gctcccatct acaacgaccg tgagcgtctc cagatataca    540
tctccgacgc tggcatcctc gccgtctgct acggtctcta ccgctacgct gctgtccaag    600
gagttgcctc gatggtctgc ttctacgag ttcctcttct gattgtcaac gggttcttag     660
ttttgatcac ttacttgcag cacacgcatc cttccctgcc tcactatgac tcgtctgagt    720
gggattggtt gagggagct ttggccaccg ttgacagaga ctacggaatc ttgaacaagg     780
tcttccacaa tatcacggac acgcacgtgg cgcatcacct gttctcgacc atgccgcatt    840
atcatgcgat ggaagctacg aaggcgataa agccgatact gggagagtat tatcagttcg    900
atgggacgcc ggtggttaag gcgatgtgga gggaggcgaa ggagtgtatc tatgtggaac    960
cggacaggga aggtgacaag aaagg                                          985
```

<210> SEQ ID NO 2
<211> LENGTH: 985
<212> TYPE: DNA
<213> ORGANISM: Brassica napus

<400> SEQUENCE: 2

```
caatccctcg ctctttctcc tacctcatct gggacatcat catagcctcc tgcttctact     60
acgtcgccac cacttacttc cctctcctcc ctcaccctct ctcctacttc gcctggcctc    120
tctactgggc ctgccagggc tgcgtcctaa ccggcgtctg ggtcatagcc cacgagtgcg    180
gccaccacgc cttcagcgac taccagtggc tggacgacac cgtcggcctc atcttccact    240
ccttcctcct cgtcccttac ttctcctgga agtacagtca tcgacgccac cattccaaca    300
ctggctccct cgagagagac gaagtgtttg tccccaagaa gaagtcagac atcaagtggt    360
acggcaagta cctcaacaac cctttgggac gcaccgtgat gttaacggtt cagttcactc    420
tcggctggcc tttgtactta gccttcaacg tctcggggag accttacgac ggcggcttcg    480
cttgccattt ccaccccaac gctcccatct acaacgaccg tgagcgtctc cagatataca    540
tctccgacgc tggcatcctc gccgtctgct acggtctcta ccgctacgct gctgtccaag    600
gagttgcctc gatggtctgc ttctacgag ttcctcttct gattgtcaac gggttcttag     660
ttttgatcac ttacttgcag cacacgcatc cttccctgcc tcactatgac tcgtctgagt    720
gggattggtt gagggagct ttggccaccg ttgacagaga ctacggaatc ttgaacaagg     780
tcttccacaa tatcacggac acgcacgtgg cgcatcacct gttctcgacc atgccgcatt    840
atcatgcgat ggaagctacg aaggcgataa agccgatact gggagagtat tatcagttcg    900
atgggacgcc ggtggttaag gcgatgtgga gggaggcgaa ggagtgtatc tatgtggaac    960
cggacaggga aggtgacaag aaagg                                          985
```

<210> SEQ ID NO 3
<211> LENGTH: 651
<212> TYPE: DNA
<213> ORGANISM: Brassica napus

<400> SEQUENCE: 3

```
caagaatttg tcccacagta cacgdatgct cagatacact gtccctctcc ccatgctcgc     60
ttaccctctc tatctggtaa atcctaattc ctaattttc ttcctgatta taattacaat     120
```

-continued

```
tttgaatttt tagattttga gtattaacta aatataaatt aaatttgttt ggggatgact      180
acagtggtac agaagtcctg gtaaagaagg gtcacattat aacccataca gtagtttatt      240
tgccccaagc gagagaaagc ttattgcaac ttcaactact tgctggtcga tcgtgttggc      300
cactcttgtt tatctatcat tcctcgttgg tccagtcaca gttctaaaag tctatggtgt      360
tccttacatt gtaagtttca tatatttctt tattatatca ttgctaatat aatttgtttt      420
tgacataaaa gttttggaaa aatttcagat ctttgtaatg tggttggacg ctgtcacgta      480
cttgcatcat catggtcacg atgataagct gccttggtac agaggcaaga taagtagatc      540
aacattattt ataagaagca ataatgatta gtagttgaat aatctgaatt tttgatgttt      600
ttgtacaata ataggaatgg agttatttac gtggaggatt aacaacagtt g              651
```

<210> SEQ ID NO 4
<211> LENGTH: 651
<212> TYPE: DNA
<213> ORGANISM: Brassica napus

<400> SEQUENCE: 4

```
caagaatttg tcccacagta cacggatgct cagatacact gtccctctcc ccatgctcgc       60
ttaccctctc tatctggtaa atcctaattc ctaattttc ttcctgatta taattacaat      120
tttgaatttt tagattttga gtattaacta aatataaatt aaatttgttt ggggatgact      180
acagtggtac agaagtcctg gtaaagaagg gtcacattat aacccataca gtagtttatt      240
tgccccaagc gagagaaagc ttattgcaac ttcaactact tgctggtcga tcgtgttggc      300
cactcttgtt tatctatcat tcctcgttgg tccagtcaca gttctaaaag tctatggtgt      360
tccttacatt gtaagtttca tatatttctt tattatatca ttgctaatat aatttgtttt      420
tgacataaaa gttttggaaa aatttcagat ctttgtaatg tggttggacg ctgtcacgta      480
cttgcatcat catggtcacg atgataagct gccttggtac agaggcaagg taagtagatc      540
aacattattt ataagaagca ataatgatta gtagttgaat aatctgaatt tttgatgttt      600
ttgtacaata ataggaatgg agttatttac gtggaggatt aacaacagtt g              651
```

<210> SEQ ID NO 5
<211> LENGTH: 136
<212> TYPE: PRT
<213> ORGANISM: Brassica napus

<400> SEQUENCE: 5

```
Ile Pro Arg Ser Phe Ser Tyr Leu Ile Trp Asp Ile Ile Ala Ser
1               5                   10                  15

Cys Phe Tyr Tyr Val Ala Thr Thr Tyr Phe Pro Leu Leu Pro His Pro
                20                  25                  30

Leu Ser Tyr Phe Ala Trp Pro Leu Tyr Trp Ala Cys Gln Gly Cys Val
            35                  40                  45

Leu Thr Gly Val Trp Val Ile Ala His Glu Cys Gly His His Ala Phe
        50                  55                  60

Ser Asp Tyr Gln Trp Leu Asp Asp Thr Val Gly Leu Ile Phe His Ser
65                  70                  75                  80

Phe Leu Leu Val Pro Tyr Phe Ser Trp Lys Tyr Ser His Arg Arg His
                85                  90                  95

His Ser Asn Thr Gly Ser Leu Glu Arg Asp Glu Val Phe Val Pro Lys
                100                 105                 110

Lys Lys Ser Asp Ile Lys Trp Tyr Gly Lys Tyr Leu Asn Asn Pro Leu
            115                 120                 125
```

```
Gly Arg Thr Val Met Leu Thr Val
    130                 135
```

<210> SEQ ID NO 6
<211> LENGTH: 327
<212> TYPE: PRT
<213> ORGANISM: Brassica napus

<400> SEQUENCE: 6

```
Ile Pro Arg Ser Phe Ser Tyr Leu Ile Trp Asp Ile Ile Ala Ser
 1               5                  10                  15

Cys Phe Tyr Tyr Val Ala Thr Thr Tyr Phe Pro Leu Leu Pro His Pro
                20                  25                  30

Leu Ser Tyr Phe Ala Trp Pro Leu Tyr Trp Ala Cys Gln Gly Cys Val
            35                  40                  45

Leu Thr Gly Val Trp Val Ile Ala His Glu Cys Gly His His Ala Phe
        50                  55                  60

Ser Asp Tyr Gln Trp Leu Asp Asp Thr Val Gly Leu Ile Phe His Ser
65                  70                  75                  80

Phe Leu Leu Val Pro Tyr Phe Ser Trp Lys Tyr Ser His Arg Arg His
                85                  90                  95

His Ser Asn Thr Gly Ser Leu Glu Arg Asp Glu Val Phe Val Pro Lys
            100                 105                 110

Lys Lys Ser Asp Ile Lys Trp Tyr Gly Lys Tyr Leu Asn Asn Pro Leu
        115                 120                 125

Gly Arg Thr Val Met Leu Thr Val Gln Phe Thr Leu Gly Trp Pro Leu
    130                 135                 140

Tyr Leu Ala Phe Asn Val Ser Gly Arg Pro Tyr Asp Gly Gly Phe Ala
145                 150                 155                 160

Cys His Phe His Pro Asn Ala Pro Ile Tyr Asn Asp Arg Glu Arg Leu
                165                 170                 175

Gln Ile Tyr Ile Ser Asp Ala Gly Ile Leu Ala Val Cys Tyr Gly Leu
            180                 185                 190

Tyr Arg Tyr Ala Ala Val Gln Gly Val Ala Ser Met Val Cys Phe Tyr
        195                 200                 205

Gly Val Pro Leu Leu Ile Val Asn Gly Phe Leu Val Leu Ile Thr Tyr
    210                 215                 220

Leu Gln His Thr His Pro Ser Leu Pro His Tyr Asp Ser Ser Glu Trp
225                 230                 235                 240

Asp Trp Leu Arg Gly Ala Leu Ala Thr Val Asp Arg Asp Tyr Gly Ile
                245                 250                 255

Leu Asn Lys Val Phe His Asn Ile Thr Asp Thr His Val Ala His His
            260                 265                 270

Leu Phe Ser Thr Met Pro His Tyr His Ala Met Glu Ala Thr Lys Ala
        275                 280                 285

Ile Lys Pro Ile Leu Gly Glu Tyr Tyr Gln Phe Asp Gly Thr Pro Val
    290                 295                 300

Val Lys Ala Met Trp Arg Glu Ala Lys Glu Cys Ile Tyr Val Glu Pro
305                 310                 315                 320

Asp Arg Glu Gly Asp Lys Lys
                325
```

<210> SEQ ID NO 7
<211> LENGTH: 384
<212> TYPE: PRT
<213> ORGANISM: Brassica napus

<400> SEQUENCE: 7

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Leu Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380
```

<210> SEQ ID NO 8
<211> LENGTH: 1106
<212> TYPE: DNA
<213> ORGANISM: Brassica napus

<400> SEQUENCE: 8

```
gtctgaaacc gacaacatca agcgcgtacc ctgcgagaca ccgcccttca ctgtcggaga    60
actcaagaaa gcaatcccac cgcactgttt caaacgctcg atccctcgct ctttctccta   120
cctcatctgg gacatcatca tagcctcctg cttctactac gtcgccacca ttacttccct   180
ctcctccctc accctctctc ctacttcgcc tggcctctct actgggcctg ccagggctgc   240
gtcctaaccg gcgtctgggt catagcccac gagtgcggcc accacgcctt cagcgactac   300
cagtggctgg acgacaccgt cggcctcatc ttccactcct cctcctcgt cccttacttc    360
tcctggaagt acagtcatcg acgccaccat tccaacactg gctccctcga gagagacgaa   420
gtgtttgtcc caagaagaa gtcagacatc aagtggtacg gcaagtacct caacaaccct    480
ttgggacgca ccgtgatgtt aacggttcag ttcactctcg gctggccttt gtacttagcc   540
ttcaacgtct cggggagacc ttacgacggc ggcttcgctt gccatttcca ccccaacgct   600
cccatctaca acgaccgtga gcgtctccag atatacatct ccgacgctgg catcctcgcc   660
gtctgctacg gtctctaccg ctacgctgct gtccaaggag ttgcctcgat ggtctgcttc   720
tacgagttc ctcttctgat tgtcaacggg ttcttagttt tgatcactta cttgcagcac    780
acgcatcctt ccctgcctca ctatgactcg tctgagtggg attggttgag gggagctttg   840
gccaccgttg acagagacta cggaatcttg aacaaggtct tccacaatat cacgacacg    900
cacgtggcgc atcacctgtt ctcgaccatg ccgcattatc atgcgatgga agctacgaag   960
gcgataaagc cgatactggg agagtattat cagttcgatg ggacgccggt ggttaaggcg  1020
atgtggaggg aggcgaagga gtgtatctat gtggaaccgg acaggcaagg tgagaagaaa  1080
ggtgtgttct ggtacaacaa taagat                                      1106
```

<210> SEQ ID NO 9
<211> LENGTH: 81
<212> TYPE: PRT
<213> ORGANISM: Brassica napus

<400> SEQUENCE: 9

```
Ser Glu Thr Asp Asn Ile Lys Arg Val Pro Cys Glu Thr Pro Pro Phe
  1               5                  10                  15
Thr Val Gly Glu Leu Lys Lys Ala Ile Pro Pro His Cys Phe Lys Arg
             20                  25                  30
Ser Ile Pro Arg Ser Phe Ser Tyr Leu Ile Trp Asp Ile Ile Ile Ala
         35                  40                  45
Ser Cys Phe Tyr Tyr Val Ala Thr Ile Thr Ser Leu Ser Ser Leu Thr
     50                  55                  60
Leu Ser Pro Thr Ser Pro Gly Leu Ser Thr Gly Pro Ala Arg Ala Ala
 65                  70                  75                  80
Ser
```

<210> SEQ ID NO 10
<211> LENGTH: 1155
<212> TYPE: DNA
<213> ORGANISM: Brassica napus

<400> SEQUENCE: 10

```
atgggtgcag gtggaagaat gcaagtgtct cctccctcca aaaagtctga aaccgacaac    60
atcaagcgcg tacctgcga gacaccgccc ttcactgtcg agaactcaa gaaagcaatc    120
ccaccgcact gtttcaaacg ctcgatccct cgctctttct cctacctcat ctgggacatc   180
```

-continued

```
atcatagcct cctgcttcta ctacgtcgcc accacttact tccctctcct ccctcaccct    240
ctctcctact tcgcctggcc tctctactgg gcctgccagg gctgcgtcct aaccggcgtc    300
tgggtcatag cccacgagtg cggccaccac gccttcagcg actaccagtg gctggacgac    360
accgtcggcc tcatcttcca ctccttcctc ctcgtccctt acttctcctg gaagtacagt    420
catcgacgcc accattccaa cactggctcc ctcgagagag acgaagtgtt tgtccccaag    480
aagaagtcag acatcaagtg gtacggcaag tacctcaaca ccctttggg acgcaccgtg     540 atgttaacgg ttcagttcac tctcggctgg cctttgtact tagccttcaa cgtctcgggg    600 agacctacg acggcggctt cgcttgccat ttccacccca acgctcccat ctacaacgac     660
cgtgagcgtc tccagatata catctccgac gctggcatcc tcgccgtctg ctacggtctc    720
taccgctacg ctgctgtcca aggagttgcc tcgatggtct gcttctacgg agttcctctt    780
ctgattgtca acgggttctt agttttgatc acttacttgc agcacacgca tccttccctg    840
cctcactatg actcgtctga gtgggattgg ttgaggggag cttttggcca cgttgacaga    900
gactacggaa tcttgaacaa ggtcttccac aatatcacgg acacgcacgt ggcgcatcac    960
ctgttctcga ccatgccgca ttatcacgcg atggaagcta cgaaggcgat aaagccgata    1020
ctgggagagt attatcagtt cgatgggacg ccggtggtta aggcgatgtg gagggaggcg    1080
aaggagtgta tctatgtgga accggacagg caaggtgaga agaaaggtgt gttctggtac    1140
aacaataagt tatga                                                    1155
```

<210> SEQ ID NO 11
<211> LENGTH: 384
<212> TYPE: PRT
<213> ORGANISM: Brassica napus

<400> SEQUENCE: 11

```
Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205
```

```
Cys His Phe His Pro Asn Ala Pro Ile Tyr Asn Asp Arg Glu Arg Leu
        210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
370                 375                 380

<210> SEQ ID NO 12
<211> LENGTH: 1154
<212> TYPE: DNA
<213> ORGANISM: Brassica napus

<400> SEQUENCE: 12
atgggtgcag gtggaagaat gcaagtgtct cctccctcca aaaagtctga aaccgacaac        60
atcaagcgcg taccctgcga gacaccgccc ttcactgtcg agaactcaa  gaaagcaatc       120 ccaccgcact gtttcaaacg ctcgatccct cgctcttttct cctacctcat ctgggacatc      180
atcatagcct cctgcttcta ctacgtcgcc accattactt ccctctcctc cctcacccct       240
tctcctactt cgcctggcct ctctactggg cctgccaggg ctgcgtccta accggcgtct       300
gggtcatagc ccacgagtgc ggccaccacg ccttcagcga ctaccagtgg ctggacgaca       360
ccgtcggcct catcttccac tccttcctcc tcgtccctta cttctcctgg aagtacagtc       420
atcgacgcca ccattccaac actggctccc tcgagagaga cgaagtgttt gtccccaaga       480
agaagtcaga catcaagtgg tacggcaagt acctcaacaa cccctttggga cgcaccgtga      540 tgttaacggt tcagttcact ctcggctggc ctttgtactt agccttcaac gtctcgggga       600
gaccttacga cggcggcttc gcttgccatt ccaccccaa cgctcccatc tacaacgacc        660
gtgagcgtct ccagatatac atctccgacg ctggcatcct cgccgtctgc tacggtctct       720
accgctacgc tgctgtccaa ggagttgcct cgatggtctg cttctacgga gttcctcttc       780
tgattgtcaa cggttcttta gttttgatca cttacttgca gcacacgcat ccttccctgc       840
ctcactatga ctcgtctgag tgggattggt tgaggggagc tttggccacc gttgacagag       900
actacggaat cttgaacaag gtcttccaca atatcacgga cacgcacgtg gcgcatcacc       960
tgttctcgac catgccgcat tatcacgcga tggaagctac gaaggcgata aagccgatac      1020
tgggagagta ttatcagttc gatgggacgc cggtggttaa ggcgatgtgg agggaggcga     1080
aggagtgtat ctatgtggaa ccggacaggc aaggtgagaa gaaggtgtg ttctggtaca      1140
```

```
acaataagtt atga                                                     1154
```

<210> SEQ ID NO 13
<211> LENGTH: 96
<212> TYPE: PRT
<213> ORGANISM: Brassica napus

<400> SEQUENCE: 13

```
Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Ile Thr Ser Leu Ser Ser Leu Thr Leu
65                  70                  75                  80

Ser Pro Thr Ser Pro Gly Leu Ser Thr Gly Pro Ala Arg Ala Ala Ser
                85                  90                  95
```

<210> SEQ ID NO 14
<211> LENGTH: 1155
<212> TYPE: DNA
<213> ORGANISM: Brassica napus

<400> SEQUENCE: 14

```
atgggtgcag gtggaagaat gcaagtgtct cctccctcca agaagtctga aaccgacacc      60
atcaagcgcg taccctgcga gacaccgccc ttcactgtcg gagaactcaa gaaagcaatc     120
ccaccgcact gtttcaaacg ctcgatccct cgctctttct cctacctcat ctgggacatc     180
atcatagcct cctgcttcta ctacgtcgcc accacttact ccctctcctc ccctcaccct     240
ctctcctact cgcctggcc tctctactgg gcctgccaag ggtgcgtcct aaccggcgtc      300
tgggtcatag cccacgagtg cggccaccac gccttcagcg actaccagtg gcttgacgac     360
accgtcggtc tcatcttcca ctccttcctc ctcgtccctt acttctcctg gaagtacagt     420
catcgacgcc accattccaa cactggctcc ctcgagagag acgaagtgtt tgtccccaag     480
aagaagtcag acatcaagtg gtacggcaag tacctcaaca ccctttggg acgcaccgtg      540
atgttaacgg ttcagttcac tctcggctgg ccgttgtact tagccttcaa cgtctcggga     600
agaccttacg acgcggctt cgcttgccat ttccacccca acgctcccat ctacaacgac     660
cgcgagcgtc tccagatata catctccgac gctggcatcc tcgccgtctg ctacggtctc     720
ttccgttacg ccgccgcgca gggagtggcc tcgatggtct gcttctacgg agtcccgctt     780
ctgattgtca atggtttcct cgtgttgatc acttacttgc agcacacgca tccttccctg     840
cctcactacg attcgtccga gtgggattgg ttgaggggag cttttggctac cgttgacaga    900
gactacggaa tcttgaacaa ggtcttccac aatattaccg acacgcacgt ggcgcatcat    960
ctgttctcca cgatgccgca ttatcacgcg atggaagcta ccaaggcgat aaagccgata  1020
ctgggagagt attatcagtt cgatgggacg ccggtggtta aggcgatgtg gagggaggcg   1080
aaggagtgta tctatgtgga accggacagg caaggtgaga agaaaggtgt gttctggtac   1140
aacaataagt tatga                                                   1155
```

<210> SEQ ID NO 15
<211> LENGTH: 384
<212> TYPE: PRT

<213> ORGANISM: Brassica napus

<400> SEQUENCE: 15

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
370                 375                 380
```

<210> SEQ ID NO 16
<211> LENGTH: 1155
<212> TYPE: DNA

<213> ORGANISM: Brassica napus

<400> SEQUENCE: 16

```
atgggtgcag gtggaagaat gcaagtgtct cctccctcca agaagtctga aaccgacacc    60
atcaagcgcg taccctgcga gacaccgccc ttcactgtcg gagaactcaa gaaagcaatc   120
ccaccgcact gtttcaaacg ctcgatccct cgctctttct cctacctcat ctgggacatc   180
atcatagcct cctgcttcta ctacgtcgcc accacttact ccctctcct ccctcaccct    240
ctctcctact cgcctggcc tctctactgg gcctgccaag ggtgcgtcct aaccggcgtc   300
tgggtcatag cccacgagtg cggccaccac gccttcagcg actaccagtg gtttgacgac   360
accgtcggtc tcatcttcca ctccttcctc ctcgtccctt acttctcctg aagtacagt    420
catcgacgcc accattccaa cactggctcc ctcgagagag acgaagtgtt tgtccccaag   480
aagaagtcag acatcaagtg gtacggcaag tacctcaaca ccctttggg acgcaccgtg    540
atgttaacgg ttcagttcac tctcggctgg ccgttgtact tagccttcaa cgtctcggga   600
agaccttacg acggcggctt cgcttgccat ttccacccca cgctcccat ctacaacgac    660
cgcgagcgtc tccagatata catctccgac gctggcatcc tcgccgtctg ctacggtctc   720
ttccgttacg ccgccgcgca gggagtggcc tcgatggtct gcttctacgg agtcccgctt   780
ctgattgtca atggtttcct cgtgttgatc acttacttgc agcacacgca tccttccctg   840
cctcactacg attcgtccga gtgggattgg ttgaggggag ctttggctac cgttgacaga   900
gactacggaa tcttgaacaa ggtcttccac aatattaccg acacgcacgt ggcgcatcat   960
ctgttctcca cgatgccgca ttatcacgcg atggaagcta ccaaggcgat aaagccgata  1020
ctgggagagt attatcagtt cgatgggacg ccggtggtta aggcgatgtg agggaggcg   1080
aaggagtgta tctatgtgga accggacagg caaggtgaga agaaaggtgt gttctggtac  1140
aacaataagt tatga                                                  1155
```

<210> SEQ ID NO 17
<211> LENGTH: 384
<212> TYPE: PRT
<213> ORGANISM: Brassica napus

<400> SEQUENCE: 17

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Phe Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
```

```
            145                 150                 155                 160
Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
                195                 200                 205

Cys His Phe His Pro Asn Ala Pro Ile Tyr Asn Asp Arg Glu Arg Leu
                210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
                275                 280                 285

Asp Trp Leu Arg Gly Ala Leu Ala Thr Val Asp Arg Asp Tyr Gly Ile
                290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
                370                 375                 380

<210> SEQ ID NO 18
<211> LENGTH: 2601
<212> TYPE: DNA
<213> ORGANISM: Brassica napus

<400> SEQUENCE: 18
agagagagaa gagaggagac agagagagag tttgaggagg agcttcttcg tagggttcat        60
cgttattaac gttaaatctt catccccccc tacgtcagcc agctcaaggt cccctttcttc      120 ttccatttct tctcatttta cgttgttttc aatcttggtc tgttcttttc ttatcgcttt      180
tctgttctat ctatcatttt tgcatttcag tcgatttaat tctagatctg ttaatattta      240
ttgcattaaa ctatagatct ggtcttgatt ctctgttttc atgtgtgaaa tcttgatgct      300
gtctttacca ttaatctgat tatattgtct ataccgtgga gaatatgaaa tgttgcattt      360
tcatttgtcc gaatacaaac tgtttgactt tcaatctttt ttaatgattt attttgatgg      420
gttggtggag ttgaaaaatc accatagcag tctcacgtcc tggtcttaga aatatccttc      480
ctattcaaag ttatatatat ttgtttactt gtcttagatc tggacctgag acatgtaagt      540
acctatttgt tgaatctttg ggtaaaaaac ttatgtctct gggtaaaatt tgcttggaga      600
tttgaccgat tcctattggc tcttgattct gtagttacct aatacatgaa aaagtttcat      660
ttggcctatg ctcacttcat gcttacaaac ttttctttgc aaattaattg gattagatgc      720
tccttcatag attcagatgc aatagatttg catgaagaaa ataataggat tcatgacagt      780
aaaaaagatt gtattttgt tgtttgtttt atgttttaaaa gtctatatgt tgacaataga      840
```

-continued

```
gttgctctca actgtttcat ttagctttt gttttgtca agttgcttat tcttagagac      900
attgtgatta tgacttgtct tctctaacgt agtttagtaa taaaagacga aagaaattga      960
tatccacaag aaagagatgt aagctgtaac gtatcaaatc tcattaataa ctagtagtat     1020
tctcaacgct atcgtttatt tctttctttg gtttgccact atatgccgct ctctgctct     1080
ttatcccacg tactatccat ttttttttgtg gtagtccatt tttttgaaac tttaataacg     1140
taacactgaa tattaatttg ttggtttaat taactttgag tctttgcttt tggtttatgc     1200
agaaacatgg gtgcaggtgg aagaatgcaa gtgtctcctc cctccaaaaa gtctgaaacc     1260
gacaacatca agcgcgtacc ctgcgagaca ccgcccttca ctgtcggaga actcaagaaa     1320
gcaatcccac cgcactgttt caaacgctcg atccctcgct ctttctccta cctcatctgg     1380
gacatcatca tagcctcctg cttctactac gtcgccacca cttactttccc tctcctccct     1440
caccctctct cctacttcgc ctggcctctc tactgggcct gccagggctg cgtcctaacc     1500
ggcgtctggg tcatagccca cgagtgcggc caccacgcct tcagcgacta ccagtggctg     1560
gacgacaccg tcggcctcat cttccactcc ttcctcctcg tcccttactt ctcctggaag     1620
tacagtcatc gacgccacca ttccaacact ggctccctcg agagagacga agtgtttgtc     1680
cccaagaaga agtcagacat caagtggtac ggcaagtacc tcaacaaccc tttgggacgc     1740
accgtgatgt taacggttca gttcactctc ggctggcctt tgtacttagc cttcaacgtc     1800
tcggggagac cttacgacgg cggcttcgct tgccatttcc accccaacgc tcccatctac     1860
aacgaccgtg agcgtctcca gatatacatc tccgacgctg gcatcctcgc cgtctgctac     1920
ggtctctacc gctacgctgc tgtccaagga gttgcctcga tggtctgctt ctacggagtt     1980
cctcttctga ttgtcaacgg gttcttagtt ttgatcactt acttgcagca cacgcatcct     2040
tccctgcctc actatgactc gtctgagtgg gattggttga ggggagcttt ggccaccgtt     2100
gacagagact acggaatctt gaacaaggtc ttccacaata tcacggacac gcacgtggcg     2160
catcacctgt tctcgaccat gccgcattat cacgcgatgg aagctacgaa ggcgataaag     2220
ccgatactgg gagagtatta tcagttcgat gggacgccgg tggttaaggc gatgtggagg     2280
gaggcgaagg agtgtatcta tgtggaaccg gacaggcaag gtgagaagaa aggtgtgttc     2340
tggtacaaca ataagttatg aagcaaagaa gaaactgaac cttctctctc tatgattgtc     2400
tttgtttaag aagctatgtt tctgtttcaa taatcttaat tatccatttt gttgtgtttt     2460
ctgacatttt ggctaaaatt atgtgatgtt ggaagttagt gtctaaaatg tcttgtgtct     2520
gtattgttct tcttctcatc gctgttatgt ttgggatcgt tgaaatgtga ctttcggact     2580
agtgaatctt gttctcgaac t                                                2601
```

<210> SEQ ID NO 19
<211> LENGTH: 2666
<212> TYPE: DNA
<213> ORGANISM: Brassica napus
<400> SEQUENCE: 19

```
gagaagagag agagagagag agagagagag agtgagtttg aggaggagct tcttcgtagg       60
gttcatcgtt attaacgtta aatcttcacc ccctacgtca gccagctcaa ggtcccttc      120
ttcttccatt tcttttcatt ctacgttgtt ttcaatctta tgaaactttc tggtctgtgc      180
ttttcttatc gcttttctat tctatctatc attttttgcat ttcagtcgat ttaattctag      240
atctgttaat attaaactat agatctgttc ttgattctct gttttcatgt gtgaaatctg      300
atgctgtatt aatctgatta tattgtctat accgtggaga atatcaaatg ttgcattttc      360
```

```
atttgtccga atacaaagtg tttgactttc aatcgttttt aattatatat atatatatat      420
tttttgatgg gttggtggag ttgaaaaatc accatagcag tctcacgtcc tggttttaga      480
aatatcctat tcaaaattat atatttgttt acttgtttta gatctggacc tgagacatat      540
aagtacctat ttgttgaatc tttgggtaaa aacttatgtc tctgggtaaa atttgctggg      600
agatttgacc gattcctatt ggctcttgat tctgtagtta cgtaatacat gaaaaagttt      660
catttggcct atgctcactt catgcttata aacgttttct tgcaaattaa ttggattaga      720
tgttatttca tagattcagt cattcagata caatggagtt gcatgaagaa aataatagaa      780
ttcgtgacag taaaaagat tgtatttttg tttgtttgtt tatgtttaaa agtctatatg       840
ttgacaatag agttgctctc aactgtttca tttagcttct ttttttgtca agttgcttat      900
tcttagagac attgtgatta tgacttgtct tctttaacgt agtttagtaa taaaagacga      960
aagaaattga tatccacaag aaagagatgt gagctgtagc gtatcaaatc tcgttcattt     1020
actagtagta ttctcaacgc tatcgtttat ttattttcct ttcgttggtt tgccactata     1080
tgccacttct ctcctctttg tcccacgtac tatccatttt ttttgtggta gtccattttc     1140
ttgtaactta taataacgta actctgaatc ttttgtctgt agattaattt gttggtttaa     1200
ttaactttta agtctttgct tttggcttat gcagaaacat gggtgcaggt ggaagaatgc     1260
aagtgtctcc tccctccaag aagtctgaaa ccgacaccat caagcgcgta ccctgcgaga     1320
caccgccctt cactgtcgga gaactcaaga aagcaatccc accgcactgt ttcaaacgct     1380
cgatccctcg ctcttttctcc tacctcatct gggacatcat catagcctcc tgcttctact     1440
acgtcgccac cacttacttc cctctcctcc ctcaccctct ctcctacttc gcctggcctc     1500
tctactgggc ctgccaaggg tgcgtcctaa ccggcgtctg ggtcatagcc cacgagtgcg     1560
gccaccacgc cttcagcgac taccagtggc ttgacgacac cgtcggtctc atcttccact     1620
ccttcctcct cgtcccttac ttctcctgga agtacagtca tcgacgccac cattccaaca     1680
ctggctccct cgagagagac gaagtgtttg tccccaagaa gaagtcagac atcaagtggt     1740
acggcaagta cctcaacaac cctttgggac gcaccgtgat gttaacggtt cagttcactc     1800
tcggctggcc gttgtactta gccttcaacg tctcggaag accttacgac ggcggcttcg      1860
cttgccattt ccaccccaac gctcccatct acaacgaccg cgagcgtctc cagatataca     1920
tctccgacgc tggcatcctc gccgtctgct acggtctctt ccgttacgcc gccgcgcagg     1980
gagtggcctc gatggtctgc ttctacggag tcccgcttct gattgtcaat ggtttcctcg     2040
tgttgatcac ttacttgcag cacacgcatc cttccctgcc tcactacgat tcgtccgagt     2100
gggattggtt gaggggagct ttggctaccg ttgacagaga ctacggaatc ttgaacaagg     2160
tcttccacaa tattaccgac acgcacgtgg cgcatcatct gttctccacg atgccgcatt     2220
atcacgcgat ggaagctacc aaggcgataa agccgatact gggagagtat tatcagttcg     2280
atgggacgcc ggtggttaag gcgatgtgga gggaggcgaa ggagtgtatc tatgtggaac     2340
cggacaggca aggtgagaag aaaggtgtgt tctggtacaa caataagtta tgaggatatg     2400
atgatggtga aagaacaaag aagatattgt cacgaacctt tctcttgctg tctctggtcg     2460
tctttgtttt aagaagctat gttttcgttt caataatctt aactatccat tttgttgtgt     2520
tttctgacat tttggctaaa attatgtgat gttggaagtt agtgtctaaa atgtcttgtg     2580
tctgtattgt tcttcttctc atcgctgtta tgtttgggat cgttgaaatg tgactttcgg     2640
actagtgaac tcttggttct cgaact                                          2666
```

<210> SEQ ID NO 20

```
<211> LENGTH: 1561
<212> TYPE: DNA
<213> ORGANISM: Brassica napus

<400> SEQUENCE: 20
gagaaccaga gagattcatt accaaagaga tagagagaga gagaaagaga ggagacagag      60
agagagtttg aggaggagct tcttcgtagg gttcatcgtt attaacgtta aatcttcatc     120
cccccctacg tcagccagct caagaaacat gggtgcaggt ggaagaatgc aagtgtctcc     180
tccctccaaa aagtctgaaa ccgacaacat caagcgcgta ccctgcgaga caccgccctt     240
cactgtcgga gaactcaaga aagcaatccc accgcactgt ttcaaacgct cgatccctcg     300
ctctttctcc tacctcatct gggacatcat catagcctcc tgcttctact acgtcgccac     360
cacttacttc cctctcctcc ctcaccctct ctcctacttc gcctggcctc tctactgggc     420
ctgccagggc tgcgtcctaa ccggcgtctg ggtcatagcc cacgagtgcg ccaccacgc      480 cttcagcgac taccagtggc tggacgacac cgtcggcctc atcttccact ccttcctcct     540
cgtcccttac ttctcctgga agtacagtca tcgacgccac cattccaaca ctggctccct     600
cgagagagac gaagtgtttg tccccaagaa gaagtcagac atcaagtggt acggcaagta     660
cctcaacaac cctttgggac gcaccgtgat gttaacggtt cagttcactc tcggctggcc     720
tttgtactta gccttcaacg tctcggggag accttacgac ggcggcttcg cttgccattt     780
ccaccccaac gctcccatct acaacgaccg tgagcgtctc cagatataca tctccgacgc     840
tggcatcctc gccgtctgct acggtctcta ccgctacgct gctgtccaag agttgcctc      900 gatggtctgc ttctacggag ttcctcttct gattgtcaac gggttcttag ttttgatcac     960
ttacttgcag cacacgcatc cttccctgcc tcactgatga ctcgtctgagt gggattggtt    1020 gaggggagct ttggccaccg ttgacagaga ctacggaatc ttgaacaagg tcttccacaa    1080
tatcacggac acgcacgtgg cgcatcacct gttctcgacc atgccgcatt atcatgcgat    1140
ggaagctacg aaggcgataa agccgatact gggagagtat tatcagttcg atgggacgcc    1200
ggtggttaag gcgatgtgga gggaggcgaa ggagtgtatc tatgtggaac cggacaggca    1260
aggtgagaag aaaggtgtgt tctggtacaa caataagtta tgaagcaaag aagaaactga    1320
acctttctcw tcctatgatt gtctttgttt aagaagctat gtttctgttt caataatctt    1380
taattatcca ttttgttgtg ttttctgaca ttttggctaa aattatgtga tgttggaagt    1440
tagtgtctaa aatgtcttgt gtctgtattg ttcttcttct catcgctgtt atgtttggga    1500
tcgttgaaat gtgactttcg gactagtgaa ctcttgttct cgaactaaaa aaaaaaaaa     1560 a                                                                    1561

<210> SEQ ID NO 21
<211> LENGTH: 1553
<212> TYPE: DNA
<213> ORGANISM: Brassica napus

<400> SEQUENCE: 21
gagacagatt cattaccaaa gagatagaga aagagagaga gagagagaga gagagagagt      60
gagtttgagg aggagcttct tcgtagggtt catcgttatt aacgttaaat cttcaccccc     120
tacgtcagcc agctcaagaa acatgggtgc aggtggaaga atgcaagtgt ctcctccctc     180
caagaagtct gaaaccgaca ccatcaagcg cgtaccctgc gagacaccgc cttcactgt     240 cggagaactc aagaaagcaa tcccaccgca ctgtttcaaa cgctcgatcc ctcgctcttt     300
ctcctacctc atctgggaca tcatcatagc ctcctgcttc tactacgtcg ccaccactta     360
```

| | |
|---|---|
| cttccctctc ctccctcacc ctctctccta cttcgcctgg cctctctact gggcctgcca | 420 |
| agggtgcgtc ctaaccggcg tctgggtcat agcccacgag tgcggccacc acgccttcag | 480 |
| cgactaccag tggcttgacg acaccgtcgg tctcatcttc cactccttcc tcctcgtccc | 540 |
| ttacttctcc tggaagtaca gtcatcgacg ccaccattcc aacactggct ccctcgagag | 600 |
| agacgaagtg tttgtcccca agaagaagtc agacatcaag tggtacggca agtacctcaa | 660 |
| caacccttg ggacgcaccg tgatgttaac ggttcagttc actctcggct ggccgttgta | 720 |
| cttagccttc aacgtctcgg gaagaccctta cgacggcggc ttcgcttgcc atttccaccc | 780 |
| caacgctccc atctacaacg accgcgagcg tctccagata tacatctccg acgctggcat | 840 |
| cctcgccgtc tgctacggtc tcttccgtta cgccgccgss cagggagtgg cctcgatggt | 900 |
| ctgcttctac ggagtcccgc ttctgattgt caatggtttc ctcgtgttga tcacttactt | 960 |
| gcagcacacg catccttccc tgcctcacta cgattcgtcc gagtgggatt ggttsagggg | 1020 |
| agctttggct accgttgaca gagactacgg aatcttgaac aaggtcttcc acaatattac | 1080 |
| cgacacgcac gtggcscatc atcygttctc cacgatgccg cattatcacg cgatggaagc | 1140 |
| taccaaggcg ataaagccga tactgggaga gtattatcag ttcgatggga cgccggtggt | 1200 |
| taaggcgatg tggagggagg cgaaggagtg tatctatgtg gaaccggaca ggcaaggtga | 1260 |
| gaagaaaggt gtgttctggt acaacaataa gttatgagga trraagaaac tgaacctttc | 1320 |
| tcttcctatg attgtctttg tttaagaagc tatgtttctg tttcaataat cttaattatc | 1380 |
| cattttgttg tgttttctga cattttggct aaaattatgt gatgttggaa gttagtgtct | 1440 |
| aaaatgtctt gtgtctgtat tgttcttctt ctcatcgctg ttatgtttgg gatcgttgaa | 1500 |
| atgtgacttt cggactagtg aactcttgtt ctcgaactaa aaaaaaaaaa aaa | 1553 |

<210> SEQ ID NO 22
<211> LENGTH: 1155
<212> TYPE: DNA
<213> ORGANISM: Brassica napus

<400> SEQUENCE: 22

| | |
|---|---|
| atgggtgcag gtggaagaat gcaagtgtct cctccctcca aaaagtctga aaccgacaac | 60 |
| atcaagcgcg taccctgcga gacaccgccc ttcactgtcg gagaactcaa gaaagcaatc | 120 |
| ccaccgcact gtttcaaacg ctcgatccct cgctctttct cctacctcat ctgggacatc | 180 |
| atcatagcct cctgcttcta ctacgtcgcc accacttact tccctctcct ccctcaccct | 240 |
| ctctcctact tcgcctggcc tctctactgg gcctgccagg gctgcgtcct aaccggcgtc | 300 |
| tgggtcatag cccacaagtg cggccaccac gccttcagcg actaccagtg gctggacgac | 360 |
| accgtcggcc tcatcttcca ctccttcctc ctcgtccctt acttctcctg gaagtacagt | 420 |
| catcgacgcc accattccaa cactggctcc tcgagagag acgaagtgtt tgtccccaag | 480 |
| aagaagtcag acatcaagtg gtacggcaag tacctcaaca ccctttggg acgcaccgtg | 540 |
| atgttaacgg ttcagttcac tctcggctgg cctttgtact tagccttcaa cgtctcgggg | 600 |
| agaccttacg acgcggctt cgcttgccat ttccacccca cgctcccat ctacaacgac | 660 |
| cgtgagcgtc tccagatata catctccgac gctggcatcc tcgccgtctg ctacggtctc | 720 |
| taccgctacg ctgctgtcca aggagttgcc tcgatggtct gcttctacgg agttcctctt | 780 |
| ctgattgtca acgggttctt agttttgatc acttacttgc agcacacgca tccttccctg | 840 |
| cctcactatg actcgtctga gtgggattgg ttgaggggag ctttggccac cgttgacaga | 900 |
| gactacggaa tcttgaacaa ggtcttccac aatatcacgg acacgcacgt ggcgcatcac | 960 |

-continued

```
ctgttctcga ccatgccgca ttatcatgcg atggaagcta cgaaggcgat aaagccgata    1020
ctgggagagt attatcagtt cgatgggacg ccggtggtta aggcgatgtg gagggaggcg    1080
aaggagtgta tctatgtgga accggacagg caaggtgaga gaaaggtgt gttctggtac     1140 aacaataagt tatga                                                      1155
```

<210> SEQ ID NO 23
<211> LENGTH: 384
<212> TYPE: PRT
<213> ORGANISM: Brassica napus

<400> SEQUENCE: 23

```
Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Lys Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
```

```
                340             345             350
Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
        370                 375                 380

<210> SEQ ID NO 24
<211> LENGTH: 1155
<212> TYPE: DNA
<213> ORGANISM: Brassica napus

<400> SEQUENCE: 24
atgggtgcag gtggaagaat gcaagtgtct cctccctcca agaagtctga aaccgacacc      60
atcaagcgcg taccctgcga gacaccgccc ttcactgtcg agaactcaa gaaagcaatc     120 ccaccgcact gtttcaaacg ctcgatccct cgctctttct cctacctcat ctgggacatc     180
atcatagcct cctgcttcta ctacgtcgcc accacttact ccctctcct ccctcaccct     240 ctctcctact cgcctggcc tctctactgg gcctgccaag ggtgcgtcct aaccggcgtc     300
tgggtcatag cccacgagtg cggccaccac gccttcagcg actaccagtg gcttgacgac     360
accgtcggtc tcatcttcca ctccttcctc ctcgtccctt acttctcctg gaagtacagt     420
catcgacgcc accattccaa cactggctcc ctcgagagag acgaagtgtt tgtccccaag     480
aagaagtcag acatcaagtg gtacggcaag taccacaaca cccctttggg acgcaccgtg     540
atgttaacgg ttcagttcac tctcggctgg ccgttgtact tagccttcaa cgtctcggga     600
agaccttacg acggcggctt cgcttgccat ttccacccca acgctcccat ctacaacgac     660
cgcgagcgtc tccagatata catctccgac gctggcatcc tcgccgtctg ctacggtctc     720
ttccgttacg ccgccgcgca gggagtggcc tcgatggtct gcttctacgg agtcccgctt     780
ctgattgtca atggtttcct cgtgttgatc acttacttgc agcacacgca tccttccctg     840
cctcactacg attcgtccga gtgggattgg ttgagggag ctttggctac cgttgacaga     900
gactacggaa tcttgaacaa ggtcttccac aatattaccg acacgcacgt ggcgcatcat     960
ctgttctcca cgatgccgca ttatcacgcg atggaagcta ccaaggcgat aaagccgata    1020
ctgggagagt attatcagtt cgatgggacg ccggtggtta aggcgatgtg gagggaggcg    1080
aaggagtgta tctatgtgga accggacagg caaggtgaga gaaaggtgt gttctggtac    1140 aacaataagt tatga                                                      1155

<210> SEQ ID NO 25
<211> LENGTH: 384
<212> TYPE: PRT
<213> ORGANISM: Brassica napus

<400> SEQUENCE: 25

Met Gly Ala Gly Gly Arg Met Gln Val Ser Pro Ser Lys Lys Ser
1                   5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
```

```
                    85                  90                  95
Leu Thr Gly Val Trp Val Ile Ala His Glu Cys Gly His His Ala Phe
                100                 105                 110
Ser Asp Tyr Gln Trp Leu Asp Asp Thr Val Gly Leu Ile Phe His Ser
                115                 120                 125
Phe Leu Leu Val Pro Tyr Phe Ser Trp Lys Tyr Ser His Arg Arg His
                130                 135                 140
His Ser Asn Thr Gly Ser Leu Glu Arg Asp Glu Val Phe Val Pro Lys
145                 150                 155                 160
Lys Lys Ser Asp Ile Lys Trp Tyr Gly Lys Tyr His Asn Asn Pro Leu
                165                 170                 175
Gly Arg Thr Val Met Leu Thr Val Gln Phe Thr Leu Gly Trp Pro Leu
                180                 185                 190
Tyr Leu Ala Phe Asn Val Ser Gly Arg Pro Tyr Asp Gly Gly Phe Ala
                195                 200                 205
Cys His Phe His Pro Asn Ala Pro Ile Tyr Asn Asp Arg Glu Arg Leu
                210                 215                 220
Gln Ile Tyr Ile Ser Asp Ala Gly Ile Leu Ala Val Cys Tyr Gly Leu
225                 230                 235                 240
Phe Arg Tyr Ala Ala Ala Gln Gly Val Ala Ser Met Val Cys Phe Tyr
                245                 250                 255
Gly Val Pro Leu Leu Ile Val Asn Gly Phe Leu Val Leu Ile Thr Tyr
                260                 265                 270
Leu Gln His Thr His Pro Ser Leu Pro His Tyr Asp Ser Ser Glu Trp
                275                 280                 285
Asp Trp Leu Arg Gly Ala Leu Ala Thr Val Asp Arg Asp Tyr Gly Ile
                290                 295                 300
Leu Asn Lys Val Phe His Asn Ile Thr Asp Thr His Val Ala His His
305                 310                 315                 320
Leu Phe Ser Thr Met Pro His Tyr His Ala Met Glu Ala Thr Lys Ala
                325                 330                 335
Ile Lys Pro Ile Leu Gly Glu Tyr Tyr Gln Phe Asp Gly Thr Pro Val
                340                 345                 350
Val Lys Ala Met Trp Arg Glu Ala Lys Glu Cys Ile Tyr Val Glu Pro
                355                 360                 365
Asp Arg Gln Gly Glu Lys Lys Gly Val Phe Trp Tyr Asn Asn Lys Leu
                370                 375                 380

<210> SEQ ID NO 26
<211> LENGTH: 1155
<212> TYPE: DNA
<213> ORGANISM: Brassica napus

<400> SEQUENCE: 26
atgggtgcag gtggaagaat gcaagtgtct cctccctcca agaagtctga aaccgacacc      60
atcaagcgcg taccctgcga gacaccgccc ttcactgtcg agaactcaa gaaagcaatc     120 ccaccgcact gtttcaaacg ctcgatccct cgctctttct cctacctcat ctgggacatc     180
atcatagcct cctgcttcta ctacgtcgcc accacttact tccctctcct ccctcaccct     240
ctctcctact cgcctggcc tctctactgg gcctgccaag ggtgcgtcct aaccggcgtc     300
tgggtcatag cccacgagtg cggccaccac gccttcagcg actaccagtg gcttgacgac     360
accgtcggtc tcatcttcca ctccttcctc tcgtcccctt acttctcctg gaagtacagt     420
catcgacgcc accattccaa cactggctcc ctcgagagag acgaagtgtt tgtccccaag     480
```

```
aagaagtcag acatcaagtg gtacggcaag tacctcaaca acccttgggg acgcaccgtg   540
atgttaacgg ttcagttcac tctcggctgg ccgttgtact tagccttcaa cgtctcggga   600
agaccttacg acggcggctt cgcttgccat ttccacccca acgctcccat ctacaacgac   660
cgcgagcgtc tccagatata catctccgac gctggcatcc tcgccgtctg ctacggtctc   720
ttccgttacg ccgccgcgca gggagtggcc tcgatggtct gcttctacgg agtcccgctt   780
ctgattgtca atggtttcct cgtgttgatc acttacttgc agcacacgca tccttccctg   840
cctcactacg attcgtccga gtgggattgg ttgaggggag ctttggctac cgttgacaga   900
gactacgaaa tcttgaacaa ggtcttccac aatattaccg acacgcacgt ggcgcatcat   960
ctgttctcca cgatgccgca ttatcacgcg atggaagcta ccaaggcgat aaagccgata  1020
ctgggagagt attatcagtt cgatgggacg ccggtggtta aggcgatgtg gagggaggcg  1080
aaggagtgta tctatgtgga accggacagg caaggtgaga gaaaggtgt gttctggtac  1140 aacaataagt tatga                                                   1155

<210> SEQ ID NO 27
<211> LENGTH: 384
<212> TYPE: PRT
<213> ORGANISM: Brassica napus

<400> SEQUENCE: 27

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255
```

```
Gly Val Pro Leu Leu Ile Val Asn Gly Phe Leu Val Leu Ile Thr Tyr
            260                 265                 270
Leu Gln His Thr His Pro Ser Leu Pro His Tyr Asp Ser Ser Glu Trp
            275                 280                 285
Asp Trp Leu Arg Gly Ala Leu Ala Thr Val Asp Arg Asp Tyr Glu Ile
            290                 295                 300
Leu Asn Lys Val Phe His Asn Ile Thr Asp Thr His Val Ala His His
305                 310                 315                 320
Leu Phe Ser Thr Met Pro His Tyr His Ala Met Glu Ala Thr Lys Ala
                325                 330                 335
Ile Lys Pro Ile Leu Gly Glu Tyr Tyr Gln Phe Asp Gly Thr Pro Val
            340                 345                 350
Val Lys Ala Met Trp Arg Glu Ala Lys Glu Cys Ile Tyr Val Glu Pro
            355                 360                 365
Asp Arg Gln Gly Glu Lys Lys Gly Val Phe Trp Tyr Asn Asn Lys Leu
            370                 375                 380

<210> SEQ ID NO 28
<211> LENGTH: 1155
<212> TYPE: DNA
<213> ORGANISM: Artificial
<220> FEATURE:
<223> OTHER INFORMATION: Brassica napus fad2 mutants
<220> FEATURE:
<221> NAME/KEY: misc_feature
<222> LOCATION: (59)..(59)
<223> OTHER INFORMATION: A or C
<220> FEATURE:
<221> NAME/KEY: misc_feature
<222> LOCATION: (269)..(269)
<223> OTHER INFORMATION: G or A
<220> FEATURE:
<221> NAME/KEY: misc_feature
<222> LOCATION: (279)..(279)
<223> OTHER INFORMATION: G or A
<220> FEATURE:
<221> NAME/KEY: misc_feature
<222> LOCATION: (282)..(282)
<223> OTHER INFORMATION: C or G
<220> FEATURE:
<221> NAME/KEY: misc_feature
<222> LOCATION: (346)..(346)
<223> OTHER INFORMATION: C or T
<220> FEATURE:
<221> NAME/KEY: misc_feature
<222> LOCATION: (354)..(354)
<223> OTHER INFORMATION: G or T
<220> FEATURE:
<221> NAME/KEY: misc_feature
<222> LOCATION: (369)..(369)
<223> OTHER INFORMATION: C or T
<220> FEATURE:
<221> NAME/KEY: misc_feature
<222> LOCATION: (573)..(573)
<223> OTHER INFORMATION: T or G
<220> FEATURE:
<221> NAME/KEY: misc_feature
<222> LOCATION: (600)..(600)
<223> OTHER INFORMATION: G or A
<220> FEATURE:
<221> NAME/KEY: misc_feature
<222> LOCATION: (646)..(646)
<223> OTHER INFORMATION: C or T
<220> FEATURE:
<221> NAME/KEY: misc_feature
<222> LOCATION: (663)..(663)
<223> OTHER INFORMATION: T or C
<220> FEATURE:
<221> NAME/KEY: misc_feature
<222> LOCATION: (722)..(722)
<223> OTHER INFORMATION: A or T
<220> FEATURE:
```

```
<221> NAME/KEY: misc_feature
<222> LOCATION: (726)..(726)
<223> OTHER INFORMATION: C or T
<220> FEATURE:
<221> NAME/KEY: misc_feature
<222> LOCATION: (732)..(732)
<223> OTHER INFORMATION: T or C
<220> FEATURE:
<221> NAME/KEY: misc_feature
<222> LOCATION: (735)..(735)
<223> OTHER INFORMATION: T or C
<220> FEATURE:
<221> NAME/KEY: misc_feature
<222> LOCATION: (737)..(737)
<223> OTHER INFORMATION: T or C
<220> FEATURE:
<221> NAME/KEY: misc_feature
<222> LOCATION: (738)..(738)
<223> OTHER INFORMATION: C or G
<220> FEATURE:
<221> NAME/KEY: misc_feature
<222> LOCATION: (741)..(741)
<223> OTHER INFORMATION: A or G
<220> FEATURE:
<221> NAME/KEY: misc_feature
<222> LOCATION: (747)..(747)
<223> OTHER INFORMATION: T or G
<220> FEATURE:
<221> NAME/KEY: misc_feature
<222> LOCATION: (753)..(753)
<223> OTHER INFORMATION: T or G
<220> FEATURE:
<221> NAME/KEY: misc_feature
<222> LOCATION: (774)..(774)
<223> OTHER INFORMATION: T or C
<220> FEATURE:
<221> NAME/KEY: misc_feature
<222> LOCATION: (775)..(775)
<223> OTHER INFORMATION: C or T
<220> FEATURE:
<221> NAME/KEY: misc_feature
<222> LOCATION: (777)..(777)
<223> OTHER INFORMATION: T or G
<220> FEATURE:
<221> NAME/KEY: misc_feature
<222> LOCATION: (792)..(792)
<223> OTHER INFORMATION: C or T
<220> FEATURE:
<221> NAME/KEY: misc_feature
<222> LOCATION: (795)..(795)
<223> OTHER INFORMATION: G or T
<220> FEATURE:
<221> NAME/KEY: misc_feature
<222> LOCATION: (799)..(799)
<223> OTHER INFORMATION: T or C
<220> FEATURE:
<221> NAME/KEY: misc_feature
<222> LOCATION: (801)..(801)
<223> OTHER INFORMATION: A or C
<220> FEATURE:
<221> NAME/KEY: misc_feature
<222> LOCATION: (804)..(804)
<223> OTHER INFORMATION: T or G
<220> FEATURE:
<221> NAME/KEY: misc_feature
<222> LOCATION: (827)..(827)
<223> OTHER INFORMATION: C or T
<220> FEATURE:
<221> NAME/KEY: misc_feature
<222> LOCATION: (849)..(849)
<223> OTHER INFORMATION: T or C
<220> FEATURE:
<221> NAME/KEY: misc_feature
<222> LOCATION: (852)..(852)
<223> OTHER INFORMATION: C or T
<220> FEATURE:
<221> NAME/KEY: misc_feature
<222> LOCATION: (858)..(858)
<223> OTHER INFORMATION: T or C
<220> FEATURE:
```

```
<221> NAME/KEY: misc_feature
<222> LOCATION: (888)..(888)
<223> OTHER INFORMATION: C or T
<220> FEATURE:
<221> NAME/KEY: misc_feature
<222> LOCATION: (936)..(936)
<223> OTHER INFORMATION: C or T
<220> FEATURE:
<221> NAME/KEY: misc_feature
<222> LOCATION: (939)..(939)
<223> OTHER INFORMATION: G or C
<220> FEATURE:
<221> NAME/KEY: misc_feature
<222> LOCATION: (960)..(960)
<223> OTHER INFORMATION: C or T
<220> FEATURE:
<221> NAME/KEY: misc_feature
<222> LOCATION: (969)..(969)
<223> OTHER INFORMATION: G or C
<220> FEATURE:
<221> NAME/KEY: misc_feature
<222> LOCATION: (972)..(972)
<223> OTHER INFORMATION: C or G
<220> FEATURE:
<221> NAME/KEY: misc_feature
<222> LOCATION: (987)..(987)
<223> OTHER INFORMATION: T or C
<220> FEATURE:
<221> NAME/KEY: misc_feature
<222> LOCATION: (1002)..(1002)
<223> OTHER INFORMATION: G or C

<400> SEQUENCE: 28
atgggtgcag gtggaagaat gcaagtgtct cctccctcca aaaagtctga aaccgacanc      60
atcaagcgcg taccctgcga gacaccgccc ttcactgtcg gagaactcaa gaaagcaatc     120
ccaccgcact gtttcaaacg ctcgatccct cgctctttct cctacctcat ctgggacatc     180
atcatagcct cctgcttcta ctacgtcgcc accacttact ccctctcct ccctcaccct      240 ctctcctact tcgcctggcc tctctactng gcctgccang gntgcgtcct aaccggcgtc     300
tgggtcatag cccacgagtg cggccaccac gccttcagcg actacnagtg gctngacgac     360
accgtcggnc tcatcttcca ctccttcctc ctcgtccctt acttctcctg gaagtacagt     420
catcgacgcc accattccaa cactggctcc ctcgagagag acgaagtgtt tgtcccaag      480 aagaagtcag acatcaagtg gtacggcaag tacctcaaca ccctttggg acgcaccgtg      540 atgttaacgg ttcagttcac tctcggctgg ccnttgtact tagccttcaa cgtctcgggn     600
agaccttacg acggcggctt cgcttgccat ttccacccca acgctnccat ctacaacgac     660
cgngagcgtc tccagatata catctccgac gctggcatcc tcgccgtctg ctacggtctc     720
tnccgntacg cngcngnnca nggagtngcc tcnatggtct gcttctacgg agtnncnctt     780
ctgattgtca anggnttcnt ngtnttgatc acttacttgc agcacangca tccttccctg     840
cctcactang antcgtcnga gtgggattgg ttgaggggag ctttggcnac cgttgacaga     900
gactacggaa tcttgaacaa ggtcttccac aatatnacng acacgcacgt ggcgcatcan     960
ctgttctcna cnatgccgca ttatcangcg atggaagcta cnaaggcgat aaagccgata    1020
ctgggagagt attatcagtt cgatgggacg ccggtggtta aggcgatgtg gagggaggcg    1080
aaggagtgta tctatgtgga accggacagg caaggtgaga agaaaggtgt gttctggtac    1140
aacaataagt tatga                                                    1155

<210> SEQ ID NO 29
<211> LENGTH: 384
<212> TYPE: PRT
<213> ORGANISM: Artificial
<220> FEATURE:
```

```
<223> OTHER INFORMATION: Brassica napus fad2 mutants
<220> FEATURE:
<221> NAME/KEY: MISC_FEATURE
<222> LOCATION: (20)..(20)
<223> OTHER INFORMATION: Asn or Thr
<220> FEATURE:
<221> NAME/KEY: MISC_FEATURE
<222> LOCATION: (216)..(216)
<223> OTHER INFORMATION: Pro or Ser
<220> FEATURE:
<221> NAME/KEY: MISC_FEATURE
<222> LOCATION: (241)..(241)
<223> OTHER INFORMATION: Tyr or Phe
<220> FEATURE:
<221> NAME/KEY: MISC_FEATURE
<222> LOCATION: (246)..(246)
<223> OTHER INFORMATION: Ala or Val
<220> FEATURE:
<221> NAME/KEY: MISC_FEATURE
<222> LOCATION: (259)..(259)
<223> OTHER INFORMATION: Pro or Ser
<220> FEATURE:
<221> NAME/KEY: MISC_FEATURE
<222> LOCATION: (276)..(276)
<223> OTHER INFORMATION: Thr or Met

<400> SEQUENCE: 29

Met Gly Ala Gly Gly Arg Met Gln Val Ser Pro Ser Lys Lys Ser
 1               5                  10                  15

Glu Thr Asp Xaa Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
 50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
            130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Xaa Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Xaa Arg Tyr Ala Ala Xaa Gln Gly Val Ala Ser Met Val Cys Phe Tyr
                245                 250                 255

Gly Val Xaa Leu Leu Ile Val Asn Gly Phe Leu Val Leu Ile Thr Tyr
            260                 265                 270

Leu Gln His Xaa His Pro Ser Leu Pro His Tyr Asp Ser Ser Glu Trp
```

```
                    275                 280                 285
Asp Trp Leu Arg Gly Ala Leu Ala Thr Val Asp Arg Asp Tyr Gly Ile
        290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
        370                 375                 380

<210> SEQ ID NO 30
<211> LENGTH: 1155
<212> TYPE: DNA
<213> ORGANISM: Artificial
<220> FEATURE:
<223> OTHER INFORMATION: Brassica napus fad2-a mutant

<400> SEQUENCE: 30
atgggtgcag gtggaagaat gcaagtgtct cctccctcca aaaagtctga aaccgacaac      60
atcaagcgcg taccctgcga cacccgccc  ttcactgtcg gagaactcaa gaaagcaatc     120
ccaccgcact gtttcaaacg ctcgatccct cgctctttct cctacctcat ctgggacatc     180
atcatagcct cctgcttcta ctacgtcgcc accacttact ccctctcct  ccctcaccct    240 ctctcctact tcgcctggcc tctctactag gcctgccagg gctgcgtcct aaccggcgtc     300
tgggtcatag cccacgagtg cggccaccac gccttcagcg actaccagtg gctggacgac     360
accgtcggcc tcatcttcca ctccttcctc ctcgtccctt acttctcctg gaagtacagt     420
catcgacgcc accattccaa cactggctcc ctcgagagag acgaagtgtt tgtccccaag     480
aagaagtcag acatcaagtg gtacggcaag tacctcaaca ccctttggg  acgcaccgtg     540 atgttaacgg ttcagttcac tctcggctgg cctttgtact tagccttcaa cgtctcgggg     600
agaccttacg acggcggctt cgcttgccat ttccacccca acgctcccat ctacaacgac     660
cgtgagcgtc tccagatata catctccgac gctggcatcc tcgccgtctg ctacggtctc     720
taccgctacg ctgctgtcca aggagttgcc tctatggtct gcttctacgg agttcctctt     780
ctgattgtca acgggttctt agttttgatc acttacttgc agcacacgca tccttccctg     840
cctcactatg actcgtctga gtgggattgg ttgaggggag ctttggccac cgttgacaga     900
gactacggaa tcttgaacaa ggtcttccac aatatcacgg acacgcacgt ggcgcatcac     960
ctgttctcga ccatgccgca ttatcatgcg atggaagcta cgaaggcgat aaagccgata    1020
ctgggagagt attatcagtt cgatgggacg ccggtggtta aggcgatgtg gagggaggcg    1080
aaggagtgta tctatgtgga accggacagg caaggtgaga gaaaggtgt  gttctggtac   1140 aacaataagt tatga                                                     1155

<210> SEQ ID NO 31
<211> LENGTH: 89
<212> TYPE: PRT
<213> ORGANISM: Artificial
<220> FEATURE:
<223> OTHER INFORMATION: Brassica napus fad2-a mutant

<400> SEQUENCE: 31
```

```
Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr
                85

<210> SEQ ID NO 32
<211> LENGTH: 1155
<212> TYPE: DNA
<213> ORGANISM: Artificial
<220> FEATURE:
<223> OTHER INFORMATION: Brassica napus fad2-a mutant

<400> SEQUENCE: 32
atgggtgcag gtggaagaat gcaagtgtct cctccctcca aaaagtctga aaccgacaac     60
atcaagcgcg taccctgcga gacaccgccc ttcactgtcg gagaactcaa gaaagcaatc    120
ccaccgcact gtttcaaacg ctcgatccct cgctctttct cctacctcat ctgggacatc    180
atcatagcct cctgcttcta ctacgtcgcc accacttact ccctctcct ccctcaccct    240 ctctcctact cgcctggcc tctctactgg gcctgccagg gctgcgtcct aaccggcgtc    300
tgggtcatag cccacgagtg cggccaccac gccttcagcg actactagtg gctggacgac    360
accgtcggcc tcatcttcca ctccttcctc ctcgtccctt acttcctg gaagtacagt     420 catcgacgcc accattccaa cactggctcc ctcgagagag acgaagtgtt tgtccccaag    480
aagaagtcag acatcaagtg gtacggcaag tacctcaaca cccctttggg acgcaccgtg    540
atgttaacgg ttcagttcac tctcggctgg cctttgtact agccttcaa cgtctcgggg    600 agaccttacg acgcggcttc gcttgccat ttccacccca acgctccat ctacaacgac    660 cgtgagcgtc tccagatata catctccgac gctggcatcc tcgccgtctg ctacggtctc    720
taccgctacg ctgctgtcca aggagttgcc tctatggtct gcttctacgg agttcctctt    780
ctgattgtca acgggttctt agttttgatc acttacttgc agcacacgca tccttccctg    840
cctcactatg actcgtctga gtgggattgg ttgaggggag cttggccac cgttgacaga    900 gactacggaa tcttgaacaa ggtcttccac aatatcacgg acacgcacgt ggcgcatcac    960
ctgttctcga ccatgccgca ttatcatgcg atggaagcta cgaaggcgat aaagccgata   1020
ctgggagagt attatcagtt cgatgggacg ccggtggtta aggcgatgtg gagggaggcg   1080
aaggagtgta tctatgtgga accggacagg caaggtgaga agaaaggtgt gttctggtac   1140
aacaataagt tatga                                                   1155

<210> SEQ ID NO 33
<211> LENGTH: 115
<212> TYPE: PRT
<213> ORGANISM: Artificial
<220> FEATURE:
<223> OTHER INFORMATION: Brassica napus fad2-a mutant

<400> SEQUENCE: 33

Met Gly Ala Gly Gly Arg Met Gln Val Ser Pro Pro Ser Lys Lys Ser
1               5                   10                  15
```

```
Glu Thr Asp Asn Ile Lys Arg Val Pro Cys Glu Thr Pro Pro Phe Thr
            20                  25                  30
Val Gly Glu Leu Lys Lys Ala Ile Pro Pro His Cys Phe Lys Arg Ser
        35                  40                  45
Ile Pro Arg Ser Phe Ser Tyr Leu Ile Trp Asp Ile Ile Ala Ser
50                  55                  60
Cys Phe Tyr Tyr Val Ala Thr Thr Tyr Phe Pro Leu Leu Pro His Pro
65                  70                  75                  80
Leu Ser Tyr Phe Ala Trp Pro Leu Tyr Trp Ala Cys Gln Gly Cys Val
                85                  90                  95
Leu Thr Gly Val Trp Val Ile Ala His Glu Cys Gly His His Ala Phe
            100                 105                 110
Ser Asp Tyr
        115

<210> SEQ ID NO 34
<211> LENGTH: 1155
<212> TYPE: DNA
<213> ORGANISM: Artificial
<220> FEATURE:
<223> OTHER INFORMATION: Brassica napus fad2-a mutant

<400> SEQUENCE: 34
atgggtgcag gtggaagaat gcaagtgtct cctccctcca aaaagtctga aaccgacacc      60
atcaagcgcg taccctgcga gacaccgccc ttcactgtcg agaactcaa gaaagcaatc     120 ccaccgcact gtttcaaacg ctcgatccct cgctctttct cctacctcat ctgggacatc     180
atcatagcct cctgcttcta ctacgtcgcc accacttact ccctctcct ccctcaccct     240 ctctcctact tcgcctggcc tctctactgg gcctgccaag ggtgcgtcct aaccggcgtc     300
tgggtcatag cccacgagtg cggccaccac gccttcagcg actaccgtg gcttgacgac     360 accgtcggtc tcatcttcca ctccttcctc ctcgtcccctt acttctcctg gaagtacagt     420
catcgacgcc accattccaa cactggctcc ctcgagagag acgaagtgtt tgtccccaag     480
aagaagtcag acatcaagtg gtacggcaag tacctcaaca ccctttggg acgcaccgtg     540 atgttaacgg ttcagttcac tctcggctgg ccgttgtact agccttcaa cgtctcggga     600 agaccttacg acggcggctt cgcttgccat ttccaccca acgcttccat ctacaacgac     660
cgcgagcgtc tccagatata catctccgac gctggcatcc tcgccgtctg ctacggtctc     720
ttccgttacg ccgccgcgca gggagtggcc tcgatggtct gcttctacgg agtcccgctt     780
ctgattgtca atggtttcct cgtgttgatc acttacttgc agcacacgca tccttccctg     840
cctcactacg attcgtccga gtgggattgg ttgaggggag cttttggctac cgttgacaga     900 gactacggaa tcttgaacaa ggtcttccac aatattaccg acacgcacgt ggcgcatcat     960
ctgttctcca cgatgccgca ttatcacgcg atggaagcta ccaaggcgat aaagccgata    1020
ctgggagagt attatcagtt cgatgggacg ccggtggtta aggcgatgtg gagggaggcg    1080
aaggagtgta tctatgtgga accggacagg caaggtgaga agaaaggtgt gttctggtac    1140
aacaataagt tatga                                                   1155

<210> SEQ ID NO 35
<211> LENGTH: 384
<212> TYPE: PRT
<213> ORGANISM: Artificial
<220> FEATURE:
<223> OTHER INFORMATION: Brassica napus fad2-a mutant
```

<400> SEQUENCE: 35

```
Met Gly Ala Gly Gly Arg Met Gln Val Ser Pro Pro Ser Lys Lys Ser
1               5                   10                  15

Glu Thr Asp Thr Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Ser Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Ala Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380
```

<210> SEQ ID NO 36
<211> LENGTH: 1155
<212> TYPE: DNA
<213> ORGANISM: Artificial
<220> FEATURE:

<223> OTHER INFORMATION: Brassica napus fad2-a mutant

<400> SEQUENCE: 36

```
atgggtgcag gtggaagaat gcaagtgtct cctccctcca aaaagtctga aaccgacaac    60
atcaagcgcg taccctgcga cacccgccc  ttcactgtcg gagaactcaa gaaagcaatc   120
ccaccgcact gtttcaaacg ctcgatcccct cgctctttct cctacctcat ctgggacatc   180
atcatagcct cctgcttcta ctacgtcgcc accacttact ccctctcct  ccctcaccct   240
ctctcctact cgcctggcc  tctctactgg gcctgccagg gctgcgtcct aaccggcgtc   300
tgggtcatag cccacgagtg cggccaccac gccttcagcg actaccagtg gctggacgac   360
accgtcggcc tcatcttcca ctccttcctc ctcgtccctt acttctcctg gaagtacagt   420
catcgacgcc accattccaa cactggctcc ctcgagagag acgaagtgtt tgtccccaag   480
aagaagtcag acatcaagtg gtacggcaag tacctcaaca acccttggg  acgcaccgtg   540
atgttaacgg ttcagttcac tctcggctgg cctttgtact tagccttcaa cgtctcgggg   600
agaccttacg acggcggctt cgcttgccat ttccacccca acgctcccat ctacaacgac   660
cgtgagcgtc tccagatata catctccgac gctggcatcc tcgccgtctg ctacggtctc   720
taccgctacg ctgctgtcca aggagttgcc tctatggtct gcttctacgg agtttctctt   780
ctgattgtca acgggttctt agttttgatc acttacttgc agcacacgca tccttccctg   840
cctcactatg actcgtctga gtgggattgg ttgagggggag ctttggccac cgttgacaga   900
gactacggaa tcttgaacaa ggtcttccac aatatcacgg acacgcacgt ggcgcatcac   960
ctgttctcga ccatgccgca ttatcatgcg atggaagcta cgaaggcgat aaagccgata  1020
ctgggagagt attatcagtt cgatgggacg ccggtggtta aggcgatgtg gagggaggcg  1080
aaggagtgta tctatgtgga accggacagg caaggtgaga agaaaggtgt gttctggtac  1140
aacaataagt tatga                                                   1155
```

<210> SEQ ID NO 37
<211> LENGTH: 384
<212> TYPE: PRT
<213> ORGANISM: Artificial
<220> FEATURE:
<223> OTHER INFORMATION: Brassica napus fad2-a mutant

<400> SEQUENCE: 37

```
Met Gly Ala Gly Gly Arg Met Gln Val Ser Pro Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140
```

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
            165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Ser Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
    370                 375                 380

<210> SEQ ID NO 38
<211> LENGTH: 1155
<212> TYPE: DNA
<213> ORGANISM: Artificial
<220> FEATURE:
<223> OTHER INFORMATION: Brassica napus fad2-a mutant

<400> SEQUENCE: 38

```
atgggtgcag gtggaagaat gcaagtgtct cctccctcca aaaagtctga aaccgacaac      60
atcaagcgcg taccctgcga gacaccgccc ttcactgtcg agaactcaa gaaagcaatc      120 ccaccgcact gtttcaaacg ctcgatccct cgctctttct cctacctcat ctgggacatc     180
atcatagcct cctgcttcta ctacgtcgcc accacttact ccctctcct ccctcaccct     240 ctctcctact cgcctggcc tctctactgg gcctgccagg gctgcgtcct aaccggcgtc     300
tgggtcatag cccacgagtg cggccaccac gccttcagcg actaccagtg gctggacgac     360
accgtcggcc tcatcttcca ctccttcctc tcgtcccctt acttctcctg gaagtacagt     420
catcgacgcc accattccaa cactggctcc ctcgagagag acgaagtgtt tgtccccaag     480
aagaagtcag acatcaagtg gtacggcaag tacctcaaca ccctttgggg acgcaccgtg     540
atgttaacgg ttcagttcac tctcggctgg cctttgtact agccttcaa cgtctcgggg     600 agaccttacg acggcggctt cgcttgccat ttccacccca acgctcccat ctacaacgac     660
cgtgagcgtc tccagatata catctccgac gctggcatcc tcgccgtctg ctacggtctc     720
```

```
taccgctacg ctgctgtcca aggagttgcc tctatggtct gcttctacgg agttcctctt    780
ctgattgtca acgggttctt agttttgatc acttacttgc agcacatgca tccttccctg    840
cctcactatg actcgtctga gtgggattgg ttgaggggag ctttggccac cgttgacaga    900
gactacggaa tcttgaacaa ggtcttccac aatatcacgg acacgcacgt ggcgcatcac    960
ctgttctcga ccatgccgca ttatcatgcg atggaagcta cgaaggcgat aaagccgata   1020
ctgggagagt attatcagtt cgatgggacg ccggtggtta aggcgatgtg gagggaggcg   1080
aaggagtgta tctatgtgga accggacagg caaggtgaga agaaaggtgt gttctggtac   1140
aacaataagt tatga                                                   1155
```

<210> SEQ ID NO 39
<211> LENGTH: 384
<212> TYPE: PRT
<213> ORGANISM: Artificial
<220> FEATURE:
<223> OTHER INFORMATION: Brassica napus fad2-a mutant

<400> SEQUENCE: 39

```
Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Met His Pro Ser Leu Pro His Tyr Asp Ser Ser Glu Trp
        275                 280                 285
```

-continued

```
Asp Trp Leu Arg Gly Ala Leu Ala Thr Val Asp Arg Asp Tyr Gly Ile
    290                 295             300

Leu Asn Lys Val Phe His Asn Ile Thr Asp Thr His Val Ala His His
305                 310             315                 320

Leu Phe Ser Thr Met Pro His Tyr His Ala Met Glu Ala Thr Lys Ala
                325             330                 335

Ile Lys Pro Ile Leu Gly Glu Tyr Tyr Gln Phe Asp Gly Thr Pro Val
            340             345             350

Val Lys Ala Met Trp Arg Glu Ala Lys Glu Cys Ile Tyr Val Glu Pro
    355                 360             365

Asp Arg Gln Gly Glu Lys Lys Gly Val Phe Trp Tyr Asn Asn Lys Leu
    370             375             380
```

OMEGA-9 QUALITY *BRASSICA JUNCEA*

CROSS-REFERENCE TO RELATED APPLICATION

This application is a utility conversion of U.S. Provisional Patent Application Ser. No. 61/198,422, filed Nov. 4, 2008, for "Omega-9 Quality *Brassica Juncea*," the entire disclosure of which is hereby incorporated herein by this reference.

FIELD OF THE INVENTION

The invention is in the field of improved *Brassica* species, including *Brassica juncea*, improved oil and meal from *Brassica juncea*, methods for generation of such improved *Brassica* species, and methods for selection of *Brassica* lines. Further embodiments relate to seeds of *Brassica juncea* comprising an endogenous oil having increased oleic acid content and decreased linolenic acid content relative to presently existing commercial cultivars of *Brassica juncea*, and seeds of *Brassica juncea* having traits for increased oleic acid content and decreased linolenic acid content in seed oil stably incorporated therein.

BACKGROUND OF THE INVENTION

Canola is a genetic variation of rapeseed developed by Canadian plant breeders specifically for its oil and meal attributes, particularly its low level of saturated fat. "Canola" generally refers to plants of *Brassica* species that have less than 2% erucic acid ($\Delta$13-22:1) by weight in seed oil and less than 30 micromoles of glucosinolates per gram of oil free meal. Typically, canola oil may include saturated fatty acids known as palmitic acid and stearic acid, a monounsaturated fatty acid known as oleic acid, and polyunsaturated fatty acids known as linoleic acid and linolenic acid. These fatty acids are sometimes referenced by the length of their carbon chain and the number of double bonds in the chain. For example, oleic acid is sometimes referred to as C18:1 because it has an 18-carbon chain and one double bond, linoleic acid is sometimes referred to as C18:2 because it has an 18-carbon chain and two double bonds, and linolenic acid is sometimes referred to as C18:3 because it has an 18-carbon chain and three double bonds. Canola oil may contain less than about 7% total saturated fatty acids (mostly palmitic acid and stearic acid) and greater than 60% oleic acid (as percentages of total fatty acids). Traditionally, canola crops include varieties of *Brassica napus* and *Brassica rapa*. Recently, a canola quality *Brassica juncea* variety, which has oil and meal qualities similar to other canola types, has been added to the canola crop family (U.S. Pat. No. 6,303,849, to Potts et al., issued on Oct. 16, 2001; U.S. Pat. No. 7,423,198, to Yao et al.; Potts and Males, 1999; all of which are incorporated herein by reference).

The fatty acid composition of a vegetable oil affects the oil's quality, stability, and health attributes. For example, oleic acid (a C18:1 monounsaturated fatty acid) has been recognized to have certain health benefits, including effectiveness in lowering plasma cholesterol levels, making higher levels of oleic acid content in seed oil (>70%) a desirable trait. Further, not all fatty acids in vegetable oils are equally vulnerable to high temperature and oxidation. Rather, the susceptibility of individual fatty acids to oxidation is dependent on their degree of unsaturation. For example, linolenic acid (C18:3), which has three carbon-carbon double bonds, oxidizes 98 times faster than oleic acid, which has only one carbon-carbon double bond, and linoleic acid, which has two carbon-carbon double bonds, oxidizes 41 times faster than oleic acid (R. T. Holman and O. C. Elmer, "The rates of oxidation of unsaturated fatty acid esters," *J. Am. Oil Chem. Soc.* 24, 127-129 1947. For further information regarding the relative oxidation rates of oleic, linoleic and linolenic fatty acids, see Hawrysh, "Stability of Canola Oil," Chap. 7, pp. 99-122, CANOLA AND RAPESEED: PRODUCTION, CHEMISTRY, NUTRITION, AND PROCESSING TECHNOLOGY, Shahidi, ed., Van Nostrand Reinhold, N.Y., 1990, incorporated by reference herein.

The "stability" of a vegetable oil can be defined as the resistance of the oil to oxidation and to the resulting deterioration due to the generation of products causing rancidity and decreasing food quality. Under identical processing, formulation, packaging and storage conditions, the major difference in stability between different vegetable oils is due to their different fatty acid profiles. High oleic acid content vegetable oil is therefore preferred in cooking applications because of its increased resistance to oxidation in the presence of heat. Poor oxidative stability brings about, for example, shortened operation times in the case where the oil is used as a fry oil because oxidation produces off-flavors and odors that can greatly reduce the marketable value of the oil. For these reasons, high oleic acid and low linolenic acid may be desirable traits in plant oils.

Plants synthesize fatty acids in their plastids as palmitoyl-ACP (16:0-ACP) and stearoyl-ACP. The conversion of stearoyl-ACP to oleoyl-ACP (18:1-ACP) is catalyzed by a soluble enzyme, the stearoyl-ACP $\Delta$9 desaturase (Shanklin and Somerville, 1991). These acyl-ACPs are either used for glycolipid synthesis in chloroplasts or transported out of chloroplasts into the cytoplasm as acyl-CoAs. Further desaturation of oleic acid occurs only after it is used in the synthesis of glycerolipids and incorporated into membranes, which leads to the synthesis of polyunsaturated fatty acids.

It is widely known by those of skill in the art that the unsaturation of fatty acids in oilseed crops is controlled in part by fatty acid desaturase (FAD) enzymes. FAD enzymes regulate the unsaturation of fatty acids, such as stearic acid (C18: 0), oleic acid (C18:1) and linoleic acid (C18:2), through the removal of hydrogen atoms from defined carbons of a fatty acyl chain, creating carbon-carbon double bonds. The synthesis of polyunsaturated fatty acids linoleate ($\Delta$9, 12-18:2) and $\alpha$-linolenate ($\Delta$9, 12, 15-18:3) begins with the conversion of oleic acid ($\Delta$9-18:1) to linoleic acid, the enzymatic step catalyzed by the microsomal $\omega$-6 oleic acid desaturase (FAD2). The linoleic acid is then converted to $\omega$-linolenic acid through further desaturation by $\omega$-3 linoleic acid desaturase (FAD3). There are reports that manipulation of the FAD2 gene through genetic engineering could alter fatty acid profiles. For example, heterologous expression of a soybean fad2 gene in an *Arabidopsis* mutant line led to dramatic increase in the accumulation of polyunsaturated fatty acids (Heppard et al., 1996). In contrast, in an *Arabidopsis* mutant line fad2-5, where the transcription of the fad2 gene was decreased significantly due to T-DNA insertion, showed a dramatic increase in the accumulation of oleic acid and a significant decrease in the levels of linoleic acid and linolenic acid (Okuley et al., 1994). These findings suggest that the FAD2 gene plays an important role in controlling conversion of oleic acid to linoleic acid in seed storage lipids.

Significant efforts have been made to manipulate the fatty acid profile of plants, particularly oil-seed varieties such as *Brassica* spp. that are used for the large-scale production of commercial fats and oils (see, for example, U.S. Pat. Nos. 5,625,130 issued 29 Apr. 1997, 5,668,299 issued 16 Sep. 1997, 5,767,338 issued 16 Jun. 1998, 5,840,946 issued 24 Nov. 1998, 5,850,026 issued 15 Dec. 1998, 5,861,187 issued 19 Jan. 1999, 6,063,947 issued 16 May 2000, 6,084,157 issued 4 Jul. 2000, 6,169,190 issued 2 Jan. 2001, 6,323,392 issued 27 Nov. 2001, and international patent applications WO 97/43907 published 27 Nov. 1997 and WO 00/51415 published 8 Sep. 2000).

*Brassica juncea* (AA BB genome; n=18) (also referred to herein as "*B. juncea*") is an amphidiploid plant of the *Brassica* genus that is generally thought to have resulted from the hybridization of *Brassica rapa* (AA genome; n=10) and *Brassica nigra* (BB genome; n=8). *Brassica napus* (AA CC genome; n=19) (also referred to herein as "*B. napus*") is also an amphidiploid plant of the *Brassica* genus but is thought to have resulted from hybridization of *Brassica rapa* and *Brassica oleracea* (CC genome; n=9). Under some growing conditions, *B. juncea* may have certain superior traits to *B. napus*. These superior traits may include higher yield, better drought and heat tolerance and better disease resistance. Intensive breeding efforts have produced plants of *Brassica* species whose seed oil contains less than 2% erucic acid and whose de-fatted meal contains less than 30 micromoles glucosinolates per gram. The term "canola" has been used to describe varieties of *Brassica* spp. containing low erucic acid (Δ13-22:1) and low glucosinolates. Typically, canola oil may contain less than about 7% total saturated fatty acids and greater than 60% oleic acid (as percentages of total fatty acids). For example, in the United States, under 21 CFR 184.1555, low erucic acid rapeseed oil derived from *Brassica napus* or *Brassica rapa* is recognized as canola oil where it has an erucic acid content of no more than 2% of the component fatty acids, an oleic acid (C18:1) content of over 50.0% by weight, a linoleic acid (C18:2) content of less than 40.0% by weight, and a linolenic acid (C18:3) content of less than 14.0% by weight. In Canada, the addition of *Brassica juncea* to the canola definition by the Canola Council of Canada set the additional requirements that *Brassica juncea* canola varieties must produce seeds having an oil comprising an oleic acid content equal to or greater than 55% of total fatty acids in the seeds, and meal derived from *Brassica juncea* canola seeds must contain less than 1 micromole of allyl (2-propenyl) glucosinolates per gram of oil free meal.

Differences between the oil compositions of *Brassica juncea* and *Brassica napus* are well known in the art. For example, *Brassica juncea* is known to contain differences in various constituents, including, but not limited to, phenolics (e.g., tocopherols), sterols, sulfides, fatty acid constituents, minerals, and isothiocyanates. *Brassica juncea* also contains volatiles having strong antimicrobial (bacteria and fungi) properties.

Plant breeders have also selected canola varieties that are low in glucosinolates, such as 3-butenyl, 4-pentenyl, 2-hydroxy-3-butenyl or 2-hydroxy-4-pentenyl glucosinolate. Canola quality meal may for example be defined as having a glucosinolate content of less than 30 micromoles of aliphatic glucosinolates per gram of oil-free meal. Currently, the principal commercial canola crops comprise *Brassica napus* and *Brassica rapa* (*campestris*) varieties. U.S. Pat. No. 6,303,849 issued to Potts et al., on 16 Oct. 2001 (incorporated herein by reference) discloses *Brassica juncea* lines having edible oil that has properties similar to canola. The *Brassica juncea* lines disclosed therein have a lineage that includes *Brassica juncea* lines J90-3450 and J90-4316, deposited as ATCC Accession Nos. 203389 and 203390 respectively (both of which were deposited by Agriculture and Agri-Food Canada under the terms of the Budapest Treaty on 23 Oct. 1998 at the American Type Culture Collection, 10801 University Blvd., Manassas, Va. USA 20110-2209).

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

In various aspects, the invention provides *Brassica juncea* plants, seeds, cells, allelic variations of nucleic acid sequences and oils. Edible oil in seeds of plants of the invention may have significantly higher oleic acid content and lower linolenic acid content than found in seeds of other *Brassica juncea* plants. A number of high oleic acid/low linolenic acid ("HOLL") *Brassica juncea* lines are disclosed in the current invention. In one embodiment, a *Brassica juncea* line comprises FAD2 and FAD3 genes, as disclosed in International Publication No. US 2006/0248611 A1 (the contents of which are incorporated by reference herein), which are exemplified in FIGS. 1 and 3, and SEQ. ID. NOS. 1-4. The resulting mutant allele encodes delta-12 fatty acid desaturase proteins, which are exemplified in FIG. 2 and SEQ. ID. NOS. 5-7. In other embodiments, the *Brassica juncea* line may contain mutations at fad2-a and fad3-a gene loci and the resulting mutant alleles may encode one or more mutations in the sequence of the predicted BjFAD2-A and BjFAD3-A proteins. Representative examples of fad2-a and fad3-a mutated genes and proteins suitable for use in the present invention also include, but are not limited to, those disclosed in: International Publication No. WO 2006/079567 A2 (e.g., FIGS. 1 and 2), such as SEQ ID NOS:8 and 9; International Publication No. WO 2007/107590 A2, such as SEQ ID NOS: 10-21; U.S. Pat. No. 6,967,243 B2 (e.g., FIGS. 2 and 3), such as SEQ ID NOS:22-27; and European Publication No. 1 862 551 A1 (e.g., FIGS. 1 through 10), such as SEQ ID NOS:28-39. The contents of each of the foregoing patent publications is incorporated by reference herein. In alternative embodiments, BNfad2-a and Bnfad23-a converted lines can be used to look for the natural variation in BJFAD2B and BJFAD3B in *Brassica* plants, since significant variation in fatty acid profiles in BnFad2A, BnFad3A containing *Brassica juncea* plants can be detected.

In one aspect of the invention, it has unexpectedly been discovered that the substitution, deletion or silencing of FAD2 and/or FAD3 enzyme activity in a *Brassica* plant yields plants capable of producing an oil having oleic acid content of greater than about 70% by weight and a linolenic acid content of less than about 5% by weight. In another embodiment, it has unexpectedly been discovered that moving or transferring genes modifying FAD2 and/or FAD3 enzyme activity in a *Brassica* plant yields plants capable of producing an oil having oleic acid content of greater than about 70% by weight and a linolenic acid content of less than about 5% by weight. Such plants may, for example, be tetraploid plants or amphidiploid plants, such as *Brassica juncea* or *Brassica napus*. In one aspect, the invention accordingly provides for the deletion or silencing of selected FAD2 and FAD3 coding sequences in a plant, such as in lines of *Brassica juncea*. Edible oil derived from plants of the invention may be characterized by one or more of the following characteristics: an oleic acid content of at least 70% by weight, a linolenic acid content of less than about 5% by weight, and a total saturated fatty acid content of less than about 7% by weight.

Alternative aspects of the invention include plants and plant parts. As used herein, "plant parts" includes plant cells, seeds, pollen bearing the nucleic acids of the invention or having the fad2/fad3 coding sequences of the invention or having regulatory sequences, such as sequences upstream of FAD2/FAD3 coding regions, that express FAD2 and/or FAD3 enzymes from Brassica napus. Methods are provided for using the plants of the invention, including progeny plants selected by markers of the invention, to obtain plant products. As used herein, "plant products" includes anything derived from a plant of the invention, including plant parts such as seeds, meals, fats or oils, including plant products having altered oleic acid and linolenic acid concentrations. Methods are provided for modifying plants so that they have transferred fad2/fad3 coding sequences from Brassica napus capable of expressing an active FAD2 enzyme and/or FAD3 enzyme. Such methods may for example involve transferring one or more of the fad2-a and/or fad3-a coding sequences from Brassica napus in a plant through interspecific hybridization, so that the plant has substituted fad2 and/or fad3 coding sequences. Such methods allow identification and precise introgression of derived mutations into Brassica juncea.

Amplification primers for identifying portions of the fad2/fad3 coding sequences of the invention are provided, which may be used for example to distinguish different alleles of a selected FAD2 and/or FAD3 locus. Methods are provided for obtaining plants using the fad2/fad3 coding sequences of the invention, or regions upstream of the fad2/fad3 coding sequences of the invention. For example, sequences of the invention may be used to guide or target site-specific mutations that may down-regulate or alter expression of selected FAD2 and/or FAD3 coding sequences, such as by down-regulating or altering the expression of a FAD2 and/or FAD3 gene from a selected FAD2 or FAD3 locus, or by truncating the FAD2 and/or FAD3 protein encoded by the FAD2 and/or FAD3 gene. Conventional plant breeding techniques such as crossing and backcrossing and other breeding techniques may be used to introduce the fad2 and/or fad3 coding sequences of the invention into progeny of the plants of the invention.

An alternative embodiment includes an oil in seeds of a Brassica juncea variety has a fatty acid content comprising at least 68.0% oleic acid by weight and less than 4.0% linolenic acid by weight.

The present invention further includes meal obtained from seeds of B. juncea plants described herein, where such meal may be in the form of crushed seeds, press cake, white flake, or the meal from conventional crushing and solvent extraction processes.

In addition to the exemplary aspects and embodiments described above, further aspects and embodiments will become apparent by reference to the drawings and by study of the following descriptions.

BRIEF DESCRIPTION OF THE DRAWINGS

FIG. 1 illustrates partial genomic nucleotide sequences of the fad2 gene cloned from DMS100 and Quantum. The top is DMS100 sequence (SEQ ID NO:1) and bottom is Quantum sequence (SEQ ID NO:2). The arrowhead indicates a single nucleotide mutation of C to T, which resulted in a stop codon (TAG) (shaded). The forward and reverse primers for PCR-based mutant allele-specific marker are bolded and underlined.

FIG. 2 provides amino acid sequences of the fad2 gene, degenerated from the genomic nucleotide sequence cloned from DMS100 (SEQ ID NO:5), Quantum (SEQ ID NO:6), and from a published Brassica napus FAD2 gene (BNFAD2) (SEQ ID NO:7). The arrowhead indicates the position of the stop codon resulting from a single nucleotide mutation (C to T) in DMS100.

FIG. 3 shows genomic nucleotide sequences of the fad3c gene cloned from DMS100 and Quantum. The top is the DMS100 sequence (SEQ ID NO:3) and the bottom is the Quantum sequence (SEQ ID NO:4). Exons are boxed, introns are unboxed, which correspond to exons 4, 5, 6 and 7 and introns 4, 5 and 6 of the fad3 gene in Brassica rapa and Arabidopsis. The arrowhead indicates a single nucleotide mutation of G to A. The forward and reverse primers for PCR-based mutant allele-specific marker are bolded and underlined.

SEQUENCE LISTING

Figure 4:
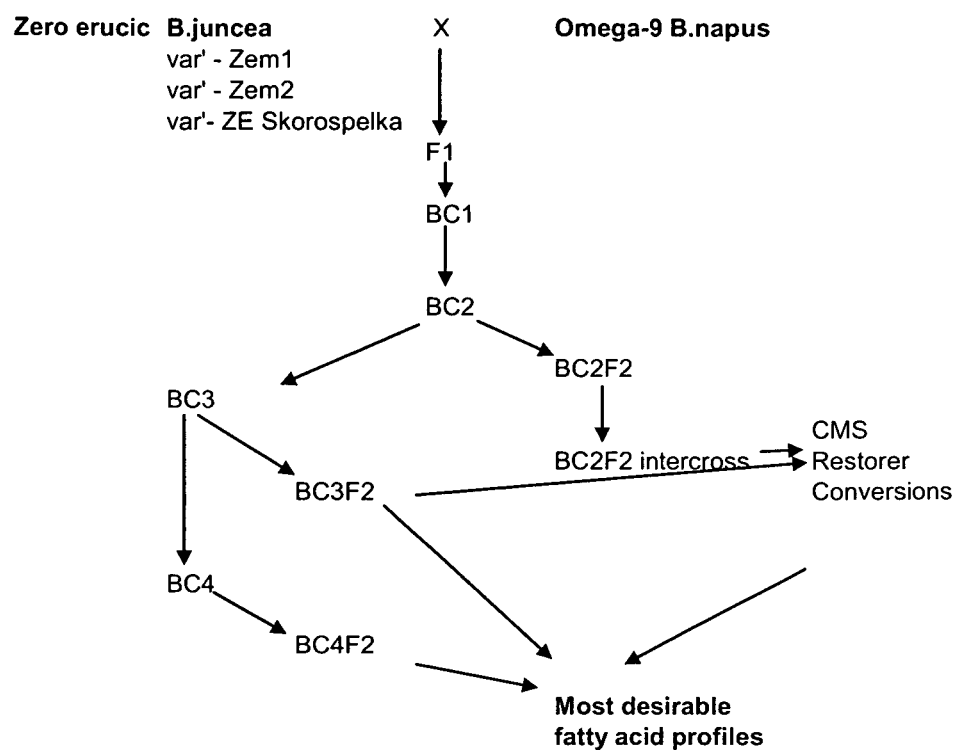
FIG. 4 illustrates one or more backcrosses (BC3 and BC4) between the high oleic-low linolenic selections and B. juncea parents (Zem1, Zem2 and ZE Skorospelka) according to principles of the present invention.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NO:1 shows a FAD2 gene cloned from Brassica napus variety, DMS100, referred to as SEQ ID NO:7 in International Publication No. US 2006/0248611 A1.

SEQ ID NO:2 shows a FAD2 gene cloned from B. napus variety, Quantum, referred to as SEQ ID NO:9 in International Publication No. US 2006/0248611 A1.

SEQ ID NO:3 shows a FAD3 gene cloned from B. napus variety, DMS100, referred to as SEQ ID NO:12 in International Publication No. US 2006/0248611 A1.

SEQ ID NO:4 shows a FAD3 gene cloned from B. napus variety, Quantum, referred to as SEQ ID NO:13 in International Publication No. US 2006/0248611 A1.

SEQ ID NO:5 shows the amino acid sequence of a delta-12 fatty acid desaturase protein encoded by a FAD2 gene cloned from B. napus variety, DMS100, referred to as SEQ ID NO:8 in International Publication No. US 2006/0248611 A1.

SEQ ID NO:6 shows the amino acid sequence of a delta-12 fatty acid desaturase protein encoded by a FAD2 gene cloned from B. napus variety, Quantum, referred to as SEQ ID NO:10 in International Publication No. US 2006/0248611 A1.

SEQ ID NO:7 shows the amino acid sequence of a delta-12 fatty acid desaturase protein encoded by a published FAD2 gene (Bnfad2) cloned from B. napus, referred to as SEQ ID NO:11 in International Publication No. US 2006/0248611 A1.

SEQ ID NO:8 shows a mutant fad2-a gene, as disclosed in International Publication No. WO 2006/079567 A2.

SEQ ID NO:9 shows the mutant fad2-a protein encoded by SEQ ID NO:8.

SEQ ID NO:10 shows a fad2-a gene from B. napus, referred to as SEQ ID NO:1 in International Publication No. WO 2007/107590 A2.

SEQ ID NO:11 shows the amino acid sequence of the fad2-a protein encoded by SEQ ID NO:10.

SEQ ID NO:12 shows a fad2-a gene from *B. napus*, referred to as SEQ ID NO:3 in International Publication No. WO 2007/107590 A2.

SEQ ID NO:13 shows the amino acid sequence of the fad2-a protein encoded by SEQ ID NO:12.

SEQ ID NO:14 shows a fad2-a gene from *B. napus*, referred to as SEQ ID NO:5 in International Publication No. WO 2007/107590 A2.

SEQ ID NO:15 shows the amino acid sequence of the fad2-a protein encoded by SEQ ID NO:14.

SEQ ID NO:16 shows a fad2-a gene from *B. napus*, referred to as SEQ ID NO:7 in International Publication No. WO 2007/107590 A2.

SEQ ID NO:17 shows the amino acid sequence of the fad2-a protein encoded by SEQ ID NO:16.

SEQ ID NO:18 shows a fad2-a gene from *B. napus*, referred to as SEQ ID NO:9 in International Publication No. WO 2007/107590 A2.

SEQ ID NO:19 shows a fad2-a gene from *B. napus*, referred to as SEQ ID NO:10 in International Publication No. WO 2007/107590 A2.

SEQ ID NO:20 shows a fad2-a gene from *B. napus*, referred to as SEQ ID NO:11 in International Publication No. WO 2007/107590 A2.

SEQ ID NO:21 shows a fad2-a gene from *B. napus*, referred to as SEQ ID NO:12 in International Publication No. WO 2007/107590 A2.

SEQ ID NO:22 shows a mutant "Fad2-D" gene from *B. napus*, referred to as SEQ ID NO:11 in U.S. Pat. No. 6,967,243.

SEQ ID NO:23 shows the amino acid sequence encoded by SEQ ID NO:22, referred to as SEQ ID NO:12 in U.S. Pat. No. 6,967,243.

SEQ ID NO:24 shows a mutant "Fad2-F" gene from *B. napus*, referred to as SEQ ID NO:15 in U.S. Pat. No. 6,967,243.

SEQ ID NO:25 shows the amino acid sequence encoded by SEQ ID NO:24, referred to as SEQ ID NO:16 in U.S. Pat. No. 6,967,243.

SEQ ID NO:26 shows a mutant "Fad2-F" gene from *B. napus*, referred to as SEQ ID NO:17 in U.S. Pat. No. 6,967,243.

SEQ ID NO:27 shows the amino acid sequence encoded by SEQ ID NO:26, referred to as SEQ ID NO:18 in U.S. Pat. No. 6,967,243.

SEQ ID NO:28 shows mutant *B. napus* fad2 genes, referred to as SEQ ID NO:22 in European Patent Publication No. 1 862 551 A1.

SEQ ID NO:29 shows mutant *B. napus* fad2 gene products, referred to as SEQ ID NO:23 in European Patent Publication No. 1 862 551 A1.

SEQ ID NO:30 shows a mutant *B. napus* fad2-a gene, referred to as SEQ ID NO:24 in European Patent Publication No. 1 862 551 A1.

SEQ ID NO:31 shows the amino acid sequence encoded by the mutant *B. napus* fad2-a gene of SEQ ID NO:30, which amino acid sequence is referred to as SEQ ID NO:25 in European Patent Publication No. 1 862 551 A1.

SEQ ID NO:32 shows a mutant *B. napus* fad2-a gene, referred to as SEQ ID NO:26 in European Patent Publication No. 1 862 551 A1.

SEQ ID NO:33 shows the amino acid sequence encoded by the mutant *B. napus* fad2-a gene of SEQ ID NO:32, which amino acid sequence is referred to as SEQ ID NO:27 in European Patent Publication No. 1 862 551 A1.

SEQ ID NO:34 shows a mutant *B. napus* fad2-a gene, referred to as SEQ ID NO:28 in European Patent Publication No. 1 862 551 A1.

SEQ ID NO:35 shows the amino acid sequence encoded by the mutant *B. napus* fad2-a gene of SEQ ID NO:34, which amino acid sequence is referred to as SEQ ID NO:29 in European Patent Publication No. 1 862 551 A1.

SEQ ID NO:36 shows a mutant *B. napus* fad2-a gene, referred to as SEQ ID NO:30 in European Patent Publication No. 1 862 551 A1.

SEQ ID NO:37 shows the amino acid sequence encoded by the mutant *B. napus* fad2-a gene of SEQ ID NO:36, which amino acid sequence is referred to as SEQ ID NO:31 in European Patent Publication No. 1 862 551 A1.

SEQ ID NO:38 shows a mutant *B. napus* fad2-a gene, referred to as SEQ ID NO:32 in European Patent Publication No. 1 862 551 A1.

SEQ ID NO:39 shows the amino acid sequence encoded by the mutant *B. napus* fad2-a gene of SEQ ID NO:38, which amino acid sequence is referred to as SEQ ID NO:33 in European Patent Publication No. 1 862 551 A1.

DETAILED DESCRIPTION OF THE INVENTION

For clarity of description, some of the terminology used herein is explained as follows.

The term "line" refers to a group of plants that displays very little overall variation among individuals sharing that designation. A "line" generally refers to a group of plants that display little or no genetic variation between individuals for at least one trait. A "DH (doubled haploid) line," as used in this application refers to a group of plants generated by culturing a haploid tissue and then doubling the chromosome content without accompanying cell division, to yield a plant with the diploid number of chromosomes where each chromosome pair is comprised of two duplicated chromosomes. Therefore, a DH line normally displays little or no genetic variation between individuals for traits.

A "variety" or "cultivar" is a plant line that is used for commercial production which is distinct, stable and uniform in its characteristics when propagated.

A "doubled haploid" (DH) line refers to a line created by the process of microspore embryogenesis, in which a plant is created from an individual microspore. By this process, lines are created that are homogeneous, i.e., all plants within the line have the same genetic makeup. The original DH plant is referred to as DH1, while subsequent generations are referred to as DH2, DH3 etc. Doubled haploid procedures are well known and have been established for several crops. A procedure for *Brassica juncea* has been described by Thiagrarajah and Stringham (1993) (A comparison of genetic segregation in traditional and microspore-derived populations of *Brassica juncea* in: L. Czern and Coss. *Plant Breeding* 111:330-334).

The term "high oleic" refers to *Brassica juncea* or other *Brassica* species as the context may dictate, with an oleic acid content higher than that of a wild-type or other reference variety or line, more generally it indicates a fatty acid composition comprising at least 70.0% by weight oleic acid.

"Total saturates" refers to the combined percentages of palmitic (C16:0), stearic (C18:0), arachidic (C20:0), behenic (C22:0) and tetracosanoic (C24:0) fatty acids. The fatty acid concentrations discussed herein are determined in accordance with standard procedures well known to those skilled in the art. Specific procedures are elucidated in the examples. Fatty acid concentrations are expressed as a percentage by weight of the total fatty acid content.

"Half-seed" analysis refers to a procedure whereby fatty acid analysis is carried out on one cotyledon (half-seed) and the remaining half-seed is used to form a plant if the results of the analysis are positive.

"Mutagenesis" is a process in which an agent known to cause mutations in genetic material is applied to plant material. In the experimental work, the mutagenic agent used was ethyl methylsulfonate (EMS). The purpose is to cause new genetic variability in a species and is usually done with a specific trait in mind. An example of mutagenesis used on haploids to induce novel variation has been described by Swanson et al., (*Plant Cell Rep*. 7:83-87, 1988). The disclosure of this article is herein incorporated by reference. It will be appreciated that a range of other techniques such as recombination with foreign nucleic acid fragments may be suitable to generate mutants and that by using certain techniques the generation of mutants may be directed at specific nucleotide or amino acid changes rather than being entirely random. All such methods of introducing nucleic acid sequence changes are understood to be included within the teen "mutagenesis" as used herein.

"Regeneration" involves the selection of cells capable of regeneration (e.g., seeds, microspores, ovules, pollen, vegetative parts) from a selected plant or variety. These cells may optionally be subjected to mutagenesis, following which a plant is developed from the cells using regeneration, fertilization, and/or growing techniques based on the types of cells mutagenized. Applicable regeneration techniques are known to those skilled in the art; see, for example, Pua et al., *Bio/Technology* 5:815-817 (1987); Jain et al., *Euphytica* 40:75-81 (1989); Szarejko et al., *Proceedings of an International Symposium on the Contribution of Plant Mutation Breeding to Crop Improvement*, 2:355-378 (1991); Cegielska-Taras and Szała, , *Rośliny Oleiste—Oilseed Crops*, XVIII, 21-30 (1997); Ferrie and Keller, *Proc. 9th International Rapeseed Congr*., Cambridge, 3:807-809 (1995); Martini et al., *Vortr. Pflanzenzüchtg*. 45:133-154 (1999); Swanson et al., *Theoretical and Applied Genetics*. 78:525-530 (1989); and Kirti and Chopra, *Plant Breeding* 102:1, 73-78 (1988), the disclosures of which are incorporated herein by reference. In this context, "M0" refers to untreated seeds; "M1" refers to the seeds exposed to mutagens and the resulting plants; "M2" is the progeny (seeds and plants) of self-pollinated M1 plants; "M3" is the progeny (seeds and plants) of self-pollinated M2 plants; "M4" is the progeny (seeds and plants) of self-pollinated M3 plants; "M5" is the progeny (seeds and plants) of self-pollinated M4 plants, and so on.

The term "stability" or "stable" as used herein with respect to a given genetically controlled fatty acid component means that the fatty acid component is maintained from generation to generation for at least two generations and preferably at least three generations at substantially the same level, e.g., preferably ±5%. The methods of the invention are capable of creating *Brassica juncea* lines with improved fatty acid compositions stable up to ±5% from generation to generation. It is understood by those of skill in the art that the above referenced stability may be affected by temperature, location, stress and time of planting. Thus, comparisons of fatty acid profiles between canola lines should be made using seeds produced under similar growing conditions.

When the term "*Brassica* plant" is used in the context of the present invention, this also includes any single gene conversions of that group. The term "single gene converted plant" as used herein refers to those *Brassica* plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing one or more times to the recurrent parent (identified as "BC1," "BC2," etc.). The parental *Brassica* plant which contributes the gene for the desired characteristic is termed the "non-recurrent" or "donor parent." This terminology refers to the fact that the non-recurrent parent is used one time in the backcross protocol and therefore does not recur. The parental *Brassica* plant to which the gene or genes from the non-recurrent parent are transferred is known as the recurrent parent as it is used for several rounds in the backcrossing protocol (Poehiman & Sleper, 1994; Fehr, 1987). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a *Brassica* plant is obtained wherein essentially all of the desired morphological and physiological characteristics of the recurrent parent are recovered in the converted plant, in addition to the single transferred gene from the non-recurrent parent as determined at the 5% significance level when grown under the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the non-recurrent parent, while retaining essentially all of the rest of the desired genetic material, and therefore the desired physiological and morphological, constitution of the original variety. The choice of the particular non-recurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

In some embodiments, antibodies against any of the polypeptides described herein or inferable herefrom may be employed to determine the presence or expression of one of the alleles disclosed and to distinguish between mutated and wild-type proteins or other mutants.

In this application "improved characteristics" means that the characteristics in question are altered in a way that is desirable or beneficial or both in comparison with a reference value or attribute, which may relate to the equivalent characteristic of a wild-type strain of *Brassica juncea*, or of whichever other *Brassica* line is under consideration. One possible wild-type *Brassica juncea* strain whose characteristics may be taken as a reference (or a control) is J96D-4830 but many others are possible and will readily be identified by those skilled in the art.

In this application "progeny" means all descendants including offspring and derivatives of a plant or plants and includes the first, second, third and subsequent generations and may be produced by self-pollination or crossing with plants with the same or different genotypes, and may be modified by a range of suitable genetic engineering techniques.

In this application "breeding" includes all methods of developing or propagating plants and includes both intra- and inter-species and intra- and inter-line crosses as well as all suitable conventional breeding and artificial breeding techniques. Desired traits may be transferred to other *Brassica juncea* lines through conventional breeding methods and can also be transferred to other *Brassica* species, such as *Brassica napus* and *Brassica rapa* through inter-specific crossing. Both conventional breeding methods and inter-specific crossing methods as well as other methods of transferring genetic material between plants are well documented in the literature.

In this application "molecular biological techniques" means all forms of manipulation of a nucleic acid sequence to alter the sequence and expression thereof and includes the insertion, deletion or modification of sequences or sequence fragments and the direct introduction of new sequences into the genome of an organism by directed or random recombination using any suitable vectors and/or techniques.

In this application "genetically derived" as used for example in the phrase "genetically derived from the parent lines" means that the characteristic in question is dictated wholly or in part by an aspect of the genetic makeup of the plant in question.

In this application the term "*Brassica*" may comprise any or all of the species subsumed in the genus *Brassica* including *Brassica napus, Brassica juncea, Brassica nigra, Brassica carinata, Brassica oleracea* and *Brassica rapa*.

Canola *Brassica juncea* as used in this application refers to *Brassica juncea* that produces seeds with oil and meal quality that meets the requirements for a commercial designation as "canola" oil or meal, respectively, (i.e., plants of *Brassica juncea* species that have less than 2% erucic acid (Δ13-22:1) by weight in seed oil and less than 30 micromoles of glucosinolates per gram of oil free meal).

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e., by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

All percentages of fatty acids herein refer to percentage by weight of total fatty acids of oil in which the fatty acid is a component. For example, reference to a plant having a 70% oleic acid content indicates that the fatty acid component of the oil comprises 70% oleic acid.

"Polymorphism" in a population refers to a condition in which the most frequent variant (or allele) of a particular locus has a population frequency which does not exceed 99%.

The term "heterozygosity" (H) is used when a fraction of individuals in a population have different alleles at a particular locus (as opposed to two copies of the same allele). Heterozygosity is the probability that an individual in the population is heterozygous at the locus. Heterozygosity is usually expressed as a percentage (%), ranging from 0 to 100%, or on a scale from 0 to 1.

"Homozygosity" or "homozygous" indicates that a fraction of individuals in a population have two copies of the same allele at a particular locus. Where plants are double haploid it is presumed that subject to any spontaneous mutations occurring during duplication of the haplotype, all loci are homozygous. Plants may be homozygous for one, several or all loci as the context indicates.

"Primers" are short polynucleotides or oligonucleotides required for a polymerase chain reaction that are complementary to a portion of the polynucleotide to be amplified. For example, the primer may be no more than 50 nucleotides long, preferably less than about 30 nucleotides long, and most preferably less than about 24 nucleotides long.

An "isolated" nucleic acid or polynucleotide as used herein refers to a component that is removed from its original environment (for example, its natural environment if it is naturally occurring). An isolated nucleic acid or polypeptide may contain less than 50%, less than 75%, less than 90%, and less than 99.9% or less than any integer value between 50 and 99.9% of the cellular components with which it was originally associated. A polynucleotide amplified using PCR so that it is sufficiently distinguishable (on a gel from example) from the rest of the cellular components may for example, be considered "isolated." The polynucleotides of the invention may be "substantially pure," i.e., having the highest degree of purity that can be achieved using a particular purification technique known in the art.

"Hybridization" refers to a process in which a strand of nucleic acid joins with a complementary strand through base pairing. Polynucleotides are "hybridizable" to each other when at least one strand of one polynucleotide can anneal to a strand of another polynucleotide under defined stringency conditions. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65°

C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

In one aspect, the invention provides *Brassica* plants, such as *Brassica juncea* plants, capable of producing seeds having an endogenous fatty acid content comprising a high percentage of oleic acid and low percentage of linolenic acid by weight. In particular embodiments, the oleic acid may comprise more than about 70.0%, 71.0%, 72.0%, 73.0%, 74.0%, 75.0%, 76.0%, 77.0%, 78.0%, 79.0%, 80.0%, 81.0%, 82.0%, 83.0%, 84.0% or 85.0%, including all integers and fractions thereof or any integer having a value greater than 85% of oleic acid. In particular embodiments, the linolenic acid content of the fatty acids may be less than about 5%, 4%, 3%, 2.5%, 2.0%, 1.5%, 1.0%, 0.5% or 0%, and including all integers and fraction thereof. In one exemplary embodiment, the plant is *Brassica juncea*, whose seeds have an endogenous fatty acid content comprising at least 70% oleic acid by weight and less than 3% linolenic acid by weight. In an additional embodiment, the plant is a *Brassica juncea* plant whose seeds have an endogenous fatty acid content comprising at least 70.0% oleic acid by weight and no more than about 5% linolenic acid by weight.

In one aspect, the invention provides *Brassica* plants, such as *Brassica juncea* plants, capable of producing seed having an endogenous fatty acid content comprising a high percentage of oleic acid and low percentage of linolenic acid by weight and low total saturated fatty acids or high total saturated fatty acids that may comprise less than about 5.5% total saturated fatty acids or >10% total saturated fatty acids, respectively, as shown in Table 11.

It is known that the composition of oil from seeds of *Brassica juncea* differs from that of *Brassica napus* in both fatty acid components (e.g., higher erucic acid content), essential oils (e.g., allyl isothiocyanate), and minor constituents (e.g., tocopherols, metals, tannins, phenolics, phospholipids, color bodies, and the like). Oils in seeds (including extracted oils) from *Brassica juncea* have been found to be higher in oxidative stability compared to oils from *Brassica napus*, even though oils from *Brassica juncea* typically have higher levels of C18:3. (C. Wijesundera et al., "Canola Quality Indian Mustard oil (*Brassica juncea*) is More Stable to Oxidation than Conventional Canola oil (*Brassica napus*)," *J. Am. Oil Chem. Soc.* (2008) 85:693-699).

In an alternative aspect, the invention provides methods for increasing the oleic acid content and decreasing the linolenic acid content of *Brassica* plants. Such methods may involve: (a) inducing mutagenesis in at least some cells from a *Brassica* line that has an oleic acid content greater than 55% and a linolenic acid content less than 14%; (b) regenerating plants from at least one of said mutagenized cells and selecting regenerated plants which have a fatty acid content comprising at least 70% oleic acid (or an alternative threshold concentration of oleic acid, as set out above) and less than 3% linolenic acid (or an alternative threshold concentration of linolenic acid, as set out above); and (c) deriving further generations of plants from said regenerated plants, individual plants of said further generations of plants having a fatty acid content comprising at least 70% oleic acid (or the alternative threshold concentration) and less than 3% linolenic acid (or the alternative threshold concentration). In some embodiments the *Brassica* may be *Brassica juncea*. The term "high oleic acid content" and "low linolenic content" encompasses the full range of possible values described above. In alternative embodiments, methods of the invention may further comprise selecting one or more of the lines, the regenerated plants and the further generations of plants for reduced linoleic acid content, such as the range of possible values described above. In further embodiments step (c) may involve selecting and growing seeds from the regenerated plants of step (b). In further embodiments, methods of the invention may comprise repetition of the specified steps until the desired oleic acid content, linolenic acid content, or both, are achieved.

In alternative embodiments, methods are provided for screening individual seeds for increased oleic acid content and decreased linoleic acid content, comprising: determining one or more of the oleic acid content; or the linoleic acid content; or the oleic acid content and the linoleic acid content of the fatty acids of a part of the germinant of the seed; comparing one or more of the contents with a reference value; and inferring the likely relative oleic acid, linoleic acid, or oleic and linoleic acid content of the seed. In particular embodiments the part of the plant used for analysis may be part or all of a leaf, cotyledon, stem, petiole, stalk or any other tissue or fragment of tissue, such as tissues having a composition that demonstrates a reliable correlation with the composition of the seed. In one series of embodiments the part of the germinant may be a part of a leaf. In certain embodiments the step of inferring the fatty acid composition of the seed may comprise assuming that a significantly changed level of a given acid in said leaf reflects a similar relative change in the level of that acid in the seed. In a particular embodiment of this invention, a method for screening *Brassica* plants for individual plant line whose seeds have an endogenous fatty acid content comprising at least 70% oleic acid and less than 3% linolenic acid by weight by analyzing leaf tissue. In addition, the leaf tissue can be analyzed for fatty acid composition by gas liquid chromatography, wherein the extraction of the fatty acids can occur by methods such as bulk-seed analysis or half-seed analysis.

In alternative embodiments, the invention provides *Brassica* plants, which may be *Brassica juncea* plants, comprising the previously described gene alleles from *Brassica juncea* lines. In certain embodiments, the plant may be homozygous at the fad2-a and fad3-a loci represented by the mutant alleles. In an additional embodiment, the *Brassica juncea* plant, plant cell, or a part thereof, contains the gene alleles having nucleic acid sequences from the previously described sequences disclosed herein.

In some embodiments, the invention may involve distinguishing the HOLL, canola quality *Brassica juncea* of the present invention (≥70% oleic acid and ≤5% linolenic acid) from the low oleic acid/high linolenic acid *Brassica juncea* (~45% oleic acid and ~14% linolenic acid) by examining the presence or absence of the BJfad2b gene (see for reference U.S. patent publication No. 20030221217, Yao et al.). This distinction may involve confirming that the BJfad2a gene is the only functional oleate fatty acid desaturase gene in a canola quality *Brassica juncea* line, as is known in the art.

In one embodiment, a *Brassica juncea* line contain fad2 and fad3 genes, as disclosed in International Publication No. US 2006/0248611 A1, the contents of which are incorporated by reference, which are exemplified in FIGS. 1 and 3 therein. The fad2 and fad3 genes are exemplified herein by SEQ ID NOS:1-4. The resulting alleles encode delta-12 fatty acid desaturase proteins, which are exemplified in FIG. 2 of International Publication No. US 2006/0248611 A1, and are further exemplified herein by SEQ. ID. NOS:5-7. In other embodiments, the *Brassica juncea* line may contain mutations at fad2-a and fad3-a gene loci and the resulting mutant alleles may encode one or more mutations in the sequence of the predicted BJFAD2-a and BJFAD3-a proteins. Representative examples of fad2-a and fad3-a mutated genes and proteins suitable for use in the present invention also include, but are not limited to, those disclosed in: International Publication No. WO 2006/079567 A2 (e.g., FIGS. 1 and 2), such as SEQ ID NOS:8 and 9; International Publication No. WO 2007/107590 A2, such as SEQ ID NOS:10-21; U.S. Pat. No. 6,967,243 B2 (e.g., FIGS. 2 and 3), such as SEQ ID NOS:22-27; and European Publication No. 1 862 551 A1 (e.g., FIGS. 1 through 10), such as SEQ ID NOS:28-39. The contents of each of the foregoing patent publications is incorporated by reference herein.

Homology to sequences of the invention may be detectable by hybridization with appropriate nucleic acid probes, by PCR techniques with suitable primers or by any other commonly used techniques. In particular embodiments there are provided nucleic acid probes which may comprise sequences homologous to portions of the alleles of the invention. Further embodiments may involve the use of suitable primer pairs to amplify or detect the presence of a sequence of the invention, for example, a sequence that is associated with increased oleic acid content.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al., (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., (1988) *Gene* 73:237-244 (1988); Higgins et al., (1989) *CABIOS* 5:151-153; Corpet et al., (1988) *Nucleic Acids Res.* 16:10881-90; Huang et al., (1992) *CABIOS* 8:155-65; and Pearson et al., (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al., (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al., (1997) *Nucleic Acids Res.* 25:3389. Alternatively, PSI-BLAST (in BLAST 2.0) can be used to perform an iterated search that detects distant relationships between molecules. See Altschul et al., (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection. Alignments can also be performed using Sequencher™ software (from Gene Codes Corporation, Ann Arbor, Mich.) for identifying the homologies and variations, if any, between the aligned sequences.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al., (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

As used herein, the term "Omega-9" means, with respect to an oil profile from canola, a non-hydrogenated oil having a fatty acid content comprising at least 68.0% oleic acid by weight and less than or equal to 4.0% linolenic acid by weight. With respect to a canola plant, the term "Omega-9" means a canola plant producing seeds having an endogenous fatty acid content comprising at least 68.0% oleic acid by weight and less than 4.0% linolenic acid by weight.

In selected embodiments, the invention provides isolated DNA sequences comprising complete open reading frames (ORFs) and/or 5' upstream regions of the previously disclosed mutant fad2 and fad3 genes. The invention accordingly also provides polypeptide sequences of the predicted mutant proteins, containing mutations from the previously described mutant alleles. It is known that membrane-bound desaturases, such as FAD2, have conserved histidine boxes. Changes in amino acid residues outside these histidine boxes may also affect the FAD2 enzyme activity (Tanhuanpää et al., *Molecular Breeding* 4:543-550, 1998).

In one aspect of the invention, the mutant alleles described herein may be used in plant breeding. Specifically, alleles of the invention may be used for breeding high oleic acid *Brassica* species, such as *Brassica juncea, Brassica napus, Brassica rapa, Brassica nigra* and *Brassica carinata*. The invention provides molecular markers for distinguishing mutant alleles from alternative sequences. The invention thereby provides methods for segregation and selection analysis of genetic crosses involving plants having alleles of the invention. The invention thereby provides methods for segregation and selection analysis of progenies derived from genetic crosses involving plants having alleles of the invention.

In alternative embodiments, the invention provides methods for identifying *Brassica* plants, such as *Brassica juncea* plants, with a desirable fatty acid composition or a desired genomic characteristic. Methods of the invention may for example involve determining the presence in a genome of particular FAD2 and/or FAD3 alleles, such as the alleles of the invention or the wild-type J96D-4830/BJfad2a allele. In particular embodiments, the methods may comprise identifying the presence of a nucleic acid polymorphism associated with one of the identified alleles or an antigenic determinant associated with one of the alleles of the invention. Such a determination may for example be achieved with a range of techniques, such as PCR amplification of the relevant DNA fragment, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variants or wild-type forms of that protein. This invention also provides a method for identifying *B. juncea* plants, whose seeds have an endogenous fatty acid content comprising at least 70% oleic acid by weight, by determining the presence of the mutant alleles of the invention.

In some of the selected embodiments, specific single basepair changes of the mutant alleles of the invention may be used to design an allele-specific PCR primer, for example making use of a 3' mismatch. Various primer combinations can be made, such as forward primers or reverse primers with a "G/C" at the 3' end (for amplifying that wild-type allele) or an "A/T" at the 3' end (for amplifying the mutant allele). In other selected embodiments, specific single basepair changes of the mutant alleles of the invention may be used to design an allele-specific PCR primer, for example making use of a 3' mismatch. Various primer combinations can be made, such as forward primers or reverse primers with a "C/G" at the 3' end (for amplifying that wild-type allele) or a "T/A" at the 3' end (for amplifying the mutant allele). For an exemplary summary of allele-specific PCR protocols, see Myakishev et al., 2001, *Genome Research* 11: 163-169, or Tanhuanpää et al., 1999, *Molecular Breeding* 4: 543-550.

In alternative embodiments, various methods for detecting single nucleotide polymorphisms (SNPs) may be used for identifying alleles of the invention. Such methods may, for example, include TaqMan assays or Molecular Beacon assays (Tapp et al., *BioTechniques* 28:732-738), Invader Assays (Mein et al., *Genome Research* 10:330-343, 2000), Illlumina® Golden Gate Assays (www.illumina.com), or assays based on single strand conformational polymorphisms (SSCP) (Orita et al., *Proc. Natl. Acad. Sci. U.S.A.* 86:2766-2770, 1989).

In alternative embodiments, the invention provides *Brassica* plants comprising fad2 and fad3 coding sequences that encode mutated FAD2 and FAD3 proteins. Such mutated FAD2/FAD3 proteins may contain only one amino acid change compared to the wild-type FAD2 protein. In representative embodiments, various *Brassica juncea* lines contain the previously described mutated FAD2 proteins, encoded by the previously described alleles. Such alleles may be selected to be effective to confer an increased oleic acid content and reduced linolenic acid content on plants of the invention. In particular embodiments, the desired allele may be introduced into plants by breeding techniques. In alternative embodiments, alleles of the invention may be introduced by molecular biological techniques, including plant transformation. In such embodiments, the plants of the invention may produce seed having an endogenous fatty acid content comprising: at least about 70% oleic acid by weight and less than about 3% linolenic acid by weight, or any other oleic acid and linolenic acid content threshold as set out above. Plants of the invention may also contain from about 70% to about 85% by weight oleic acid, from about 70% to about 78% oleic acid, and from about 0.1% to about 3% linoleic acid, wherein the oil composition is genetically derived from the parent line. Plants of the invention may also have a total fatty acid content of from less than 7.1% to less than about 6.2% by weight. In one embodiment, the plant produces seed having an endogenous fatty acid content comprising at least about 70% of oleic acid and less than 3% of linoleic acid, wherein the oil composition is genetically derived from the parent line.

In selected embodiments, the invention provides *Brassica* seed, which may be a *Brassica juncea* seed, having an endogenous oil content having the fatty acid composition set out for one or more of the foregoing embodiments and wherein the genetic determinants for endogenous oil content are derived from the mutant alleles of the invention. Such seeds may, for example, be obtained by self-pollinating each of the mutant allele lines of the invention. Alternatively, such seeds may for example be obtained by crossing the mutant allele lines with a second parent followed by selection, wherein the second parent can be any other *Brassica* lines such as a *Brassica juncea* line, being a canola quality *Brassica juncea* or a non-canola quality *Brassica juncea*, or any other *Brassica* species such as *Brassica napus, Brassica rapa, Brassica nigra*, and *Brassica carinata*. These breeding techniques are well known to persons having skill in the art.

In alternative embodiments the invention provides genetically stable plants of the genus *Brassica*, such as *Brassica juncea* plants that develop mature seeds having a composition disclosed in one or more of the foregoing embodiments. Such plants may be derived from *Brassica juncea* lines having mutant alleles of the invention. The oil composition of such plants may be genetically derived from the parent lines.

In alternative embodiments the invention provides processes of producing a genetically stable *Brassica* plant, such as a *Brassica juncea* plant, that produces mature seeds having an endogenous fatty acid content comprising the composition specified for one or more of the foregoing embodiments. Processes of the invention may involve the steps of: crossing Omega-9 genes (e.g., fad2a and fad3a) from *Brassica napus* with other *Brassica* plants, such as *Brassica juncea*, to form F1 progenies. The F1 progenies may be propagated, for example by means that may include self-pollination or the development of doubled haploid plants. By combining mutant FAD2 alleles and mutant FAD3 alleles, plants having double mutant gene alleles (fad2 and fad3) can have superior oil fatty acid profile than any single mutant plants. The resulting progenies may be subject to selection for genetically stable plants that generate seeds having a composition disclosed for one or more of the foregoing embodiments. Such seeds may, for example, have a stabilized fatty acid profile that includes a total saturates content of from about 7.1% to about 6.5% in total extractable oils. In certain variants, the progeny may themselves produce seeds or oil that has a composition as set out above for alternative embodiments.

Have an oleic acid content of greater than about 70% by weight and a linolenic acid content of less than about 3% by weight.

In selected embodiments, an increase in oleic acid in plants of the invention, such as plants derived from the mutant alleles of the present invention, may be accompanied by a corresponding decrease in linoleic acid and linolenic acid, while other fatty acids may remain virtually unchanged. Data illustrating such characteristics is shown in Tables 1, 6-10, and 12-14 herein. The original *Brassica juncea* background fatty acid data are shown in Table 2 and fatty acid data for BC2F2 half seed selected lines are shown in Tables 7, 8, and 10. Table 12 illustrates BC3F3 ½ seed data having fatty acid profiles with very high oleic acid and low linolenic acid, and additionally showing very low levels of linoleic acid. Table 14 illustrates BC3F4 seed data (FAME's on whole seed) for the lines that were shown in Table 12 (BC3F3 ½ seed selections, grown up and selfed and then 15 seed bulks tested). These results confirm the profiles found in Table 12 (BC3F3) and show that the profiles are stable.

In one aspect, the invention provides plants having a stable, heritable high oleic acid and low linolenic acid phenotype. For example, the high oleic acid and low linolenic acid phenotype resulting from the mutant alleles of the invention are genetically heritable through M2, M3, and M4 generations.

In various aspects, the invention involves the modulation of the number of copies of an expressible coding sequence in a plant genome. By "expressible" it is meant that the primary structure, i.e., sequence, of the coding sequence indicates that the sequence encodes an active protein. Expressible coding sequences may nevertheless not be expressed as an active protein in a particular cell. This "gene silencing" may for example take place by various mechanisms of homologous transgene inactivation in vivo. Homologous transgene inactivation has been described in plants where a transgene has been inserted in the sense orientation, with the unexpected result that both the gene and the transgene were down-regulated (Napoli et al., 1990 *Plant Cell* 2:279-289). The exact molecular basis for such co-suppression is unknown, although there are at least two putative mechanisms for inactivation of homologous genetic sequences. Transcriptional inactivation via methylation has been suggested as one mechanism, where duplicated DNA regions signal endogenous mechanisms for gene silencing. A post-transcriptional mechanism has also been suggested, where the combined levels of expression from both the gene and the transgene are thought to produce high levels of transcript which trigger threshold-induced degradation of both messages (van Bokland et al., 1994, *Plant J.* 6:861-877). In the present invention, the expressible coding sequences in a genome may accordingly not all be expressed in a particular cell.

In alternative embodiments, the invention provides *Brassica juncea* plants wherein the activity of a fatty acid desaturase is altered, the oleic acid content is altered, or the linolenic acid content is altered relative to wild-type *B. juncea* that was used for the mutagenesis experiment. By fatty acid desaturase ("FAD"), it is meant that a protein exhibits the activity of introducing a double bond in the biosynthesis of a fatty acid. For example, FAD2/FAD3 enzymes may be characterized by the activity of introducing the second double bond in the biosynthesis of linoleic acid from oleic acid. Altered desaturase activity may include an increase, reduction or elimination of a desaturase activity compared to a reference plant, cell or sample.

In other aspects, reduction of desaturase activity may include the elimination of expression of a nucleic acid sequence that encodes a desaturase, such as a nucleic acid sequence of the invention. By elimination of expression, it is meant herein that a functional amino acid sequence encoded by the nucleic acid sequence is not produced at a detectable level. Reduction of desaturase activity may include the elimination of transcription of a nucleic acid sequence that encodes a desaturase, such as a sequence of the invention encoding a FAD2 enzyme or FAD3 enzyme. By elimination of transcription it is meant herein that the mRNA sequence encoded by the nucleic acid sequence is not transcribed at detectable levels. Reduction of desaturase activity may also include the production of a truncated amino acid sequence from a nucleic acid sequence that encodes a desaturase. By production of a truncated amino acid sequence it is meant herein that the amino acid sequence encoded by the nucleic acid sequence is missing one or more amino acids of the functional amino acid sequence encoded by a wild-type nucleic acid sequence. In addition, reduction of desaturase activity may include the production of a variant desaturase amino acid sequence. By production of a variant amino acid sequence it is meant herein that the amino acid sequence has one or more amino acids that are different from the amino acid sequence encoded by a wild-type nucleic acid sequence. As discussed in more detail herein, the current invention discloses that the mutant lines of the invention produce FAD2 and FAD3 enzymes with variant amino acids compared to the wild-type line J96D-4830. A variety of types of mutation may be introduced into a nucleic acid sequence for the purpose of reducing desaturase activity, such as frame-shift mutations, substitutions and deletions.

In some embodiments, the invention provides new FAD2/FAD3 polypeptide sequences, which may be modified in accordance with alternative embodiments of the invention. It is well known in the art that some modifications and changes can be made in the structure of a polypeptide without substantially altering the biological function of that peptide to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made where the hydrophilicity value of the residues is significantly different, e.g., differing by more than 2.0.

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); H is (−3.2); Glu (−3.5); Gln (−3.5); Asp (−3.5); Asn (−3.5); Lys (−3.9); and Arg (−4.5). Non-conserved amino acid substitutions may be made where the hydropathic index of the residues is significantly different, e.g., differing by more than 2.0. For example, on this basis, the following amino acid substitutions for the wild-type H is (−3.2) at a position corresponding to amino acid 105 in BJfad2-a would be non-conserved substitutions: Ile (+4.5); Val (+4.2); Leu (+3.8); Phe (+2.8); Cys (+2.5); Met (+1.9); Ala (+1.8); Gly (−0.4); Thr (−0.7); Ser (−0.8); and Trp (−0.9).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made where the residues do not fall into the same class, for example substitution of a basic amino acid for a neutral or non-polar amino acid.

The present invention further includes meal obtained from seeds of *B. juncea* plants described herein, where such meal may be in the form of crushed seeds, press cake (seeds that that have been pressed to expel oils, but have not been subject to a solvent or other chemical extracts), white flake (seeds that have been crushed, and extracted with a solvent such as hexane to remove more oil), or the meal from conventional crushing and solvent extraction processes. In one particular embodiment, *B. juncea* seed is subjected to aqueous processing of the type described in, for example, WO2008024840 A2, WO03/053157, U.S. Pat. No. 5,844,086; WO 97/27761; U.S. Patent Application 2005/0031767, or J. Caviedes, "Aqueous Processing Of Rapeseed (Canola)," Thesis For Degree Of Master Of Applied Science, University Of Toronto 1996, pages 1-147.

Oils of the present invention may also be used in non-culinary or dietary processes and compositions. Some of these uses may be industrial, cosmetic or medical. Oils of the present invention may also be used in any application for which the oils of the present invention are suited. In general, the oils of the present invention may be used to replace, e.g., mineral oils, esters, fatty acids, or animal fats in a variety of applications, such as lubricants, lubricant additives, metal working fluids, hydraulic fluids and fire resistant hydraulic fluids. The oils of the present invention may also be used as materials in a process of producing modified oils. Examples of techniques for modifying oils of the present invention include fractionation, hydrogenation, alteration of the oil's oleic acid or linolenic acid content, and other modification techniques known to those of skill in the art. In some embodiments, oils of the present invention are used in the production of interesterified oils. Such compositions may be included in an electrical apparatus.

Examples of industrial uses for oils of the present invention include comprising part of a lubricating composition (U.S. Pat. No. 6,689,722; see also WO 2004/0009789A1); a fuel, e.g., biodiesel (U.S. Pat. No. 6,887,283; see also WO 2009/038108A1); record material for use in reprographic equipment (U.S. Pat. No. 6,310,002); crude oil simulant compositions (U.S. Pat. No. 7,528,097); a sealing composition for concrete (U.S. Pat. No. 5,647,899); a curable coating agent (U.S. Pat. No. 7,384,989); industrial frying oils; cleaning formulations (WO 2007/104102A1; see also WO 2009/007166A1); and solvents in a flux for soldering (WO 2009/069600A1). Oils of the present invention may also be used in industrial processes, for example, the production of bioplastics (U.S. Pat. No. 7,538,236); and the production of polyacrylamide by inverse emulsion polymerization (U.S. Pat. No. 6,686,417).

Examples of cosmetic uses for oils of the present invention include use as an emollient in a cosmetic composition; as a petroleum jelly replacement (U.S. Pat. No. 5,976,560); as comprising part of a soap, or as a material in a process for producing soap (WO 97/26318; U.S. Pat. No. 5,750,481; WO 2009/078857A1); as comprising part of an oral treatment solution (WO 00/62748A1); as comprising part of an ageing treatment composition (WO 91/11169); and as comprising part of a skin or hair aerosol foam preparation (U.S. Pat. No. 6,045,779).

Additionally, the oils of the present invention may be used in medical applications. For example, oils of the present invention may be used in a protective barrier against infection (Barclay and Vega, "Sunflower oil may help reduce nosocomial infections in preterm infants." Medscape Medical News on the world wide web at cme.medscape.com/viewarticle/501077, accessed Sep. 8, 2009); and oils high in omega-9 fatty acids may be used to enhance transplant graft survival (U.S. Pat. No. 6,210,700).

It should be understood that the foregoing are non-limiting examples of non-culinary uses for which the oils of the present invention are suited. As previously stated, oils and modified oils of the present invention may be used to replace, e.g., mineral oils, esters, fatty acids, or animal fats in all applications known to those of skill in the art.

It is understood that various modifications and alternatives can be made to the present invention. Certain specific embodiments thereof are described in the general methods and further explained by the following examples. The invention certainly applies to all canola quality *Brassica juncea* species as well as all non-canola quality *Brassica juncea* species. The invention may be applied to all other *Brassica* species including *Brassica juncea*, *Brassica nigra*, and *Brassica carinata*, to produce substantially similar results. It should also be understood that the following examples are not intended to limit the invention to particular fauns disclosed, but instead, the invention is to cover all modifications, equivalents and alternatives falling within the scope of the invention.

EXAMPLES

Example 1

Backcrossing

Referring to FIG. 1, one or more backcrosses (BC3 and BC4) between the high oleic-low linolenic selections and *B. juncea* parents (Zem1, Zem2 and ZE Skorospelka) in order to fully recover *B. juncea* genetic background. Only zero erucic *B. juncea* lines were used in the backcrossing program since this would allow for full expression of the fad2 and fad3 mutant alleles in a non competitive situation with the FAE gene(s).

After each advanced back-cross (for example BC3, BC4) and subsequent self pollination (for example BC3F2, BC4F2), progeny seed is subjected first to tissue screening for presence of fad2a and fad3a genes (using markers as described in more detail herein), then grown on to flowering to be used in the subsequent backcrosses. Harvested seed from selected lines is subjected to oil profile analysis using half seed, non-destructive single whole seed NIR analysis, or single seed NIR (FTNIR). Subsequently, samples containing increased oleic levels, and reduced linolenic levels are planted in the soil and are grown to maturity. Selfed seed are produced from these plants and bulk seeds are analyzed for oil profile representing the high oleic and low linolenic acid. Selections are identified that have within a range of 67-80% oleic acid, and less than 5% linolenic acid. These selections were intercrossed among themselves to create the desired fatty acid profile.

Genomic DNA from leaf tissues were isolated and screened for presence of mutations specific to fad2a and fad3a genes known to confer high oleic acid and low linolenic acid phenotypes in seed oil. Plants closely resembled in its phenotype (leaf shape and texture) that of *B. juncea* parent. Plants also exhibited pod shattering resistance and drought tolerance under field conditions similar to parental *B. juncea*.

SSR markers specific to CC genome and undesirable AA genome regions are no longer represented in the *B. juncea* x *B. napus* backcross to *B. juncea* progeny.

Leaf tissue collected from *B. juncea* and Omega-9 *B. napus* lines were lyophilized for genetic fingerprinting. In cases where multiple plants were used to generate F1 individuals, tissue from all progenitors was also collected to account for alleles that may be observed in subsequent generations. If parental tissue was not collected, an alternative option was implemented where a random sample of six plants from each parental seed lot (source) was collected. DNA was isolated from up to six individuals per line and equal aliquots from each individual were pooled to form a parental control for genetic fingerprinting. Genetic fingerprints of all Omega-9 *B. napus* lines used in the crossing program were previously established and represent data collected from across all A genome and C genome linkage groups in these lines.

In order to further improve the interpretation and validity of the results, leaf tissue was collected, DNA isolated and DNA sample pools were also prepared for *B. rapa*, *B. nigra*, and *B. oleracea* accession(s) for the purpose of putatively identifying alleles corresponding to the A, B, and C genomes, respectively.

*B. juncea*, *B. napus*, *B. rapa*, *B. nigra*, and *B. oleracea* pools are screened with a panel of SSR markers. In addition to collecting information on observed DNA fragments, information on null alleles is noted. Collected genotyping information is stored in a Geneflow™ genotyping database. Identification of informative SSR markers for the selected *B. juncea* and *B. napus* lines is accomplished using the Geneflow™ genotyping database polymorphism reporting function.

Marker-assisted selection to reduce genomic regions specific to *B. napus* is carried out in backcross generations by screening the backcross populations with polymorphic SSR markers identified through parental screening. In addition to polymorphic co-dominant markers, markers scoring null for the *B. juncea* lines are also used for marker assisted selection for desired A and B genome regions. Selection of plants for advancement is done by breeding and laboratory focal points using both phenotype and genotype observations. The progeny plants that do not have the Omega-9 *B. napus* CC genome, as well as the undesirable AA genome segments, based on the marker profiles, are chosen for advancing to the next step.

Example 2

Development of *B. Juncea*-Specific Markers

DNA Markers are developed that can detect presence of the BB genomic DNA relevant to FAD2b and other available sequences from *B. nigra* and *B. juncea* (representing the BB genome). Double haploid mapping populations are developed for marker development. In addition, DNA (SSR and SNP) markers are developed from the known B-genome sequences. These markers are able to confirm the extent of recovery of *B. juncea* background in the converted lines.

A total of 1931 *B. napus* SSR markers, predominantly containing, di- and tri-nucleotide repeat motifs, are available for parental screening. These markers are currently being screened on a panel of *Brassica* lines that belong to *B. juncea* (Zem1, Zem2 and ZE Skorospelka lines), Omega-9 *B. napus*, *B. rapa*, *B. nigra*, and *B. oleracea*. This screening provides two types of information. First, since these SSR markers were developed from *B. napus* genome, the screening provides information on their utility in other genomes and permits identification of alleles corresponding specifically to the AA, BB, or CC genomes. Second, the screening permits identification of a core set of markers for use in *B. juncea* mapping and trait introgression.

In addition to the markers mentioned above, public databases were searched for SSR markers that can be used for *B. juncea*. A total of 438 public SSRs were identified, of which 101 are from *B. napus* (AA CC genome), 113 from *B. nigra* (BB genome), 95 from *B. oleracea* (CC genome) and 129 from *B. rapa* (AA genome). Out of these, 113 SSRs from *B. nigra*, 129 SSRs from *B. rapa*, and some of the SSRs from *B. napus* were identified as being potentially useful in *B. juncea*.

Selected markers from our current collection, as well as SSR and SNP markers developed from known B-genome sequences, are used to confirm the presence of *B. juncea* background in backcross breeding. Informative markers identified from the parent screening are also used to construct a *B. juncea* linkage map, as well as a comparative map between *B. juncea* and *B. napus* to identify shared marker loci. Introgressed fad2a and fad3a loci are mapped in *B. juncea* to provide proof that they have been successfully introgressed into the AA genome of *B. juncea*.

Through use of these *B. juncea*-specific markers, inherent mutant fad2a, fad2b, fad3a, and fad3b sequences are identified to locate fad2 and fad3 variations in selected lines with improved fatty acid profiles.

Table 3 shows interspecific hybridization results between seven (7) *B. juncea* and three (3) Omega-9 *B. napus* inbred lines. Table 4 shows *B. juncea*/Omega-9 *B. napus* (F1 interspecific hybrid) FAD marker screening results. Table 5 shows *B. juncea*//*B. juncea*/Omega-9 *B. napus* (BC1) GOI screening results. Table 6 shows *B. juncea*\*2//*B. juncea*/Omega-9 *B. napus* (BC2F1) GOI screening results.

Example 3

Recovery and Determination of B Genome

Self-pollinated and doubled haploid plants exhibiting seed oil profile of high oleic and low linolenic acids, as previously described, are screened using the markers selected for the BB genome. The BB genome is continued present in the converted lines. These mutant *B. juncea* lines also show a decrease (or complete absence of) in the number of positive C genome markers selected for *B. napus*. These profiles are further enhanced by additional backcrosses and selfing techniques known in the art which improve the agronomics of the line, e.g., reduce yield drag, reduce pod shatter, alter maturity for various growing zones, increase stress tolerance, increase disease resistance, and the like.

Three different methods are used for the determination of B genome in the self-pollinated and DH progeny from *B. napus* and *B. juncea* interspecific crosses exhibiting desired seed oil profile.

A) Molecular Markers

Molecular markers capable of detecting genetic polymorphisms between *B. napus* and *B. juncea* lines are identified. A total of 1931 *B. napus* SSR markers were screened to identify a core set of SSRs that can distinguish between *B. juncea* genome and *B. napus*. In addition, as described in Example 2, public databases were searched to identify additional markers for parental screening. Thus, more than 2,300 SSR markers were investigated for their ability to discriminate *B. juncea* vs. *B. napus*. A set of markers from this screening is used for determining the enrichment of *B. juncea* genome in the progeny or the diminishing or absence of *B. napus* genome. Another marker system includes the use of SNP markers. More than 3,000 SNPs have been developed through a consortium. Two high throughput Illumina assays are generated (i.e., two 1536-plex SNP OPAs (Oligo Pool All)). Both of these OPAs (a total of 3,072 SNP assays) are screened on the parental panel consisting of lines of all three tetraploids *B. napus*, *B. juncea* and *B. carinata*, and all three diploid progenitors of the *Brassica* "Triangle of U" (1935)—*B. nigra*, *B. oleracea* and *B. rapa*. A set of SNPs are identified that can unambiguously track *B. juncea* fragments in the progeny. Specifically those SNPs that can confirm the presence of B genome in the progeny are included in the set. Thus, by using a large number of informative SSRs and SNPs for the screening of progeny plants, those plants that have a high percentage of B genome are identified. Following characterization of self-pollinated and DH progeny, mapping positions of marker loci are validated against *B. napus* and *B. juncea* linkage maps by constructing a comparative map using segregating progeny. The comparative map allows for identification of potential marker loci re-arrangement, addition, or deletion following interspecific mating.

B) Fluorescence In Situ Hybridization

Fluorescence In Situ Hybridization (FISH) technique is used to determine the presence and enrichment of B genome in the progeny. The progeny plants are used both for marker analysis and for cytological studies, such as identification of chromosome number, occurrence of aneuploidy and for the determination of genomic segments of interest. FISH is a powerful tool than can further reinforce the information obtained by molecular markers. To this end, candidate SSR and SNP marker sequences that can unambiguously determine the presence of B genome are used to pull out large BAC clones which are then used as probes on metaphase spreads of the candidate progeny plants identified as having high percentage of B genome. BAC sequences are also identified using computational methods, provided the BAC sequences are available in the databases. If this is the case, the BACs identified in silico can be obtained from the respective source and used in the FISH experiments.

C) Genome In Situ Hybridization

Genome In Situ Hybridization (GISH) technique is used where chromosomes of the candidate progeny plants can be probed with total nuclear BB genome DNA using total *B. juncea* DNA as the competing unlabeled probe. A strong hybridization to BB genome chromosomes in *B. juncea* indicates the presence of BB genome in the progeny.

Samples with the desired seed oil profile and alleles attributed to *B. juncea* are used for backcrossing and additional self-pollination. In segregating populations, MAS is used to recover the elite genotype at the maximum number of polymorphic loci possible, while maintaining the desired phenotype. Backcross progeny are genotyped with SSR or SNP markers with an emphasis on selecting against samples exhibiting alleles from A and C genomes associated with *B. napus*. This process is effective when a large number of loci are required to obtain the desired phenotype.

Example 4

Further Modifications to Oil Profiles and Testing of Oil Profiles

Further improvement to oil seeds is accomplished by combining the B-genome fad2, fad3 mutations disclosed in Pub. No. US2008/0168587 (the contents of which are incorporated by reference) or mutations newly created in *B. nigra* or in *B. juncea* seed. In one example, crosses are made among various lines, selections are identified, and by combining these selections additional stable high oleic and low linolenic selections with comparable agronomic yields are produced.

Other potential ways to obtain and/or/identify other sources of mutant fad2b and/or fad3b genes include, for example: from known germplasm, from fast neutron/EMS mutants, from application of RNAi, from Zinc Finger mediated control of regulation of gene expression. The levels of expression of fad2b and fad3b enzymes can be reduced or eliminated by any of the methods described above.

B. nigra microspore mutagenesis

↓

Mutant production

↓ mutant evaluation through single seed NIR

↓

Identification of fatty acid and glucosinolate

Once genes are obtained/identified, mutant FAD genes are transferred into *B. juncea* plants by: (a) crossing DAS' *B. juncea* line with a second *B. nigra, B. carinata*, or *B. juncea* plant having a mutant fad2b gene and/or fad3b gene; (b) using molecular markers to track the introgression of the fad2b gene and/or fad3b gene; (c) obtaining seeds from the cross of step (a); (d) analyzing FAP of seeds, then growing fertile plants from seed selections; (e) obtaining progeny seed from self pollinating plants of step (d); (f) greenhouse and field testing of progeny across differing environments; and (g) identifying those seeds among the progeny that have a linolenic value of <3% and an oleic value of between about 68% to about 80%.

Down regulation of FAD2B and FAD3B enzymes is accomplished by deletion, insertion mutagenesis in the coding regions or regulatory domains within the native sequences.

Example 5

Hybrid *B. Juncea* Seed Oil Profile

HOLL oil profile is represented in hybrids produced by creating HOLL parental lines containing cytoplasmic male sterile systems (see, e.g., Ogura, *B. napus* CMS126-1) and their corresponding fertility restoration backgrounds.

Example 6

Introduction of Agronomic, Herbicide and Insecticide Traits into HOLL Juncea

Herbicide Resistance Trait (Imidazolinone-Resistance):

The imidazolinone resistance trait in *B. napus* (BASF) includes a PM2 mutation site located on LG01 (AA genome, approximately 20 cM from glyphosate-resistance insertion site) and a PM1 mutation site is located on LG11 (CC genome)). It is believed that ahas3 corresponds to the AA genome, while AHAS1 corresponds to the CC genome. Swanson et al., (*Theor. Appl Genet.* 78:525-530, 1989) indicates that ahas3 gene alone provides tolerance to imidazolinone herbicides. There are two other AHAS genes located on the AA genome: ahas2 and ahas4. AHAS genes located on the BB genome can be identified for mutagenesis if two ahas genes are needed for resistance to imidazolinone herbicides. It has been found with PM2 only in *B. juncea*, insufficient resistance is obtained. Therefore, two or more genes in *B. juncea* are developed to provide sufficient imidazolinone resistance.

Omega-9 IMI *B. napus* is crossed to *B. juncea*. Fertile seeds are planted and progeny of interspecific cross are sprayed with imidazolinone herbicides to assay for resistance. Presence of PM2 using Invader assay confirms presence of PM2 mutation. Assay for PM1 mutation to determine if the BB genome and CC genome chromosomes paired resulting in genetic transfer of PM1 from *B. napus* CC genome to *B. juncea* B genome.

If a mutation in the AHAS3 gene alone provides resistance to imidazolinone herbicides, an Omega-9 *B. napus* line containing PM2 is used in making crosses to *B. juncea* lines to negate the need to re-introduce *B. napus* germplams into finished HOLL *B. juncea* lines. Marker-assisted selection of imidazolinone-resistant *B. juncea* happens simultaneously with Recovery and Determination of the BB genome. Once an HOLL *B. juncea* imidazolinone-resistant line is developed, it is used for subsequent trait introgression into other *B. juncea* cultivars.

Introgression of New Herbicide Traits into HOLL *B. juncea*:

Development of glyphosate resistant *B. juncea* is accomplished through introduction of the TIPS mutation into *B. juncea* through the application of Zinc Finger technology. Five paralogs have been identified in *B. napus*, with one or two of these being the most highly expressed versions of the EPSPS gene. Modified epsps genes capable of resulting in a glyphosate resistance phenotype are found to be present on the A genome and are crossed into Omega-9 *B. juncea* to produce glyphosate resistant Omega-9 *B. juncea*.

Segregating progeny (T1S1, F2, or BC1) are planted. Leaf samples are collected for DNA isolation. Samples are sprayed for a herbicide selectable marker, followed by zygosity testing with gene-specific marker. Bulk segregant analysis (BSA) pools are formed by pooling DNA from a random sample of resistant and susceptible plants to comprise the resistant and susceptible classes. R and S pools, as well as elite cultivar and transformed donor cultivar, are genotyped using SSR or SNP markers to identify putative insertion chromosome. Selective genotyping is performed on the chromosome with skewed bulks to identify gene insertion site. Marker assisted introgression is used to introgress the gene of interest into desirable HOLL B. juncea.

ADDITIONAL EMBODIMENTS OF THE INVENTION

With the advent of molecular biology techniques that have allowed the isolation and characterization of genes that encode specific protein products, scientists in the field of plant biology developed a strong interest in engineering the plant genome to contain and express foreign or additional genes, or to express modified versions of native, genes (perhaps driven by different promoters) in order to alter the traits of a plant in a specific manner. Such foreign additional and/or modified genes are referred to herein collectively as "transgenes." Over the last 20 years, several methods for producing transgenic plants have been developed for various crops, which include *Agrobacterium*-mediated transformation and particle bombardment. For specific *Brassica* transformation protocols see for reference to patents (U.S. Pat. No. 5,188,958 issued to Moloney et al., Feb. 23, 1993; U.S. Pat. No. 6,051,756 issued to Chen et al., Apr. 18, 2000; U.S. Pat. No. 6,297,056 issued to Tulsieram et al., Oct. 2, 2001). The present invention, in particular embodiments, also relates to transformed versions of the claimed varieties or lines.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *Brassica* plants, using transformation methods as described below to incorporate transgenes into the genetic material of the *Brassica* plant(s).

Expression Vectors for *Brassica* Transformation: Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, which, when under the control of plant regulatory signals confers resistance to kanamycin (Fraley et al., *Proc. Natl. Acad. Sci. U.S.A.*, 80:4803, 1983). Another commonly used selectable marker gene is the hygromycin phosphotransferase gene which confers resistance to the antibiotic hygromycin (Vanden Elzen et al., *Plant Mol. Biol.*, 5:299, 1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., *Plant Physiol.* 86:1216, 1988; Jones et al., *Mol. Gen. Genet.*, 210:86, 1987; Svab et al., *Plant Mol. Biol.* 14:197, 1990; Hille et al., *Plant Mol. Biol.* 7:171, 1986).

Other selectable marker genes confer resistance to herbicides such as glyphosate, glufosinate, 2,4-D or bromoxynil (Comai et al., *Nature* 317:741-744, 1985; Lira et al., WO 2008/070845; Wright et al., WO 2005/107437 and WO 2007/053482; Gordon-Kamm et al., *Plant Cell* 2:603-618, 1990; Stalker et al., *Science* 242:419-423, 1988). Other selectable marker genes for plant transformation not of bacterial origin include, for example, mouse dihydrofolate reductase, plant 5-enol-pyruvyl-shikimate-3-phosphate synthase and plant acetolactate synthase (Eichholtz et al., *Somatic Cell Mol. Genet.* 13:67, 1987; Shah et al., *Science* 233:478, 1986; Charest et al., *Plant Cell Rep.* 8:643, 1990). A gene encoding Green Fluorescent Protein (GFP) has been utilized as a marker for gene expression in prokaryotic and eukaryotic cells (Chalfie et al., *Science* 263:802, 1994). GFP and mutants of GFP may be used as selectable markers.

Promoters: Genes included in expression vectors must be driven by a nucleotide sequence comprising a regulatory element, for example, a promoter. Several types of promoters are now well known in the transformation arts, as are other regulatory elements that can be used alone or in combination with promoters. As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type"-specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type-specific, and inducible promoters constitute the class of "non-constitutive" promoters. A "constitutive" promoter is a promoter which is active under most environmental conditions.

Inducible Promoters: An inducible promoter is operably linked to a gene for expression in *Brassica*. Optionally, the inducible promoter is operably linked to a nucleotide sequence encoding a signal sequence which is operably linked to a gene for expression in *Brassica*. With an inducible promoter the rate of transcription increases in response to an inducing agent. Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571, 1993); 1n2 gene from maize which responds to benzenesulfonamide herbicide safeners (Hershey et al., *Mol. Gen. Genetics* 227:229-237 (1991); and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

Constitutive Promoters: A constitutive promoter is operably linked to a gene for expression in *Brassica* or the constitutive promoter is operably linked to a nucleotide sequence encoding a signal sequence which is operably linked to a gene for expression in *Brassica*. Many different constitutive promoters can be utilized in the instant invention. Exemplary constitutive promoters include, but are not limited to, the promoters from plant viruses such as the 35S promoter from CaMV (Odell et al., *Nature* 313:810-812, 1985) and the promoters from such genes as rice actin (McElroy et al., *Plant Cell* 2:163-171, 1990); ubiquitin (Christensen et al., *Plant Mol. Biol.* 12:619-632, 1989; Christensen et al., *Plant Mol. Biol.* 18:675-689 (1992); pEMU (Last et al., *Theor. Appl. Genet.* 81:581-588, 1991); MAS (Velten et al., *EMBO J.* 3:2723-2730, 1984); maize H3 histone (Lepetit et al., *Mol. Gen. Genetics* 231:276-285, 1992; Atanassova et al., *Plant Journal* 2 (3):291-300, 1992). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO 96/30530.

Tissue-specific or Tissue-preferred Promoters: A tissue-specific promoter is operably linked to a gene for expression in *Brassica*. Optionally, the tissue-specific promoter is operably linked to a nucleotide sequence encoding a signal sequence which is operably linked to a gene for expression in *Brassica*. Plants transformed with a gene of interest operably linked to a tissue-specific promoter produce the protein product of the transgene exclusively, or preferentially, in a specific tissue. Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985), and Timko et al., Nature 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); C. Knox et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel et al., *Plant Cell* 2:785-793 (1990).

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a particular embodiment of the invention, the transgenic plant provided for commercial production of foreign protein is a *Brassica* plant. In another embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Methods for *Brassica* Transformation: Numerous methods for plant transformation have been developed including biological and physical plant transformation protocols. See, for example, Mild et al., "Procedures for Introducing Foreign DNA into Plants" in *Methods in Plant Molecular Biology and Biotechnology*, B. R. Glick and J. E. Thompson, Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, B. R. Glick and J. E. Thompson, Eds. (CRC Press, Inc., Boca Raton, 1993) pages 89-119.

*Agrobacterium*-mediated Transformation: One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, C. I. Kado, *Crit. Rev. Plant Sci.* 10:1 (1991). Descriptions of *Agrobacterium* vector systems and methods for *Agrobacterium*-mediated gene transfer suitable for purposes of the present invention are provided by Bhalla and Singh, *Nature Protocols* 3(2):181-9 (2008), Cardoza and Stewart, *Methods Mol. Biol.* 343:257-66 (2006), Gruber et al., supra, Mild et al., supra, and Moloney et al., *Plant Cell Reports* 8:238 (1989). See also, U.S. Pat. No. 5,563,055 (Townsend and Thomas), issued Oct. 8, 1996.

Direct Gene Transfer: Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 µm to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), J. C. Sanford, *Trends Biotech.* 6:299 (1988), Klein et al., *Bio/Technology* 6:559-

563 (1988), J. C. Sanford, *Physiol. Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.* 4:2731 (1985), Christou et al., *Proc Natl. Acad. Sci. U.S.A.* 84:3962 (1987). Direct uptake of DNA into protoplasts using CaCl2 precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In *Abstracts of VIIth International Congress on Plant Cell and Tissue Culture IAPTC,* A2-38, p 53 (1990); D'Halluin et al., *Plant Cell* 4:1495-1505 (1992), and Spencer et al., *Plant Mol. Biol.* 24:51-61 (1994).

Following transformation of *Brassica* target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed with another (non-transformed or transformed) variety in order to produce a new transgenic variety. Alternatively, a genetic trait which has been engineered into a particular *Brassica* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of *Brassica*: Further production of the *B. juncea* lines can occur by self-pollination or by tissue culture and regeneration. Tissue culture of various tissues of *Brassica* and regeneration of plants therefrom is known. For example, the propagation of a *Brassica* cultivar by tissue culture is described in any of the following, but not limited to any of the following: Chuong et al., "A Simple Culture Method for *Brassica* Hypocotyl Protoplasts," *Plant Cell Reports* 4:4-6 (1985); T. L. Barsby et al., "A Rapid and Efficient Alternative Procedure for the Regeneration of Plants from Hypocotyl Protoplasts of *Brassica napus*," *Plant Cell Reports* (Spring, 1996); K. Kartha et al., "In vitro Plant Formation from Stem Explants of Rape," *Physiol. Plant,* 31:217-220 (1974); S. Narasimhulu et al., "Species Specific Shoot Regeneration Response of Cotyledonary Explants of *Brassicas*," *Plant Cell Reports* (Spring 1988); E. Swanson, "Microspore Culture in *Brassica*," *Methods in Molecular Biology*, Vol. 6, Chapter 17, p. 159 (1990).

Thus, another aspect of this invention is to provide cells that upon growth and differentiation produce *Brassica* plants having the physiological and morphological characteristics of *B. juncea* lines of the present invention.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, siliques, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, described certain techniques, the disclosures of which are incorporated herein by reference.

This invention also is directed to methods for producing a *Brassica* plant by crossing a first parent *Brassica* plant with a second parent *Brassica* plant wherein the first or second parent *Brassica* plant is a *Brassica* plant including at least one mutated FAD gene (i.e., FAD2 and/or FAD3). Thus, any such methods using the *Brassica juncea* line of the present invention are part of this invention: selfing, backcrosses, hybrid production, crosses to populations, and the like.

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a canola plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, for example Jones et al., *Science* 266:789 (1994) (cloning of the tomato Cf-9 gene for resistance to *Cladosporium falvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (Arabidopsis RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor); Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* .alpha.-amylase inhibitor); and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor); and Pratt et al., *Biochem. Biophys. Res. Comm.* 163:1243 (1989) (an allostatin is identified in *Diploptera puntata*). See also U.S. Pat. No. 5,266,317 to Tomaiski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones; and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci.* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Mild et al., *Theor. Appl. Genet.* 80:449 (1990), respectively.

B. Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (ACCase inhibitor-encoding genes), See, for example, U.S. Pat. No. 4,940,835 to Shah et al., and U.S. Pat. No. 6,248,876 to Barry et al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al., DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893, both assigned to Dow AgroSciences LLC.

C. An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Sogaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

A deposit of the Dow AgroSciences, Inc. proprietary *Brassica juncea* line disclosed above and recited in the appended claims has been made with the American Type Culture Collection (ATCC), 10801 University Boulevard, Manassas, Va. 20110. The date of deposit was Mar. 22, 2010. The deposit of 2500 seeds was taken from the same deposit maintained by Dow AgroSciences, Inc., since prior to the filing date of this application. All restrictions upon the deposit have been removed, and the deposit is intended to meet all of the requirements of 37 C.F.R. 1.801-1.809. The ATCC accession numbers are PTA10724 and PTA-10725. The deposit will be maintained in the depository for a period of 30 years, or 5 years after the last request, or for the effective life of the patent, whichever is longer, and will be replaced as necessary during that period.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The invention includes all embodiments and variations substantially as hereinbefore described and with reference to the examples and drawings.

What is claimed is:

1. A *Brassica juncea* seed having an endogenous fatty acid content comprising at least 70.0% oleic acid by weight and less than 3.0% linolenic acid by weight.

2. The *Brassica juncea* seed of claim 1 whose seeds have an endogenous fatty acid content comprising 70.0% to 85.0% oleic acid by weight.

3. The *Brassica juncea* seed of claim 1 whose seeds have an endogenous fatty acid content comprising 70.0% to 85.0% oleic acid by weight and less than 3.0% linolenic acid by weight.

4. The seed according to claim 1, wherein the seed has total extractable oils comprising a fatty acid content of at least 70.0% oleic acid by weight and less than 3.0% linolenic acid by weight.

5. The seed of claim 4 having total extractable oils comprising an oleic acid content of 70.0% to 85.0% by weight and a linolenic acid content of 0.1% to 3.0% by weight.

6. The *Brassica juncea* seed of claim 1, containing a mutated fad2 gene.

7. The *Brassica juncea* seed of claim 1, containing a mutated fad3 gene.

8. A method of producing a *Brassica juncea* seeds have an endogenous fatty acid content comprising at least 70.0% oleic acid by weight and less than 3.0% linolenic acid by weight, comprising:

introducing into a *Brassica juncea* plant, through traditional crossing methods, one or more nucleic acid sequences selected from the group consisting of a mutated fad2a nucleic acid sequence, a mutated fad2b nucleic acid sequence, a mutated fad3a nucleic acid sequence, and a mutated fad3b nucleic acid sequence.

9. *Brassica juncea* seeds, said seeds having one or more non-recombinant fad2 and fad3 genes from one or more genomic components of a *Brassica* aa and/or *Brassica* bb genome, said seeds having a fatty acid content comprising at least 70.0% oleic acid by weight and less than 3.0% linolenic acid by weight.

10. One or more generations of progeny plants produced from at least one of the seeds of claim 9, wherein seeds of said progeny plants comprise at least 70.0% oleic acid by weight and less than 3.0% linolenic acid by weight.

11. Seeds of a *Brassica juncea* cultivar having, on average, an endogenous oil content which averages, across the crop, at least 70.0% oleic acid by weight and less than 3.0% linolenic acid by weight.

12. Meal from the seeds of claim 11.

13. The meal of claim 12, wherein the meal is in the form of crushed seeds, press cake, white flake, or the meal from conventional crushing and solvent extraction processes.

* * * * *